United States Patent
Jefferies et al.

(10) Patent No.: US 11,213,571 B2
(45) Date of Patent: Jan. 4, 2022

(54) MODULATION OF CANCER IMMUNITY WITH TYPE 2 INNATE LYMPHOID CELLS, INTERLEUKIN 33, AND/OR INTERFERON INDUCED PROTEIN 44

(71) Applicant: Wilfred Jefferies, Surrey (CA)

(72) Inventors: Wilfred Jefferies, Surrey (CA); Iryna Yuriyivna Saranchova, Surrey (CA)

(73) Assignee: CAVA HEALTHCARE INC., Surrey (CA)

( * ) Notice: Subject to any disclaimer, the term of this patent is extended or adjusted under 35 U.S.C. 154(b) by 50 days.

(21) Appl. No.: 15/555,202

(22) PCT Filed: Mar. 3, 2016

(86) PCT No.: PCT/CA2016/050227
§ 371 (c)(1),
(2) Date: Sep. 1, 2017

(87) PCT Pub. No.: WO2016/138590
PCT Pub. Date: Sep. 9, 2016

(65) Prior Publication Data
US 2018/0050091 A1    Feb. 22, 2018

Related U.S. Application Data

(60) Provisional application No. 62/127,407, filed on Mar. 3, 2015, provisional application No. 62/264,430, filed on Dec. 8, 2015.

(51) Int. Cl.
| | |
|---|---|
| A61K 38/20 | (2006.01) |
| A61K 35/17 | (2015.01) |
| C12N 5/078 | (2010.01) |
| C12N 5/0783 | (2010.01) |
| G01N 33/574 | (2006.01) |
| C07K 14/54 | (2006.01) |
| C07K 14/47 | (2006.01) |
| A61K 38/21 | (2006.01) |
| A61K 45/06 | (2006.01) |
| C12Q 1/6886 | (2018.01) |
| A61K 39/00 | (2006.01) |

(52) U.S. Cl.
CPC ............ *A61K 38/20* (2013.01); *A61K 35/17* (2013.01); *A61K 38/21* (2013.01); *A61K 45/06* (2013.01); *C07K 14/4718* (2013.01); *C07K 14/54* (2013.01); *C12N 5/0636* (2013.01); *C12Q 1/6886* (2013.01); *G01N 33/57407* (2013.01); *G01N 33/57423* (2013.01); *G01N 33/57434* (2013.01); *G01N 33/57438* (2013.01); *G01N 33/57488* (2013.01); *A61K 2039/5158* (2013.01); *C12N 2501/2333* (2013.01); *C12Q 2600/118* (2013.01); *C12Q 2600/158* (2013.01); *G01N 2333/54* (2013.01); *G01N 2800/52* (2013.01)

(58) Field of Classification Search
CPC ....... A61K 38/20; A61K 35/17; C12N 5/0636
See application file for complete search history.

(56) References Cited

U.S. PATENT DOCUMENTS

2005/0203046 A1* 9/2005 Schmitz ............... C07K 16/244
514/44 A

FOREIGN PATENT DOCUMENTS

| CN | 101203247 | 6/2008 |
| CN | 102971001 | 3/2013 |
| JP | 2007523089 | 8/2007 |
| WO | WO 2005/079844 | 9/2005 |

OTHER PUBLICATIONS

Ishikawa et al., Auris Nasus Larynx, 2014, 41:552-557.*
Constantinidou et al., Targeting Programmed Cell Death-1 (PD-1) and Ligand (PD-L1): A new era in cancer active immunotherapy, Pharmacology & Therapeutics, 194: 84-106. (Year: 2019).*
Lin et al., A PD-L1-Based Cancer Vaccine Elicits Antitumor Immunity in a Mouse Melanoma Model, Molecular Therapy: Oncolytics, 14: 222-232. (Year: 2019).*
Alimonti et al., "TAP expression provides a general method for improving the recognition of malignant cells in vivo", Nature Biotechnology, 18(5):515-520 (May 2000).
Alpan et al., "Cell cycle-dependent expression of TAP1, TAP2, and HLA-B27 messenger RNAs in a human breast cancer cell line", Cancer Research, 56(19):4358-4361 (Oct. 1996).
Roediger and Weninger, "Group 2 innate lymphoid cells in the regulation of immune response", Adv. Immunol., 125:111-154 (2015), Epub Dec. 2014.
Blades et al., "Loss of HLA class I expression in prostate cancer: implications for immunotherapy", Urology, 46 (5):681-686 (Nov. 1995).
Carretero et al., "Eosinophils orchestrate cancer rejection y normalizing tumor vessels and enhancing infiltration of CD8(+) T cells", Nature Immunology, 16(6):609-617 (Jun. 2015), Epub Apr. 2015.
Carriere et al., "IL-33, the IL-1 -like cytokine ligand for ST2 receptor, is a chromatin-associated nuclear factor in vivo", PNAS, 104(1):282-287 (Jan. 2007), Epub Dec. 2006.
Cayrol and Girard, "IL-33: alarmin cytokine with crucial roles in innate immunity, inflammation and allergy", Curr. Opin. Immunol., 31:31-37 (Dec. 2014), Epub Sep. 2014.

(Continued)

*Primary Examiner* — Hong Sang
(74) *Attorney, Agent, or Firm* — McDonnell Boehnen Hulbert & Berghoff LLP

(57) ABSTRACT

The present invention provides methods of modulating of cancer immunity using type 2 innate lymphoid cells (IL-C2s), interleukin 33 (IL-33), IFI44 or combination thereof. Also provided are methods of preventing tumor metastasis and/or cancer progression by treatment with therapies comprising type 2 innate lymphoid cells (ILC2s), interleukin 33 (IL-33), IFI44 or combination thereof. Also provided are diagnostic methods for assessing cancer prognosis.

12 Claims, 85 Drawing Sheets
Specification includes a Sequence Listing.

(56) References Cited

OTHER PUBLICATIONS

Deleeuw et al., "CD25 identifies a subset of CD4+ FoxP3-Til that are exhuasted yet prognostically favorable in human ovarian cancer", Cancer Immunology Research, 3(3);245-253 (Mar. 2015), Epub Dec. 2014.
Delp et al., "Functional deficiencies of components of the MHC class 1 antigen pathway in human tumors of epithelial origin". Bone Marrow Transplant, 25 Suppl 2: S88-95 (May 2000).
Dominguez et al., "Induction of robust antitumor immunity by exogenous interleukin-33", Journal of Immunolgy, 194 (Supple 1) Abstract 69.2 (May 2015).
Drake et al., "Group 2 innate lymphoid cells and CD4+ T cells cooperate to mediate type 2 immune response in mice", Allergy, 69(10):1300-7 (Oct. 2014), Epub Jun. 2014.
Fine et al., "Tobacco reduces membrane HLA class I that is restored by transfection with transporter associated with antigen processing 1 cDNA", J. Immunol., 169(10):6012-6019 (Nov. 2002).
Fridman et al., "The immune contexture in human tumours: impacton clinical outcome", Nat. Rev. Cancer, 12(4): 298-306 (Mar. 2012).
Gabathuler et al., "Comparison of cell lines deficient in antigen presentation reveals a functional role for TAP-1 alone in antigen processing", J. Exp Med., 180(4):1415-25 (Oct. 1994).
Gao et al., "Tumoral expression of IL-33 inhibits tumor growth and modifies the tumor microenvironment through CD8+ T and NK cells", Journal of Immunology, 194(1):438-445 (Jan. 2015).
Gao et al., "Transgenic expression of IL-33 activates CD8+ T cells and NK cells and inhibits tumor growth and metastasis in mice", Cancer Letters, 335(2):463-471 (Jul. 2013).
Giorda et al., "The antigen processing machinery of class I human leukocyte antigens: linked patterns of gene expression in neoplastic cells", Cancer Research, 63(14):4119-4127 (Jul. 2003).
Guabiraba et al., "IL-33 targeting attenuates intestinal mucositis and enhances effective tumor chemotherapy in mice", Mucosal Immunol., 7(5):1079-1093 (Sep. 2014), Epub Jan. 2014.
Halim et al., "Retinoic-acid-receptor-related orphan nuclear receptor alpha is required for natural helper cell development and allergic inflammation", Immunity, 37(3):463-474 (Sep. 2012).
Hallen et al., "Antiproliferative activity of the human IFN-alpha-inducible protein IFI44", J. Interferon and Cytokine Research, 27(8):675-680 (Aug. 2007).
Hanahan and Weinberg, "Hallmarks of cancer: the next generation", Cell, 144(5):646-674 (Mar. 2011).
Harris et al., "Gene therapy through signal transduction pathways and angiogenic growth factors as therapuetic targets in breast cancer", Cancer, 74(3 Suppl1):1021-5 (Aug. 1994).
Ishikawa et al., "Expression of interleukin-33 is correlated with poor prognosis of patients with squamous cell carinoma of the tongue" Auris, Nasus, Larynx, 41(6):552-557 (Dec. 2014).
Johnsen et al., "Deficiency of transporter for antigen presentation (TAP) in tumor cells allows evasion of immune surveillance and increases tumerigenesis", J. Immunol, 163(8):4424-4231 (Oct. 1999).
Kaklamanis et al., "Loss of transporter in antigen processing 1 transport protein and major histocompatibility complex class I molecules in metastatic versus primary breast cancer", Cancer Research, 55(22):5191-5194 (Nov. 1995).
Kattunen, J., et al. "Detection of rare antigen-presenting cells by the lacZ T-cell activation assay suggests an expression cloning strategy for T-cell antigens," Proc Natl. Acad. Sci U.S.A., 89(13):6020-6024 (1992).
Kearley et al., "Cigarette smoke silences innate lymphoid cell function and facilitates an exacerbated type I Interleukin-33-dependent response to infection", Immunity, 42(3):566-79 (Mar. 2015).
Kitamura et al., "Down-regulation of HLA class I antigen is an independent prognostic factor for clear cell renal cell carcinoma", Adult Urology, 177(4):1269-1272 (Apr. 2007).

Rosenberg et al., "Adoptive cell transfer: a clinial path to effective cancer immunotherapy", Nature Reviews Cancer, 3(4):299-308 (Apr. 2008).
Korkolopoulou et al., "Loss of antigen-presenting molecules (MHC class I and TAP-1) in lung cancer", Br. J. Cancer, 73(2):148-53 (Jan. 1996).
Lanier et al., "Shades of grey—the bluring view of innate and adaptive immunity", Nat. Rev. Immunol., 13(2):73-74 (Feb. 2013).
Lankat-Buttgereit and Tampe, "The transporter associated with antigen processing: function implications in human diseases", Physiol. Rev., 82(1):187-204 (Jan. 2002).
Lee et al., "Resistance to lysis by cytotoxic T cells: a dominant effect in metastitic mouse prostate cancer cells", Cancer Research, 60(7): 1927-1933 (Apr. 2000).
Liu et al., "TAP peptide transporter-independent presentation of heat-killed Sendai virus antigen on MHC class I molecules by splenic antigen-presenting cells", J. Immunol., 159(11):5364-5371 (Dec. 1997).
Lou et al., "Combining the antigen processing components TAP and Tapasin elicits enhanced tumor-free survival", Clin. Cancer Research, 14(5):1494-1501 (Mar. 2008).
Lou et al., "Restoration of the expression of transporters associated with antigen processing in lung carcinoma increses tumor-specific immune responses and survival", Cancer Research, 65(17):7926-7933 (Sep. 2005).
Martin, "Special aspects of interleukin-33 and the IL-33 receptor complex", Semin Immunol., 25(6):449-457 (Dec. 2013), Epub Nov. 2013.
Martinez-Gonzalez et al., "Lung ILC2s link innate and adaptive responses in allergic inflammation", Trends In Immunology, 36(3):189-195 (Mar. 2015), Epub (Feb. 2015).
McKenzie et al., "Innate lymphoid cells in inflammation and immunity", Immunity, 41 (3):366-374 (Sep. 2014).
Mehta et al., "Association of antigen processing machinery and HLA class I defects with clinicopathological outcome in cervical carcinoma", Cancer Immunol. Immunother., 57(2): 197-206 (Feb. 2008), Epub Jul. 2007.
Mjosberg et al., "Human IL-25 and IL-33-responsive type 2 innate lymphoid cells are defined by expression of CRTH2 and CD161", Nature Immunology, 12(11):1055-1062 (Sep. 2011).
Musolino et al., "Reduction in IL-33 plasma levels might be involved in T-cell dysregulation in chronic lymphocytic leukemia", Acta Haematol., 131 (3): 165-166 (2014), Epub Nov. 2013.
Nabe, "Interleukin(IL)-33: new therapeutic target for atopic diseases", J. Pharmacol. Sci., 126(2):85-91 (2014), Epub Sep. 2014.
Naoe et al., "Correlation between major histocompatibility complex class I molecules and CD8+ T lymphocytes in prostate, and quantification of CDS and interferon-gamma mRNA in prostate tissue specimens", BJU Int., 90 (70:748-753 (Nov. 2002).
Neill et al., "Nuocytes represent a new innate effector leukocyte that mediates type-2 immunity", Nature, 464 (7293):1367-1370 (Apr. 2010), Epub Mar. 2010.
Pascual-Figal and Januzzi, "The biology of ST2: the International ST2 consensus panel", Am. J. Cardiol., 115(7 Suppl): 3B-7B (Apr. 2015), Epub Jan. 2015.
Rigamonti and Bellone, "Prostate cancer, tumor immunity and renewed sense of optimism in immunotherapy", Cancer Immunol. Immunother., 61(4):453-468 (Apr. 2012), Epub Feb. 2012.
Ritz and Seliger, "The transporter associated with antigen processing (TAP): structurally integrity, expression, function, and its clinical relevance", Mol. Med., 7(3):149-158 (Mar. 2001).
Seliger et al., "Antigen-processing machinery breakdown and tumor growth", Immunol. Today, 21(9):455-464 (Sep. 2000).
Seliger et al., "TAP off-tumors on", Immunol. Today, 18(6):292-299 (Jun. 1997).
Setiadi et al., "Epigenetic enhancement of antigen processing and presentation promotes immune recognition of tumors", Cancer Research, 68(23):9601-9607 (Dec. 2008).
Shastri and Gonzalez, "Endogenous generation and presentation of the ovalbumin peptide/Kb complex to T cells", J. Immunol., 150(7):2724-2736 (Apr. 1993).

(56) References Cited

OTHER PUBLICATIONS

Singal et al., "Molecular basis for lack of expression of HLA class I antigens in human small-cell lung carcinoma cell lines", Int J. Cance, 68(5):629-636 (Nov. 1996).
Slovin, S. "Biomarkers for immunotherapy in genitourinary malignancies," Urol. Oncol., 34(4):1205-213 (2016).
Smahel et al., "Immunisation with modified HPV16 E7 genes against mouse oncogenic TC-1 cell sublines with downregulated expression of MHC class I molecules", Vaccine, 21(11-12):11125-1136 (Mar. 2003).
Spits et al., "Innate lymphoid cells-a proposal for uniform nomenclature", Nat. Rev. Immunol., 13(2):1145-149 (Feb. 2013).
Sun et al., "Serum interleukin-33 levels in patients with gastric cancer", Digestive Diseases Sciences, 4(4):13596-601 (Dec. 2011).
Tao et al., "Imagable 4T1 model for the study of late stage breast cancer", BMC Cancer, 8:228 (Aug. 2008).
Taylor et al., "Integrative genomic profiling of human prostate cancer", Cancer Cell, 18(1):11-22 (Jul. 2010), Epub Jun. 2010.
Tominaga et al., "Dual function of Il-33 on proliferation of NIG-3T3 cells", Cytokine, 72(1):105-108 (Mar. 2015), Epub Jan. 2015.
Villarreal et al., "Alarmin IL-33 acts as an immunoadjuvant for enhancing antigen-specific cell-mediated immunity, resulting in potent anti-tumor immunity", Cancer Research, 74(6): 1789-1800 (Mar. 2014), Epub Jan. 2014.
Vitale et al., "HLA class I antigen and transporter associated with antigen processing (TAP1 and TAP2) down-regulation in high-grade primary breast carcinoma lesions", Cancer Research, 58(4):737-742 (Feb. 1998).
Walker et al., "Innate lymphoid cells—how did we miss them?", Nat. Rev. Immunol., 13(2):75-87 (Feb. 2013), Epub Jan. 2013.
Watson et al., "Expression of the membrane complement regulatory protein CD59 (protectin) is associated with reduced survival in colorectal cancer patients", Cancer Immunol Immunother, 55(8):973-980 (Aug. 2006).
Wyatt et al., "Heterogeneity in the inte-tumor transcriptome of high risk prostate cancer", Genome Biol., 15(8):426 (Aug. 2014).
Zhang et al., "Concordant down-regulation of proto-oncogene PML and major histocompatibility antigen HLA class I expression in high-grade prostate cancer", Cancer Immun., 3:2 (Feb. 2003).
Zhang et al., "TAP expression reduces IL-10 expressing tumor infiltrating lymphocytes and restores immunosurveillance against melanoma", Int. J. Cancer, 120(9):1935-1941 (May 2007).
Zhang et al., "Trogocytosis of MHC-I/peptide complexes derived from tumors and infected cells enhances dendritic cell cross-priminary and promotes adaptive T cell responses", PLoS One, 3(8):e3097 (Aug. 2008).

Zia et al., "MHC class I negative phenotype of disseminated tumor cells in bone marrow is associated with poor survival in R0M0 breast cancer patients", Int J. Cancer, 93(4):566-570 (Aug. 2001).
GenBank Accession No. NM_001164724.1 Jan. 18, 2018 (4 pages).
International Preliminary Report on Patentability issued by the International Searching Authority for International Applicatin No. PCT/CA2016/050227 dated Sep. 5, 2017 (8 pages).
International Search Report by the International Searching Authority for International Application No. PCT/CA2016/050227 dated Jun. 1, 2016 (5 pages).
Written Opinion issued by the International Searching Authority for International Application No. PCT/CA2016/050227 dated Jun. 1, 2016 (8 pages).
Canadian Cancer Society "General cancer statistics at a glance," 2012, http://www.cancer.ca/British%20Columbia-Yukon/About%20cancer/Cancer%20statistics/Stats%20at%20a%20glance/General%20cancer%20stats.aspx?sc_lang=en&r=1 2013.
Canadian Cancer Society "Cancer in Canada in 2020," Statistical Infographic (2020).
Canadian Cancer Society "Canadian Cancer Statistics," (2019).
Janeway, C., Travers, P., et al., Immunobiology: the Immune System in Health and Disease., 7th ed. (New York: NY Garland Publishing) (2008).
Kim Juyang, "An IL-33 immunotherapy that blocks tumor growth by establishing innate lymphoid cells," The FASEB Journal, Federation of American Societies for Experimental Biology, vol. 28, No. 1, Suppl. S, p. LB52 (2014).
Matrinez-Gonzalez, I., et al. "Immunological Memory ofGroup 2 Innate Lymphoid Cells," Trends Immunol., 38(6):423-431 (2017).
Matrinez-Gonzalez, I., et al. "ILC2 memory: Recollection of previous activation," Immunol Rev, 283(1):41-53 (2018).
Nicholl et al., "Su2026 IL-33 Inhibits Proliferation and Induces of Apoptosis of Pancreatic Cancer Cells", Gastroenterology, vol. 142, No. 5, pp. S-1067 (2012).
Seliger, B., et al. "Coordinate downregulation of multiple MHC class I antigen processing genes in chemical-induced murine tumor cell lines of distinct origin," Tissue Antigens 56(4):327-336 (2000).
Setiadi, A.F., et al. "Identification of mechanisms underlying transporter associated with antigen processing deficiency in metastatic murine carcinomas" Cancer Res., 65(16):7485-92 (2005).
Zhou et al., ""Research progress on the correlation between IL-33 and its receptor and genesis and development of tumor,"" Chinese Journal of Surgery Concepts & Practice, vol. 18, No. 6, 581-585 (2013).

* cited by examiner a)
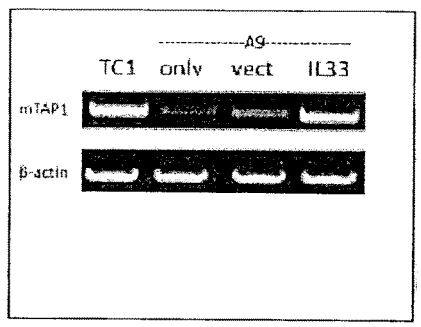
b)
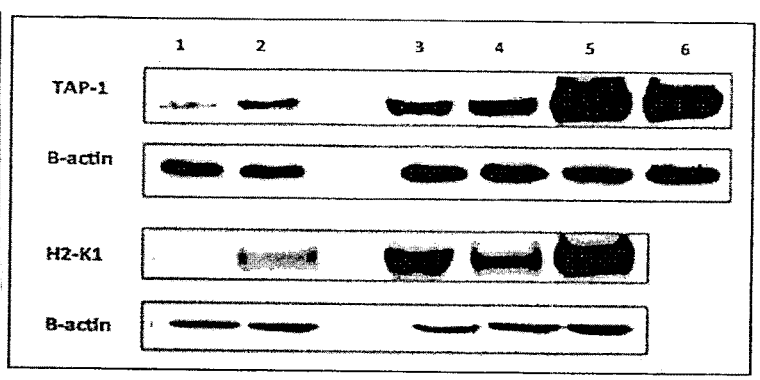
c)
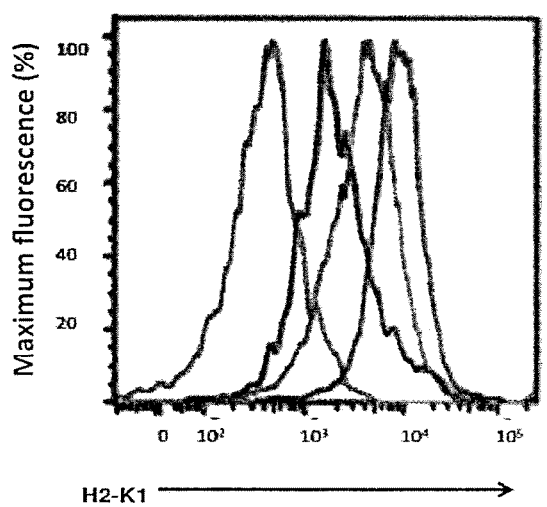
Figure 3

Figure 8

Most affected GO ID's between metastatic and non-metastatic cell lines

| GO Term | p-value | Count in Selection | % Count in Selection | Count in Total | % Count in Total |
|---|---|---|---|---|---|
| ossification | 1.1339363E-4 | 4 | 8.333333 | 70 | 0.40341172 |
| 2'-5'-oligoadenylate synthetase activity | 6.760445E-6 | 4 | 8.333333 | 5 | 0.028815122 |
| extracellular matrix structural constituent | 1.2215195E-4 | 4 | 8.333333 | 24 | 0.1383126 |
| extracellular region | 7.852311E-5 | 32 | 66.666664 | 1437 | 8.2814665 |
| proteinaceous extracellular matrix | 2.8828124E-9 | 17 | 35.416668 | 255 | 1.4695712 |
| collagen type I | 1.18017284E-4 | 2 | 4.1666665 | 2 | 0.011526049 |
| immune response | 2.5404102E-5 | 12 | 25 | 344 | 1.9824804 |
| antigen processing and presentation | 3.185333E-5 | 6 | 12.5 | 56 | 0.32272938 |
| extracellular matrix | 6.817064E-9 | 17 | 35.416668 | 270 | 1.5560166 |
| fibril | 2.4831581E-5 | 1 | 2.0833333 | 6 | 0.03457815 |
| extracellular matrix part | 1.4547174E-5 | 3 | 6.25 | 101 | 0.58206546 |
| extracellular region part | 7.8734E-7 | 18 | 37.5 | 656 | 3.780544 |

Figure 21

Selected candidate: MR1 – non-peptide presenting molecule
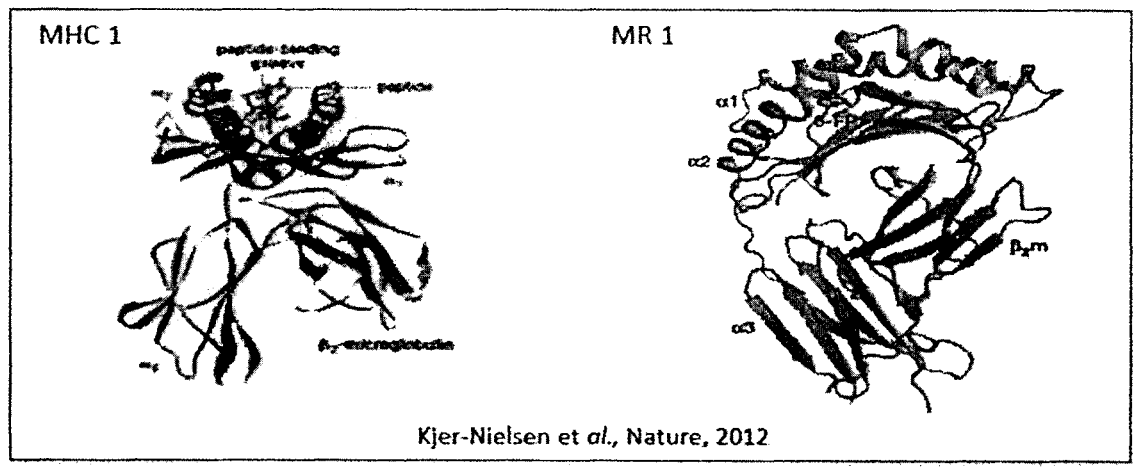
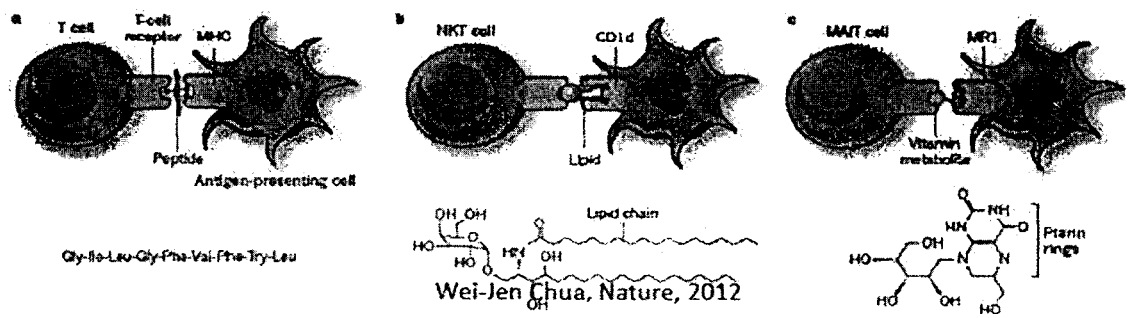
Figure 24

Gene-candidates are down regulated in human metastatic prostate cancer

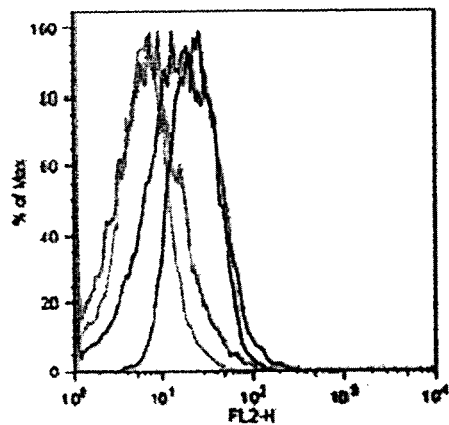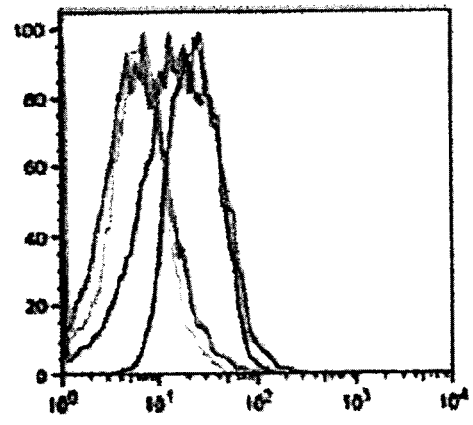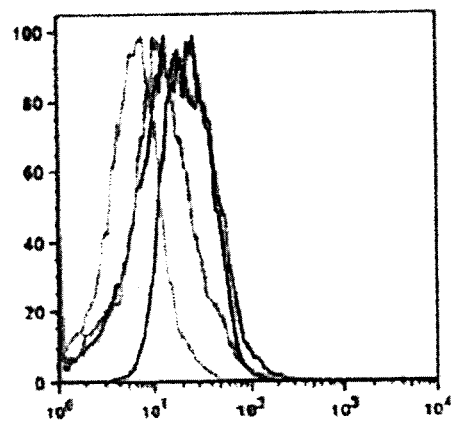
Figure 32

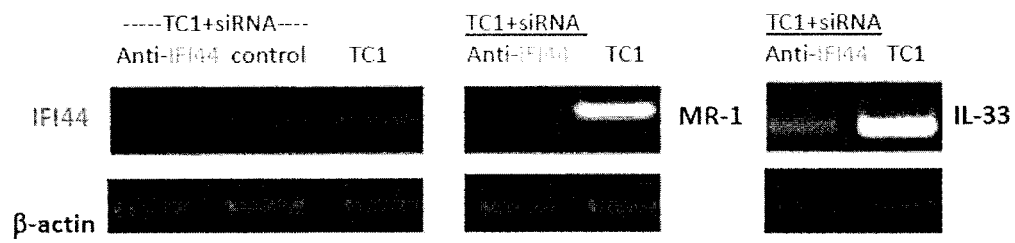
siRNA targeted against MR1 in TC-1 cells downregulates IFI44 gene expression
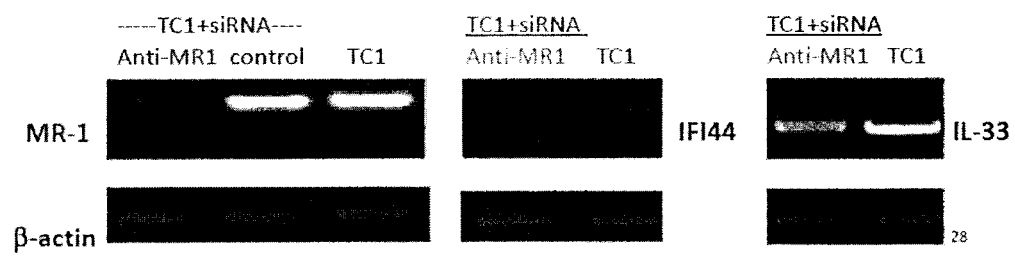
Figure 35

Mechanism of Immune recognition and Immune escape
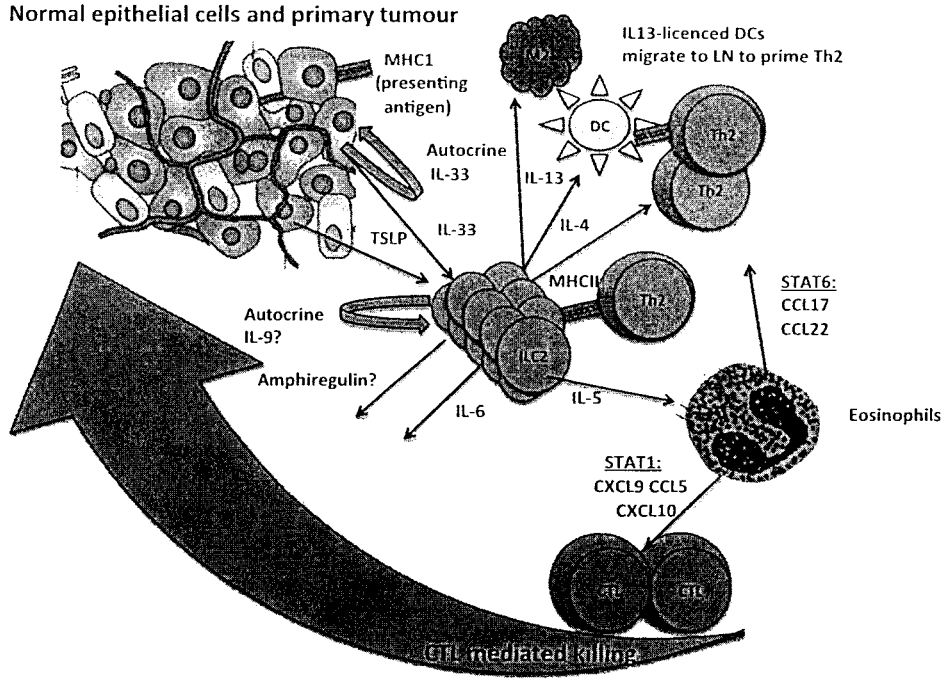
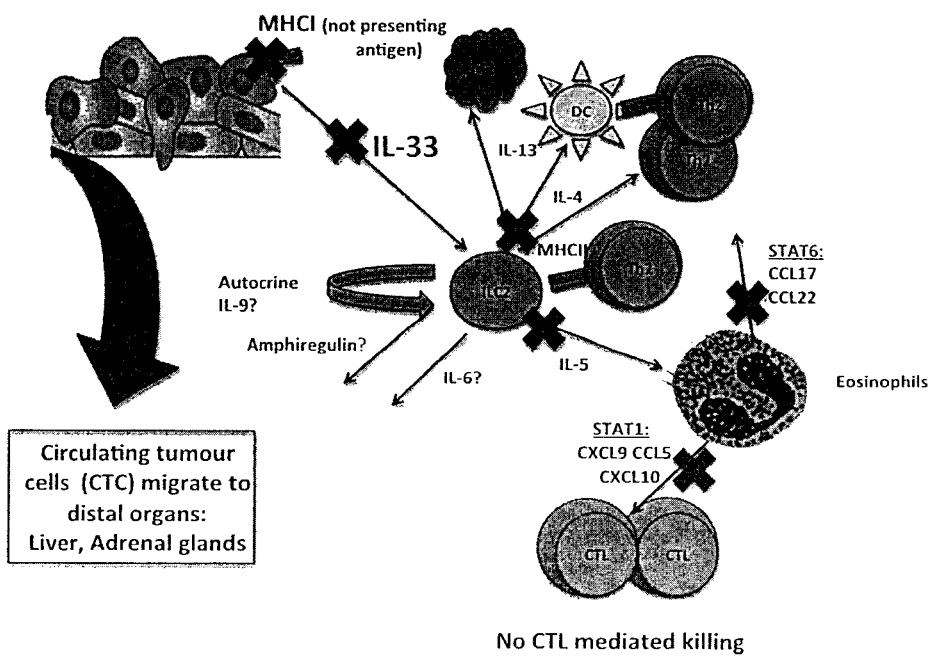
Figure 58

Prior Art: Spits H. et al., 2013

MODULATION OF CANCER IMMUNITY WITH TYPE 2 INNATE LYMPHOID CELLS, INTERLEUKIN 33, AND/OR INTERFERON INDUCED PROTEIN 44

This application is a national stage application under 35 U.S.C. § 371 of International Application No. PCT/CA2016/050227, filed Mar. 3, 2016, which claims the benefit of U.S. Provisional Patent Application No. 62/127,407, filed Mar. 3, 2015 and U.S. Provisional Patent Application No. 62/264,430, filed Dec. 8, 2015, the disclosures of which are explicitly incorporated herein in their entirety by reference.

FIELD OF THE INVENTION

The present invention relates to the field of cancer immunity. In particular, the present invention relates to modulation of cancer immunity with type 2 innate lymphoid cells (ILC2s), interleukin 33 (IL-33) and/or interferon induced protein 44 (IFI44).

BACKGROUND OF THE INVENTION

Cancer is the leading cause of death in the developed world and arises as a result of genetic mutations that occur in oncogenes and tumor suppressor genes. These mutations cause uncontrolled cell proliferation and may enable primary tumors to continue to mutate and evolve into the metastatic form of the disease that is often lethal (Hanahan and Weinberg, 2011; Janeway et al., 2008). Genomic profiling of tumors has revealed a "metastatic gene signature" common to many different tumor types (Hanahan and Weinberg, 2011). This metastatic signature distinguishes tumors with localized growing potential from those genetically configured to disseminate to distant sites. As such, genes mediating tumor cell motility, invasion, immune evasiveness, angiogenesis and colonization are classified as metastasis progression genes. The proteins encoded by these genes allow tumor cells to overcome cell-to-cell adhesion forces, move to distal sites, survive and colonize distal organs, while being immunologically undetectable.

The immune system limits the emergence of tumors. The cellular arm of the immune system is critical in providing protection against metastatic cancers. CD8+ T cells of the immune system are able to distinguish between normal cells and cancerous or virus-infected cells by monitoring major histocompatibility complex class I (MHC-I) molecules on the cell surface. MHC-I molecules, known in humans as the human leukocyte antigen (HLA) genes, are displayed by virtually all cells and form a complex with fragments of protein, or peptides, from the cell. Tumors express proteins that are related to the neoplastic transformation event and subsequent growth and expansion of the tumor. Antigenic peptides from these proteins termed tumor-associated antigens (TAA) are the focus of current immunotherapeutic approaches. Thus, the current paradigm holds that the emergence of tumors should be limited by a robust adaptive immune response that recognizes aberrant expression of TAAs (Setiadi et al., 2008; Zhang et al., 2008). During cancer development, neoplastic cells can undergo multifarious chromosomal alterations that cause a phenotypic shift to immunologically unrecognizable forms. Analogous to genetic drift in Influenza A and B viruses, in the absence of the counterbalance of the immune recognition, the resultant immune-escape clones may have growth advantages that actuate metastasis (Alimonti et al., 2000a; Gabathuler et al., 1994). The gene expression profile in tumor tissue is influenced to a significant extent by the local microenvironment termed the connective tissue framework. This framework consists of normal cells, such as stromal fibroblasts, infiltrating immune cells, as well as extracellular matrix. It is now generally accepted that tumor-infiltrating immune cells, as well as cytokine-related signaling pathways, are intimately linked to the kinetics of tumor growth. The metastatic gene signature is a combination of genes acting together to define the malignant potential of a tumor. Complementation of expression of genes lost during immune-escape selection could render them immunologically recognizable and potentially halt immune-evasion of tumors (Alimonti et al., 2000a; Gabathuler et al., 1994).

There are several mechanisms for immune evasion in tumors including down regulation of expression of the major histocompatibility class I gene (MHC-I)/human leukocyte antigen (HLA) genes. The loss of HLA class I molecules is associated with tumor aggressiveness and metastatic potential. Several types of cancer, including breast, renal, melanoma, colorectal, head and neck squamous cell, cervical and prostate cancer show a correlation between HLA downregulation, poor prognosis and metastatic spread of the disease.

An important group of immune cells are innate lymphoid cells (ILCs) (Spits et al., 2013). The ILC family is a cytokine-producing group of cells phenotypically characterized by the absence of re-arranged antigen-specific receptors and the expression of stem cell antigen 1 (Sca1), lymphoid progenitor marker IL7Ra (CD127), IL2Ra (CD25), IL17BR (a subunit of IL25R), the IL-33 receptor T1/ST2 chain (Walker et al., 2013). ILCs are currently divided into three main groups, which are defined by the cytokines they produce (Lanier, 2013). Group 2 ILCs (ILC2), can produce type 2 cytokines (e.g. IL-5, IL-9, IL-13), and are considered to be innate helper cells (Neill et al., 2010; Roediger and Weninger, 2015). ILC2s respond to pro-allergenic cytokines such as IL-25 and IL-33 that are produced by epithelial cells in mucosal membranes (Martinez-Gonzalez et al., 2015). In addition, asthma-like symptoms mediated by ILC2s have been induced in mice that lack T and B cells using IL-33 alone (Nabe, 2014).

Group 3 ILCs are defined by their capacity to produce cytokines IL-17A and/or IL-22. They are important in facilitating responses to extracellular bacteria, with a particular role in mediating the balance between the intestinal immune system and the natural microbiome of the host.

Interleukin 33 (IL-33) is a cytokine belonging to the IL-1 superfamily (Cayrol and Girard, 2014; Gao et al., 2015; Guabiraba et al., 2014; Kearley et al., 2015; Martin, 2013; Musolino et al., 2014; Pascual-Figal and Januzzi, 2015). IL-33 is a dual-function protein that acts as a nuclear factor and pro-inflammatory cytokine. Nuclear localization and association with heterochromatin is mediated by the N-terminal domain and allows IL-33 to function as a novel transcriptional regulator of the p65 subunit of the NF-κB complex. The C-terminal domain is sufficient for binding to the ST2 receptor and activating the production of type 2 cytokines (e.g. IL-5 and IL-13) from polarized Th2 cells (Carriere et al., 2007) and ILC2 cells.

Interferon Induced Protein 44 (IFI44) is an IFN-alpha inducible protein which has previously been shown to have anti-proliferative activity in two human melanoma cell lines. (Hallen et al., 2007).

SUMMARY OF THE INVENTION

An object of the present invention is to provide modulation of cancer immunity with type 2 innate lymphoid cells and/or interleukin 33. In accordance with the present invention, there is provided a method for treating cancer and/or inhibiting cancer progression comprising administering a therapeutically effective amount of interleukin-33. In accordance with another aspect of the present invention, there is provided a method for treating cancer comprising increasing number of type 2 innate lymphoid cells (ILC2). In accordance with another aspect of the present invention, there is provided a method of treating cancer and/or inhibiting cancer progression comprising administering ILC2 cells. In accordance with another aspect of the present invention, there is provided a method of stimulating an immune response comprising administering interleukin 33 and/or type 2 innate lymphoid cells. In accordance with another aspect of the present invention, there is provided a method for treating cancer and/or inhibiting cancer progression comprising administering a therapeutically effective amount of IFI44. In accordance with another aspect of the present invention, there is provided a method of assessing cancer prognosis, the method comprising the step of monitoring interleukin-33 expression. In accordance with another aspect of the present invention, there is provided a method of determining prognosis, determining disease progression and/or predicting clinical outcome of cancer, said method comprising screening for the presence of eosinophils in/or surrounding a tumor.

BRIEF DESCRIPTION OF THE FIGURES

These and other features of the invention will become more apparent in the following detailed description in which reference is made to the appended drawings.

FIG. 3: IL-33 contributes to increased TAP-1 and H2-Kb expression and signaling in murine metastatic lung carcinoma clone A9 cells. a) RT-PCR analysis shows transient transfection of TAP deficient A9 cells with IL-33 genes restores TAP-1 gene expression. The positive control is TC1 cells (primary tumors), which express both TAP-1 and MHC-I. The negative controls are A9 cells alone and A9 cells transfected with vector alone. Levels of β-actin were used as loading controls. b) Western blot: Transient transfection of A9 cells with IL-33 gene restores TAP-1 and H2-Kb protein expression. A9 or TC1 cells were either transiently transfected with the pIRES2-EGFP vector alone or with the vector containing the IL-33 gene. Untransfected A9 cells were also treated with cytokines. Detection of mouse TAP-1 and H2-Kb was seen on a Western Blot using rabbit polyclonal anti-mouse TAP-1 or H2-Kb rabbit polyclonal antibody (anti-exon 8); Alexa Fluor 680 goat anti-rabbit was used as the secondary antibody. Lane 1 shows untreated A9 cells, Lane 2 shows A9 transfected with empty vector; Lane 3 shows A9 transfected with IL-33; Lane 4 shows A9 cells treated with IL-33 cytokine (50 ng/ml); Lane 5 shows A9 cells treated with IFN-γ cytokine (50 ng/ml); Lane 6 shows TC1 cells transfected with IL-33. Transient transfection of cells with the vector alone also upregulated TAP-1 and H2-Kb expression. Upregulation of TAP-1 and H2-Kb expression resulting from transfection with empty vector may be a result of an innate DNA-sensing mechanism. IL-33 cytokine added as protein also upregulated TAP-1 and H2-Kb expression. Addition of IL-33 protein avoids DNA-dependent innate immune signaling pathways. TC1 cell line transfected with the IL-33 gene also showed increased up-regulation of mTAP1 and H2-Kb expression. c) FACS analysis shows surface expression of MHC-I (H2-Kb) protein is increased in A9 cells upon transfection with the IL-33 gene. A9 cells were either transiently transfected with the pIRES2-EGFP vector alone (blue/second peak from left) or with the vector containing IL-33 (green). Cells were then stained with PE-conjugated anti-Kb mouse monoclonal antibody (mAb) (BD Harmingen, San Diego, Calif.) and analyzed on a FACScan cytometer. The amount of H2Kb expressed on the cell surface was also assessed. Untransfected A9 cells (grey/first peak from left) were used as a negative control, or as a positive control (red), while treated with IFN-γ.

Primers against H2-Kb, IL-33 and mTAP-1 were used to examine the resulting transcription levels of the genes in splenocytes of H2-Kb−/− mouse: Lane 1 shows splenocytes of H2-Kb−/−mouse; Lane 2 shows untreated TC1 cells; β-actin was used as loading control.

Figure 7:
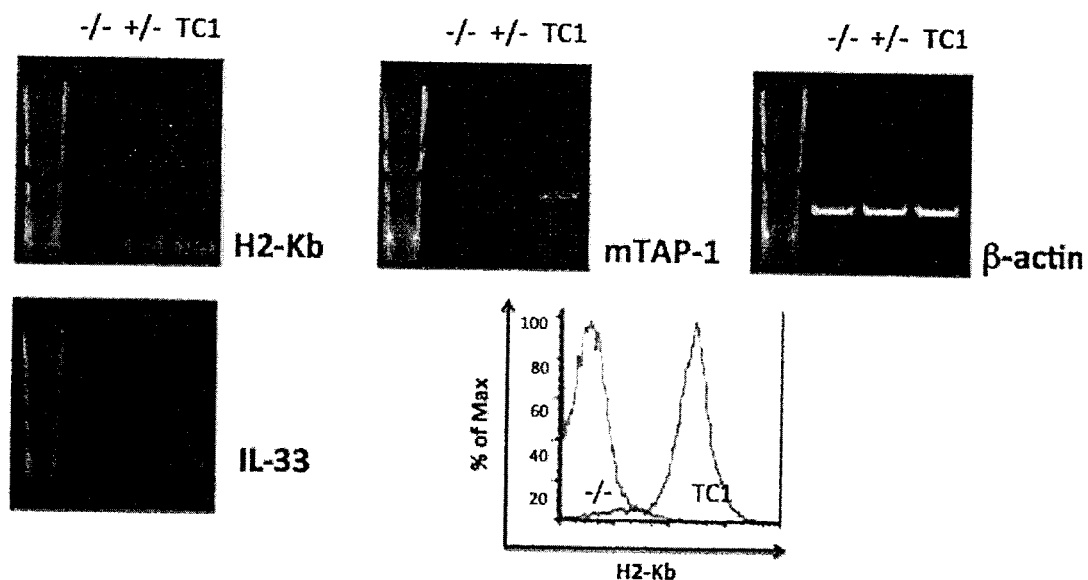

FIG. 7: Down regulation of H2-Kb decreased IL-33 gene expression in splenocytes of H2-Kb−/− mice. There appears to be incremental effects of down regulation of H2-Kb on Tap1 expression, but the expression of IL-33 appears to require a threshold expression of MHC-I.

FIG. 8: Metastatic cells possess a mutation in the IL-33 promoter-enhancer regions leading to loss of heterozygosity (LOH). A single base pair mutation A114G on IL-33 promoter of metastatic A9 cell within a GATA binding area affected one IL-33 allele and led to loss of heterozygosity (LOH), as well loss of three GATA transcription factors. The database of the Computational Biology Research Center was used.

Figure 9:
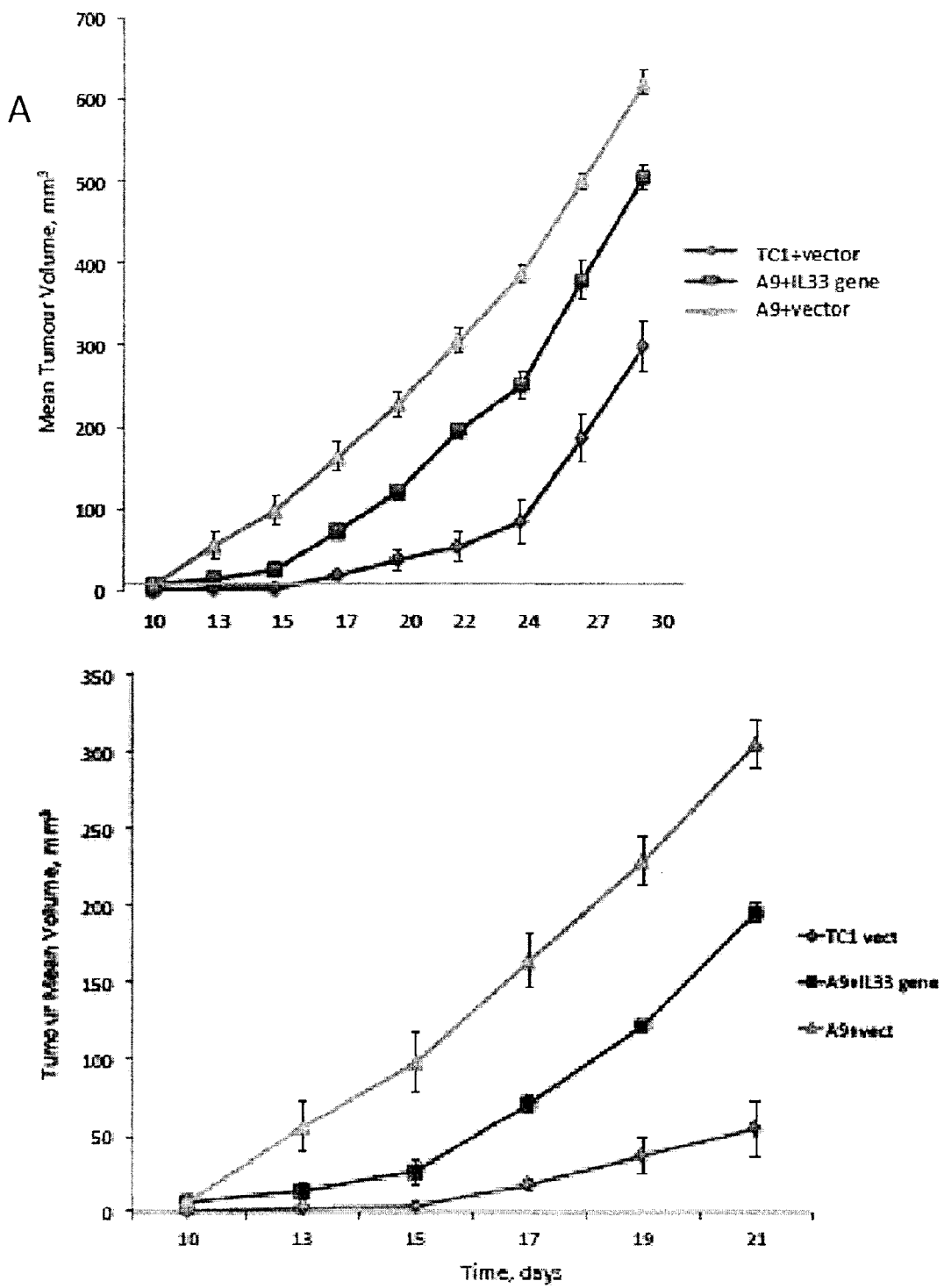
Figure 9B:
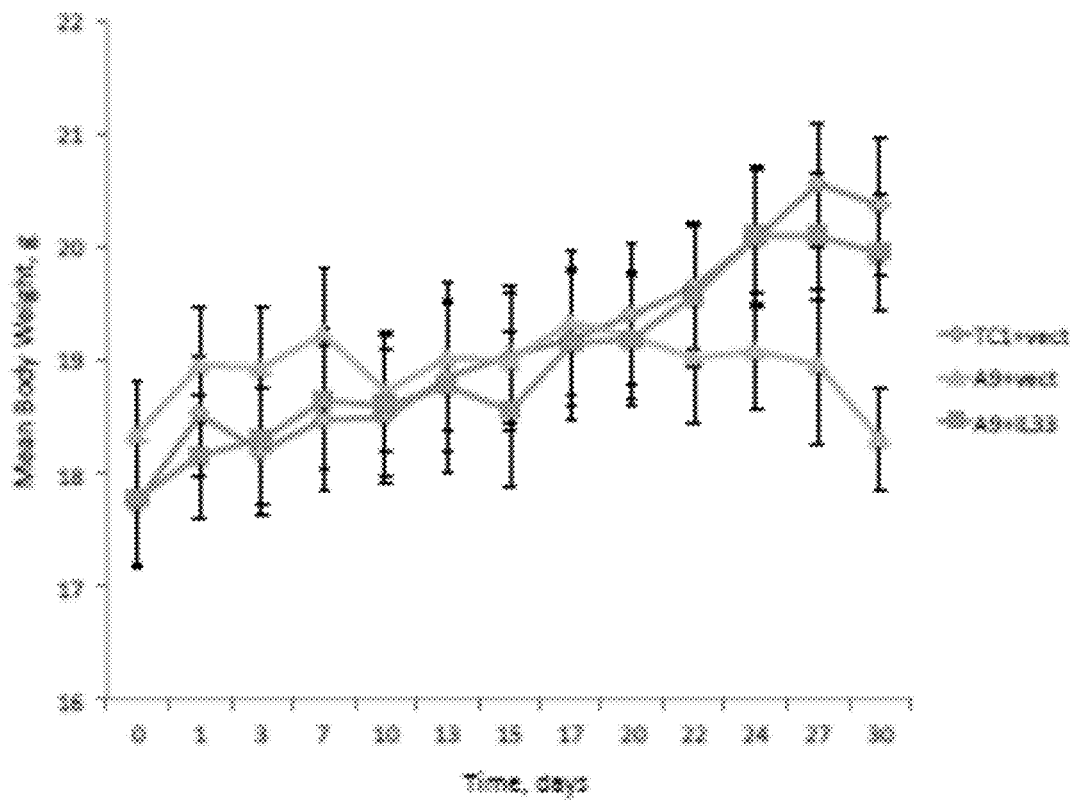

FIG. 9—IL-33 gene-complementation can alter the clinical manifestations of the disease in terms of severity of signs and symptoms and rate of progression. Stable transfection of IL-33 gene into A9 cells (A) suppresses tumor growth rate and (B) maintains animal body weight in vivo.

Figure 10:
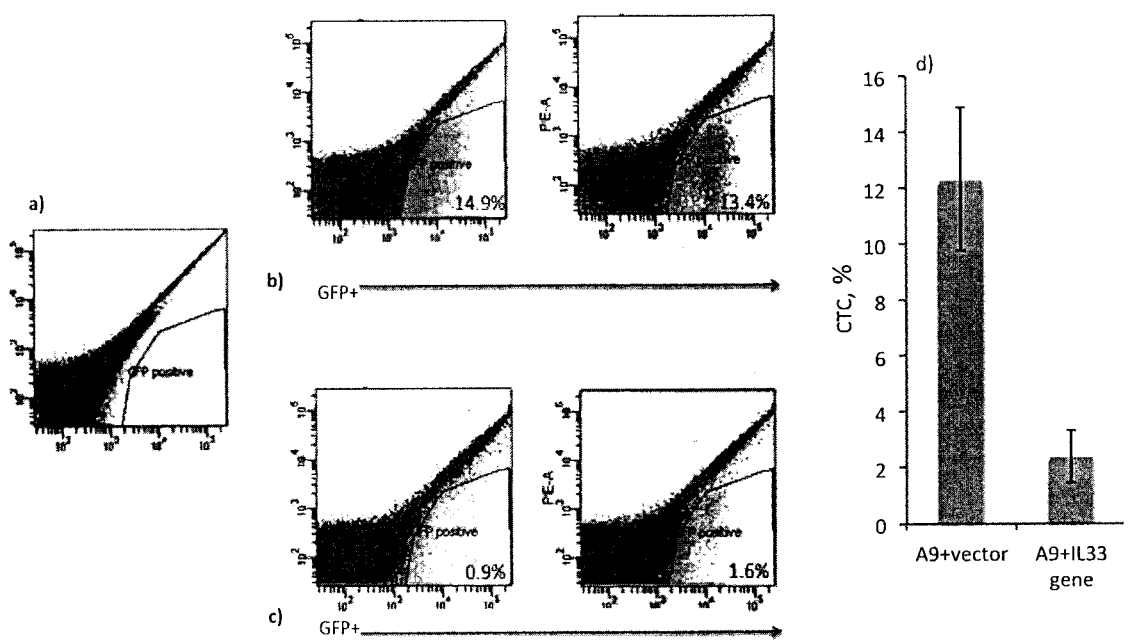

FIG. 10: IL-33 gene-complementation inhibits metastatic spread of tumor cells to adrenal glands in a mouse model. GFP-positive circulating tumor cells were isolated from adrenal glands that were distal from initial subcutaneous inoculation, and assessed using Flow Cytometry. Shown here are representative results isolated from the following groups: a) Control animal with no tumor; b) Animals injected with [A9+vector]; c) Animals injected with [A9+ IL-33 gene]; d) Quantification of GFP-positive circulating tumor cells in band c. Each graph represents the data from one animal.

Figure 11:
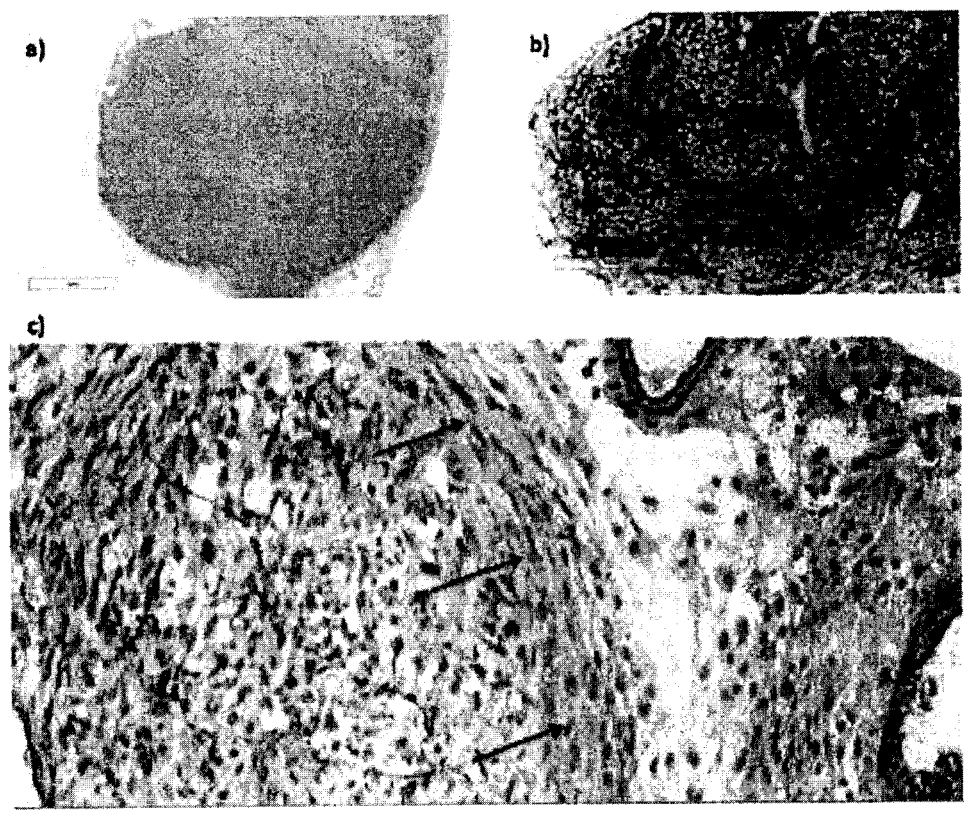

FIG. 11: Tumor morphology. Histopathology examination of the resected tumors, showing (a) malignant cells with a smaller cytoplasmic content and a higher nucleus/cytoplasm ratio, forming dense, uniformly distributed, solid architecture, (b) Distribution of primary tumors amongst adjacent tissues. Panel c) demonstrates that primary tumors were enclosed by a well-defined fibrous capsule.

Figure 12:
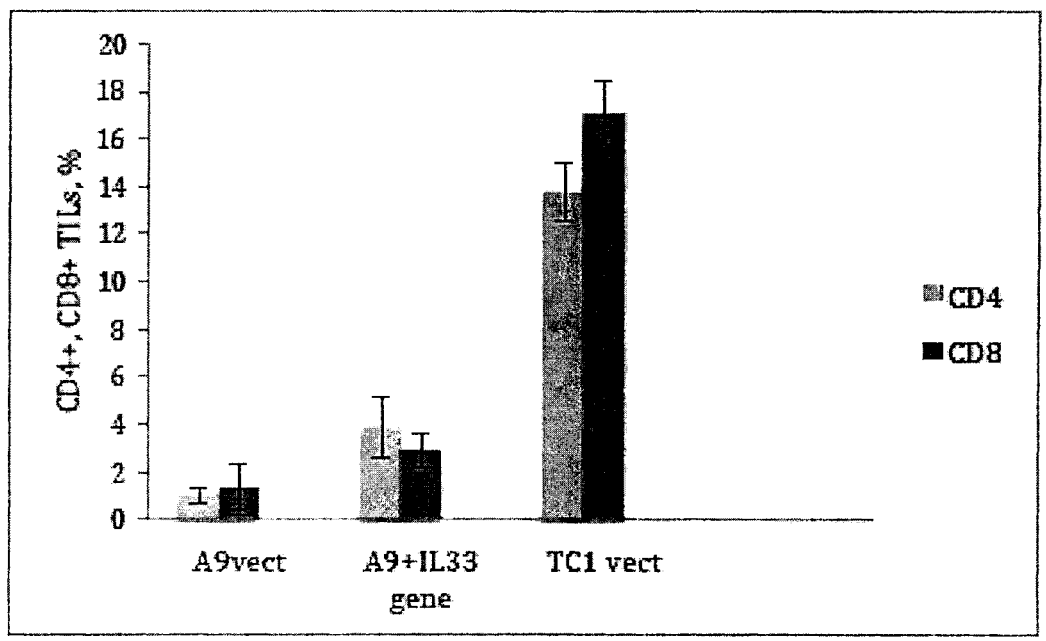

FIG. 12: IL-33 gene expression induced an increase in the number of tumor infiltrating lymphocytes (TILs). Flow cytometry was used to innumerate the TILs that were isolated from resected tumors. More TILs were found present in tumors that expressed IL-33, which includes both A9+IL-33 and the primary tumor, TC1.

Figure 13:
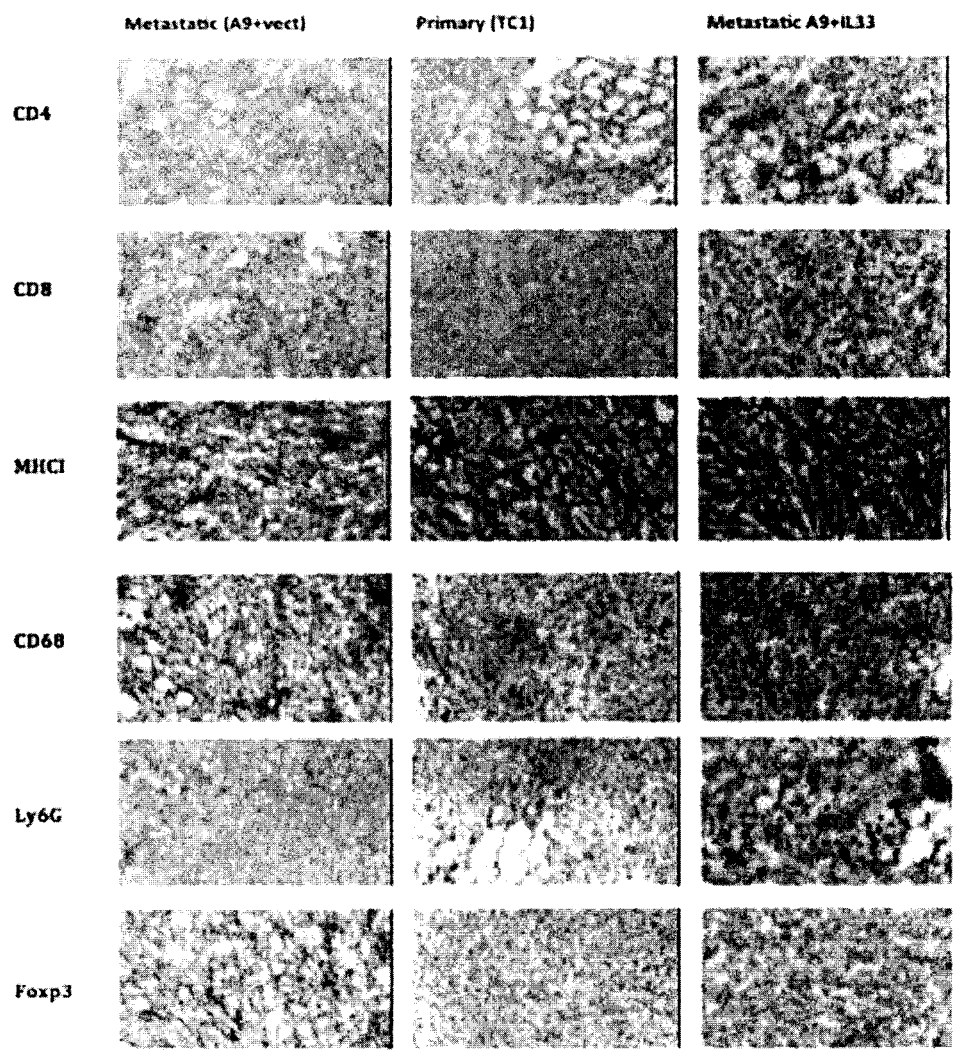

FIG. 13: Immunohistochemical staining for tumor-infiltrating lymphocytes and other targets (CD4, CDS, MHC-I, CD68, Ly6G, Foxp3) in metastatic (A9+vect), primary (TC1) and genetically complemented metastatic (A9+IL-33) tumors. Genetic complementation of immune evasive tumor results in a phenotypic shift towards immune recognition. 10 μm thick sections were stained with appropriate antibodies and imaged at 20× magnification.

Figure 14:
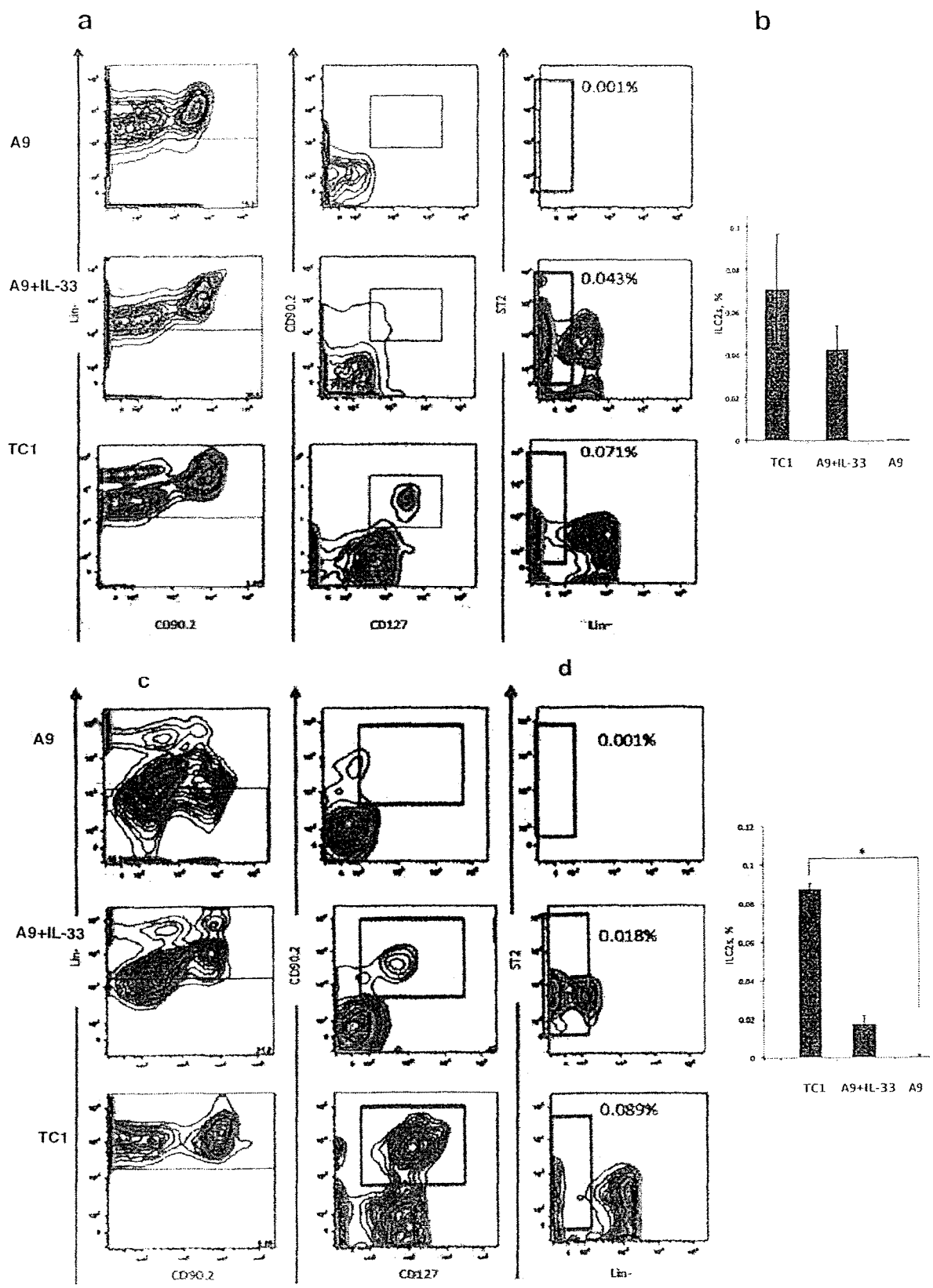

FIG. 14: The frequency of ILC2s is elevated in animal bearing primary tumors and metastatic tumors stably transfected with IL-33 gene. ILC2s isolated from disaggregated lymph nodes and tumor tissues were analyzed by flow cytometry as Lin.ST2+CD127$^+$CD90.2$^+$ cells. Gating strategy included first gating on lineage-negative (Lin$^−$) and (CD90.2)-positive leukocytes and further analyzing for ST2$^+$ and CD127$^+$ expression: a) Stained ILCs isolated from lymph nodes; b) Quantification of the ILC2s isolated from lymph nodes. The ranges represent the data comparing eight different animals in each treatment group. c) Stained ILCs isolated from tumors; d) Quantification of the ILC2s isolated from tumors. The ranges represent the data comparing four different animals in each treatment group; *P<0.05 compared with ILC2 cells isolated from the primary [TC1+ vector] and metastatic [A9+vector] tumors (Student's t-test).

Figure 15:
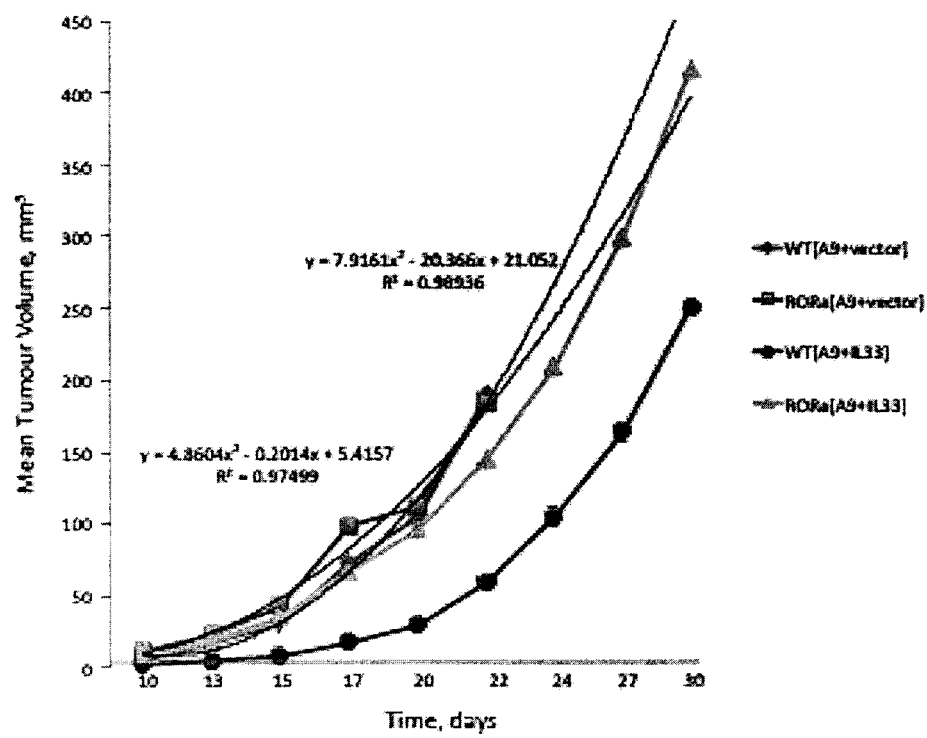

FIG. 15: Tumor growth rate on chimeric mice. Stable transfection of IL-33 gene into A9 cells resulted in significantly inhibited tumor formation in wild type mice when compared to RORα−/− chimeras.

Figure 16:
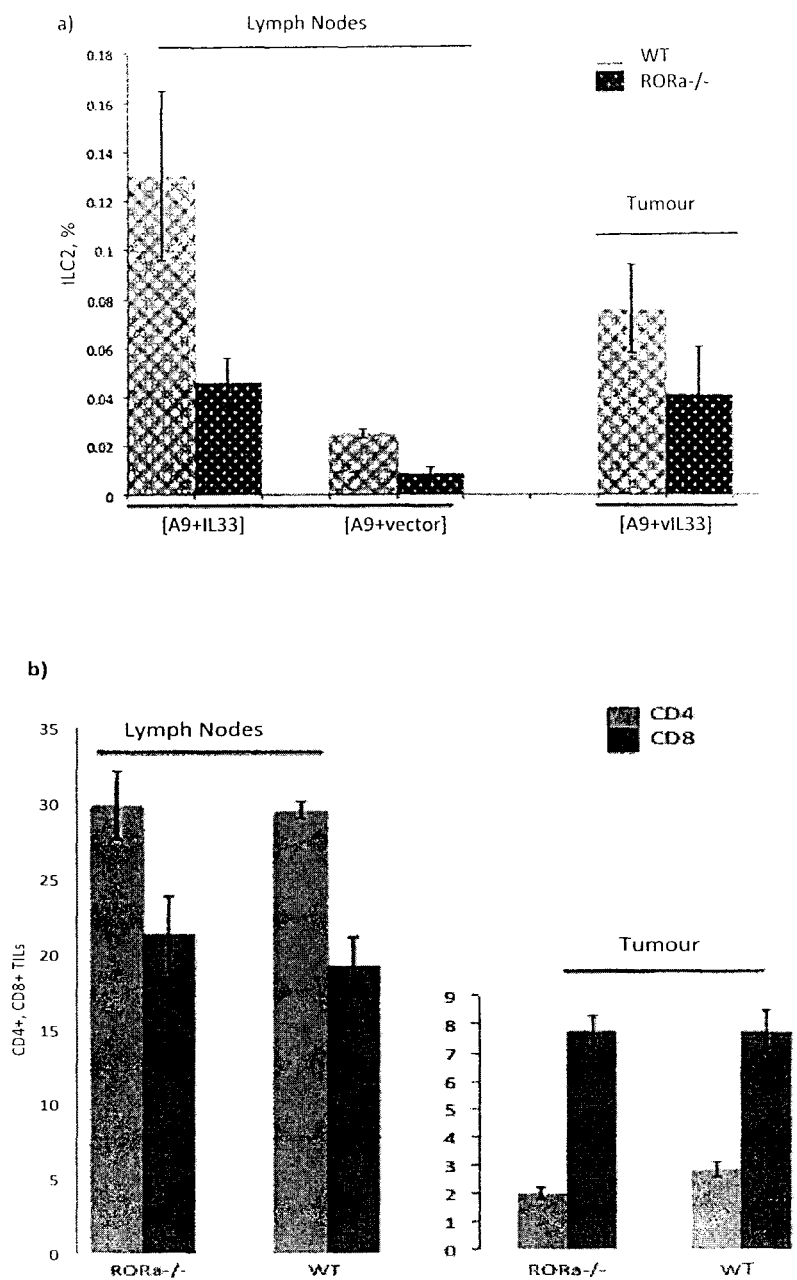

FIG. 16: Innate lymphocytes involvement in anti-tumor immune response is higher during the early stages of tumor development. Mice were transplanted with either RORα−/− or wild type bone marrow, and after successful bone marrow repopulation, metastatic tumors expressing IL-33 [A9+IL-33] were injected into these chimeric mice. a) At week 3 after establishment of the tumor, the numbers of ILC2 cells found in neighboring lymph nodes were significantly lower in RORα−/− mice compared to wild type chimeras. By week 4, the numbers of ILC2 cells dropped in both RORα−/− and wild type mice. b) RORα deficiency had no effect on the ratio of CD4/CD8 lymphocytes.

Figure 17:
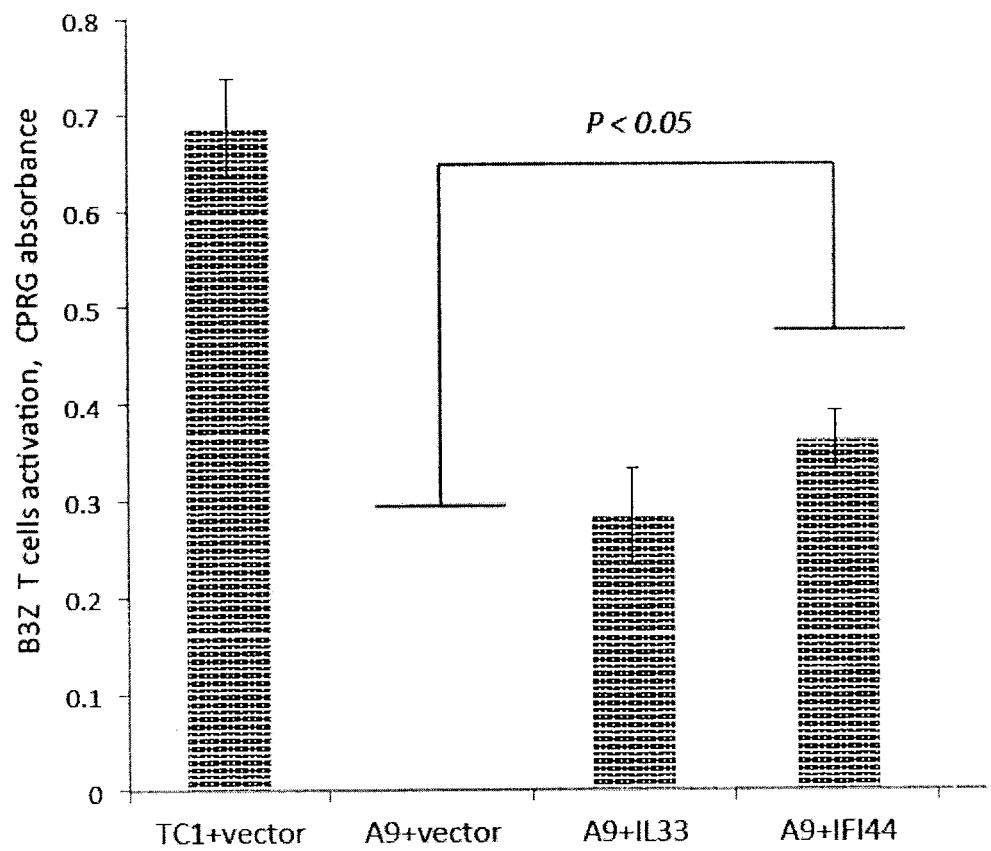

FIG. 17: IL-33 and IFI44 (Interferon Induced Protein 44) complements immune recognition of metastatic tumors. The expression of the IFI44 gene within metastatic murine lung carcinoma cells (A9) enhanced antigen-specific recognition by B3Z T-cells to a higher level compared to IL-33 gene. [TC1+vector] cell line was used as a positive control.

Figure 18:
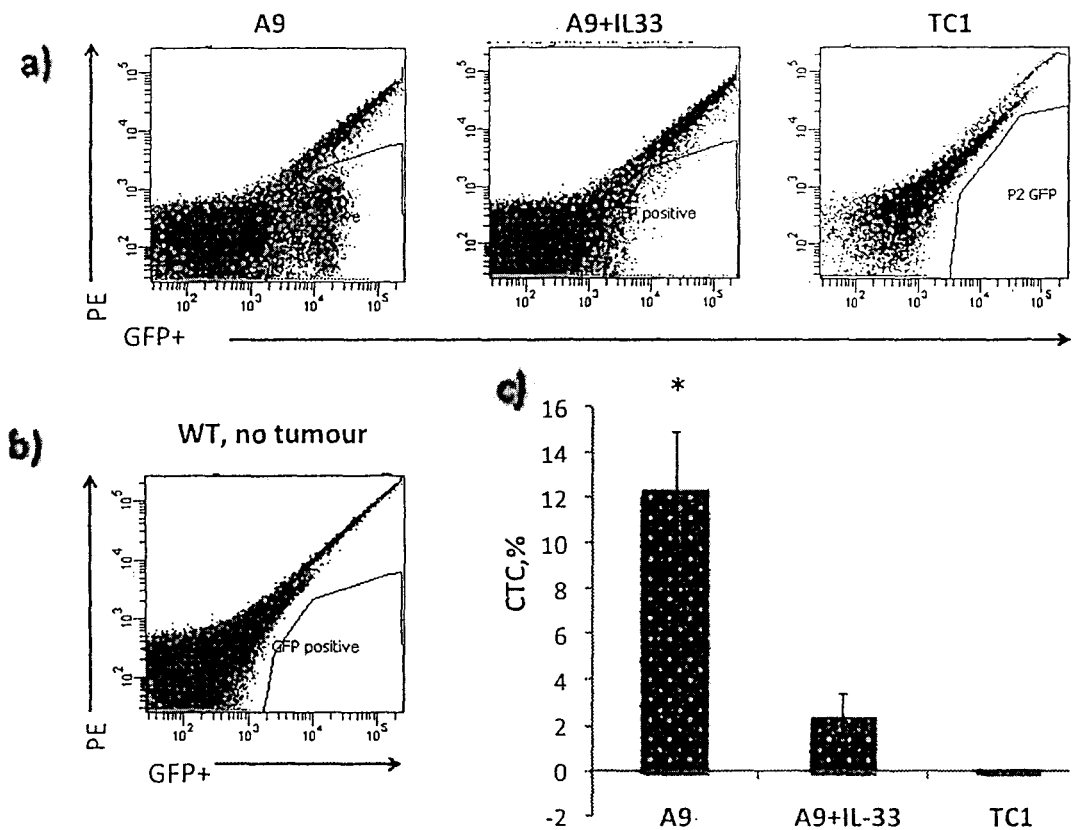

FIG. 18: IL-33 gene-complementation inhibits metastatic spread of tumor cells to adrenal glands in a mouse model: GFP-positive circulating tumor cells were isolated from adrenal glands that were distal from initial subcutaneous inoculation, and assessed using Flow Cytometry. Shown here are representative results isolated from the following groups: a) Animals injected with [A9+vector]; Animals injected with [A9+1L-33gene]; Animals injected with [TC1+vector); b) Control animal with no tumor; c) Quantification of GFP-positive circulating tumor cells in a). The graph represents the data of CTC detected in adrenal glands collected individually from eight animals in each group. *P<0.05 when compared with CTCs isolated from adrenal glands of animals bearing the metastatic [A9+vector] tumor with the primary [TC1+vector) or genetically complemented [A9+IL-33] ones.

Figure 19:
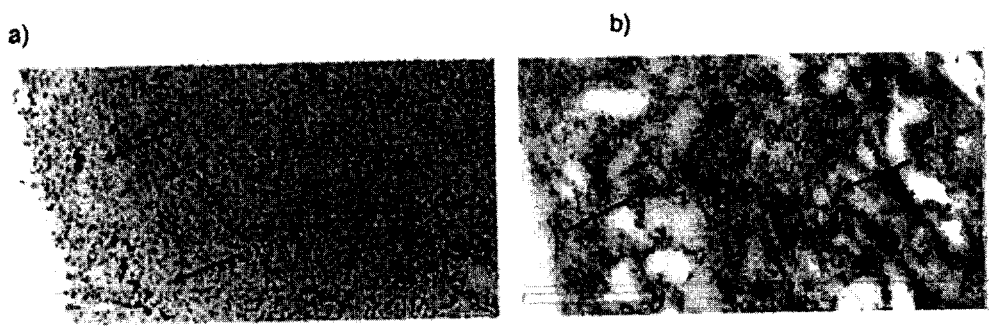

FIG. 19: Involvement of eosinophils in anti-tumor inflammatory response. Genetic complementation of immune evasive tumor shows shift towards up-regulation of the anti-tumor inflammatory response. The release of factors brought on by IL-33 expression modified the microenvironment and allowed eosinophils to flow through the tissue when compared to metastatic untreated tumor. 10 μm thick sections were stained with Giemsa and imaged at 20× magnification. a) Two focal areas of eosinophils accumulations within the normal tissue adjacent to the periphery of the malignant tumor; b) Eosinophils flow through the tissue of IL-33 expressing metastatic tumor.

Bar=200 μm

Figure 20:
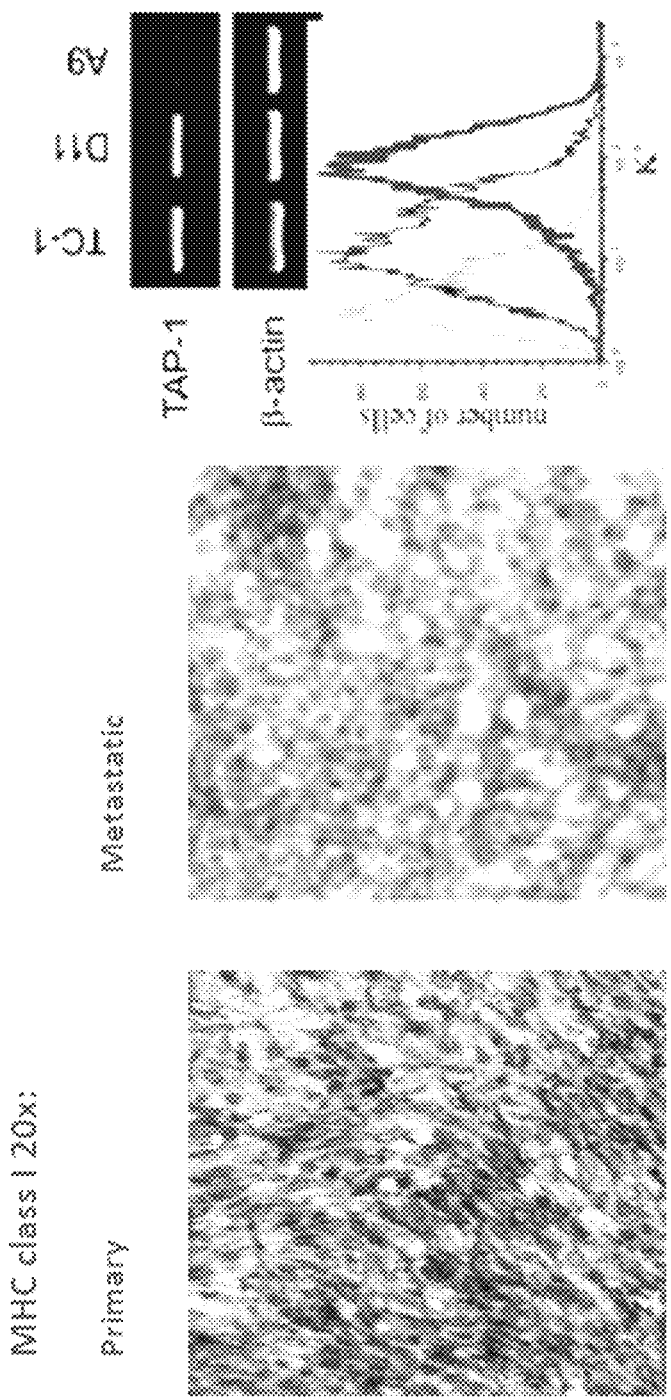

FIG. 20: A comparison of immune responsible and immune evasive tumor models.

FIG. 21: A gene ontology analysis comparing metastic and non-metastatic cell lines. This program groups different genes based on their biological properties, cell composition, functions. 10 groups of gene products in mouse genome were significantly different between metastatic and non-metastatic cell lines including genes involved in extracellular matrix remodelling and genes involved in immune response.

Figure 22:
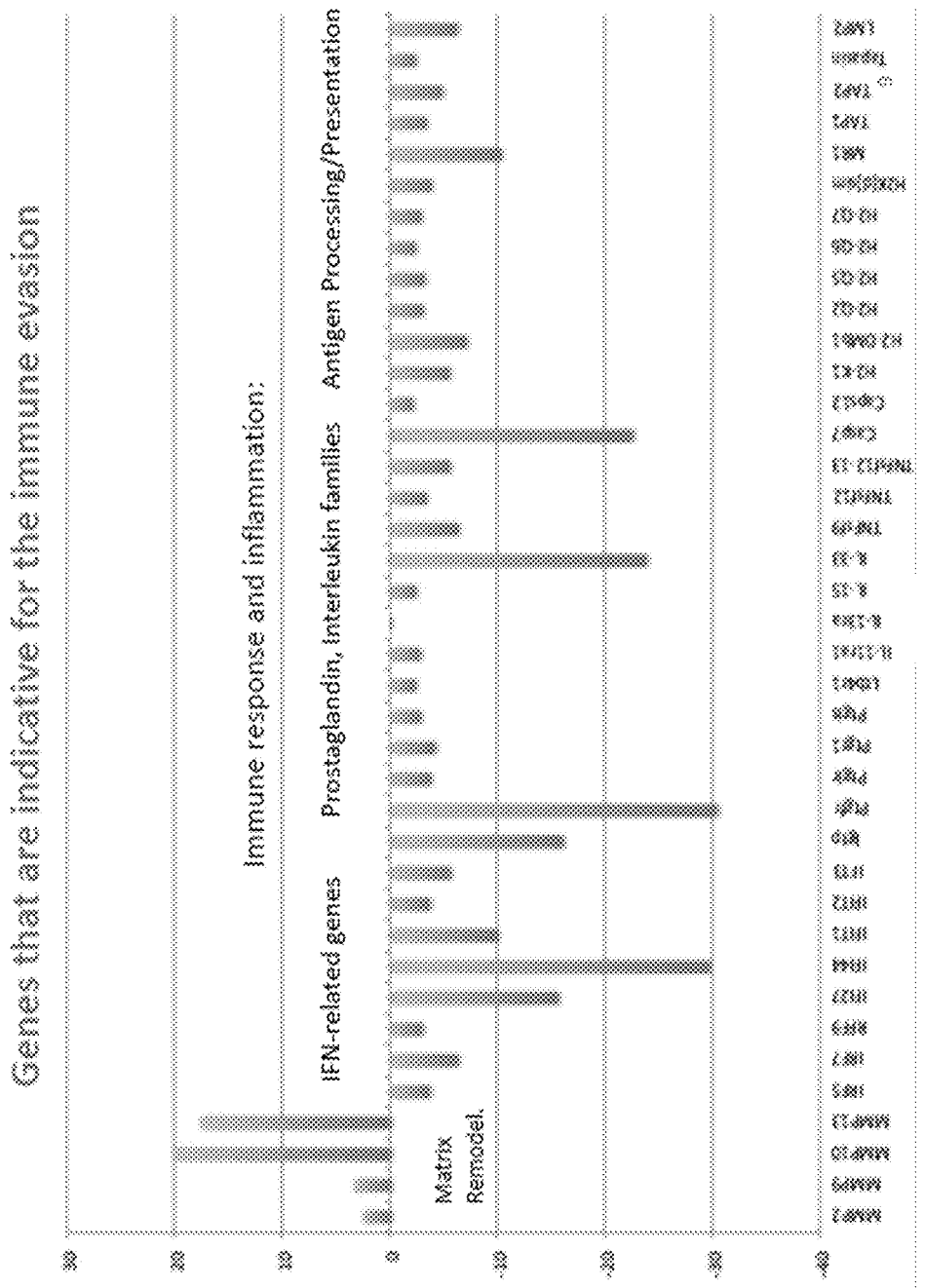

FIG. 22: Genes that are indicative for the immune evasion

Figure 23:
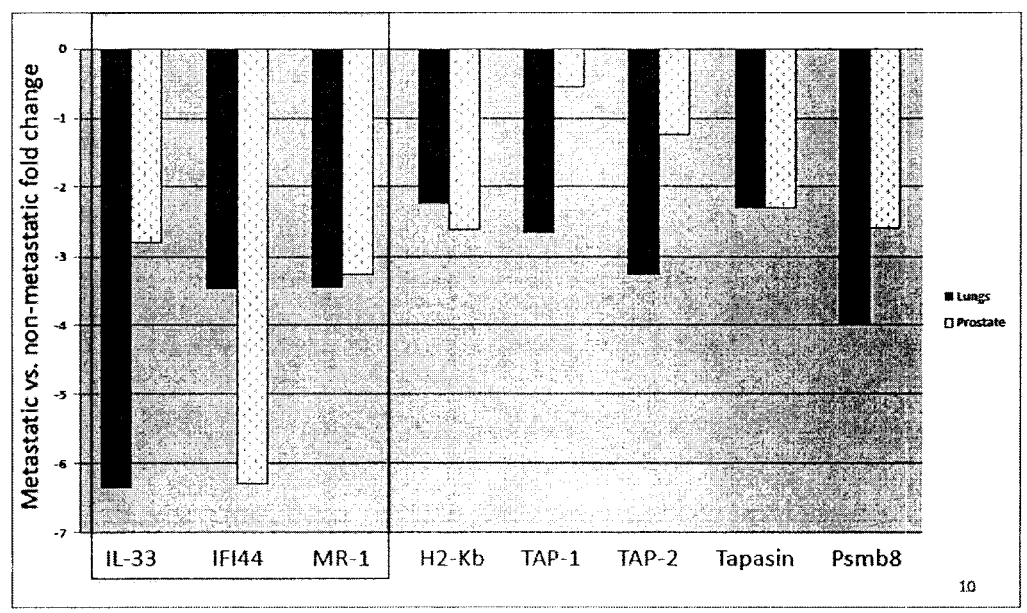

FIG. 23: IL-33, IFI44 and various antigen presenting protein (APP) genes are down regulated in murine metastatic lung and prostate carcinomas.

FIG. 24: MR1—non-peptide presenting molecule.

Figure 25:
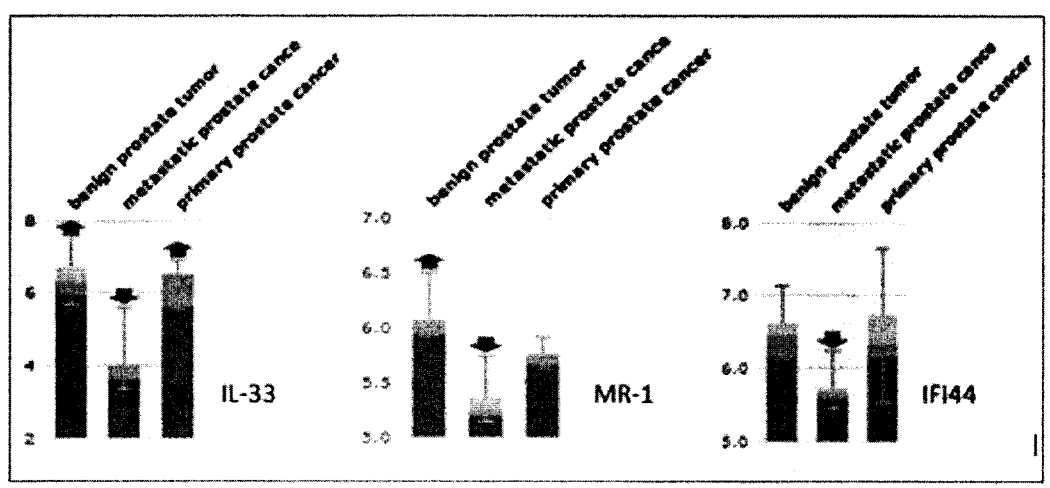

FIG. 25: IL-33, MR1 and IFI44 are down regulated in human metastatic prostate cancer.

Figure 26:
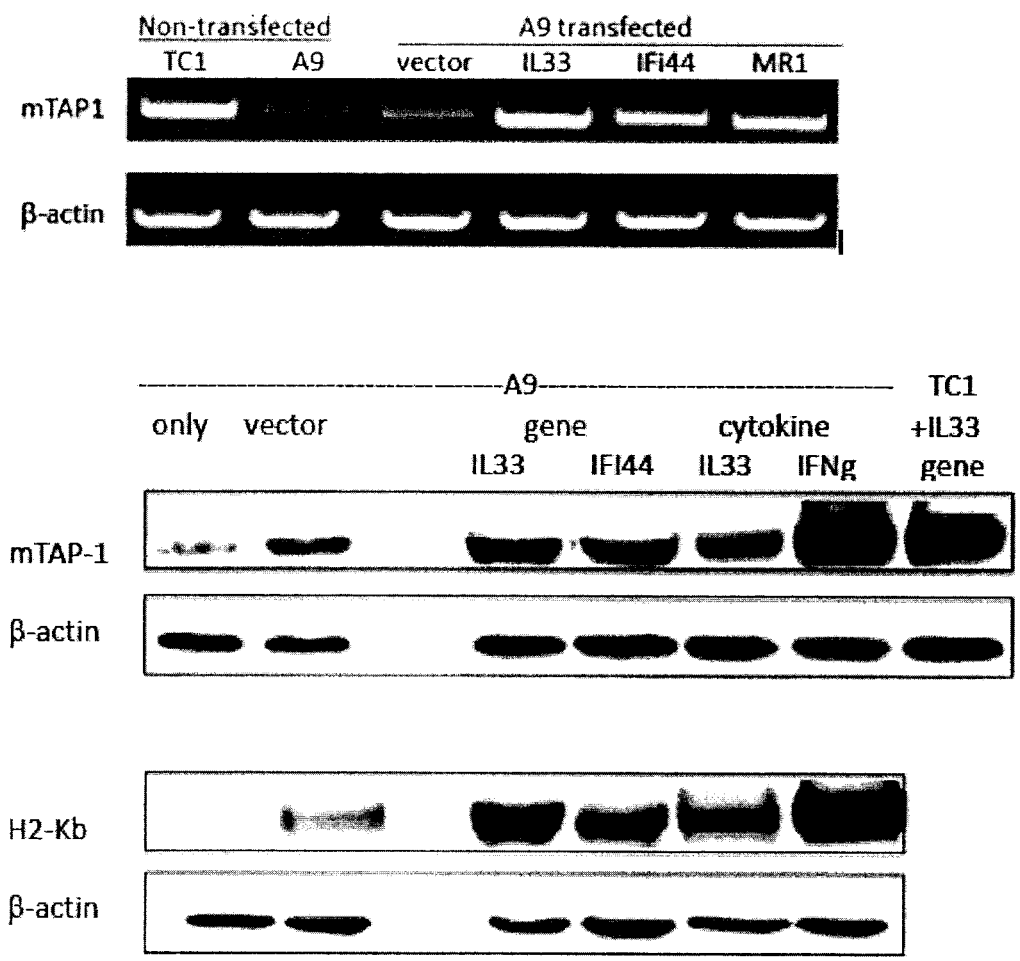

FIG. 26: IL-33, IFI44 genes contribute to increased TAP-1 and H2-Kb expression/signaling in the MHC-loss A9 murine lung carcinoma cells.

Figure 27:
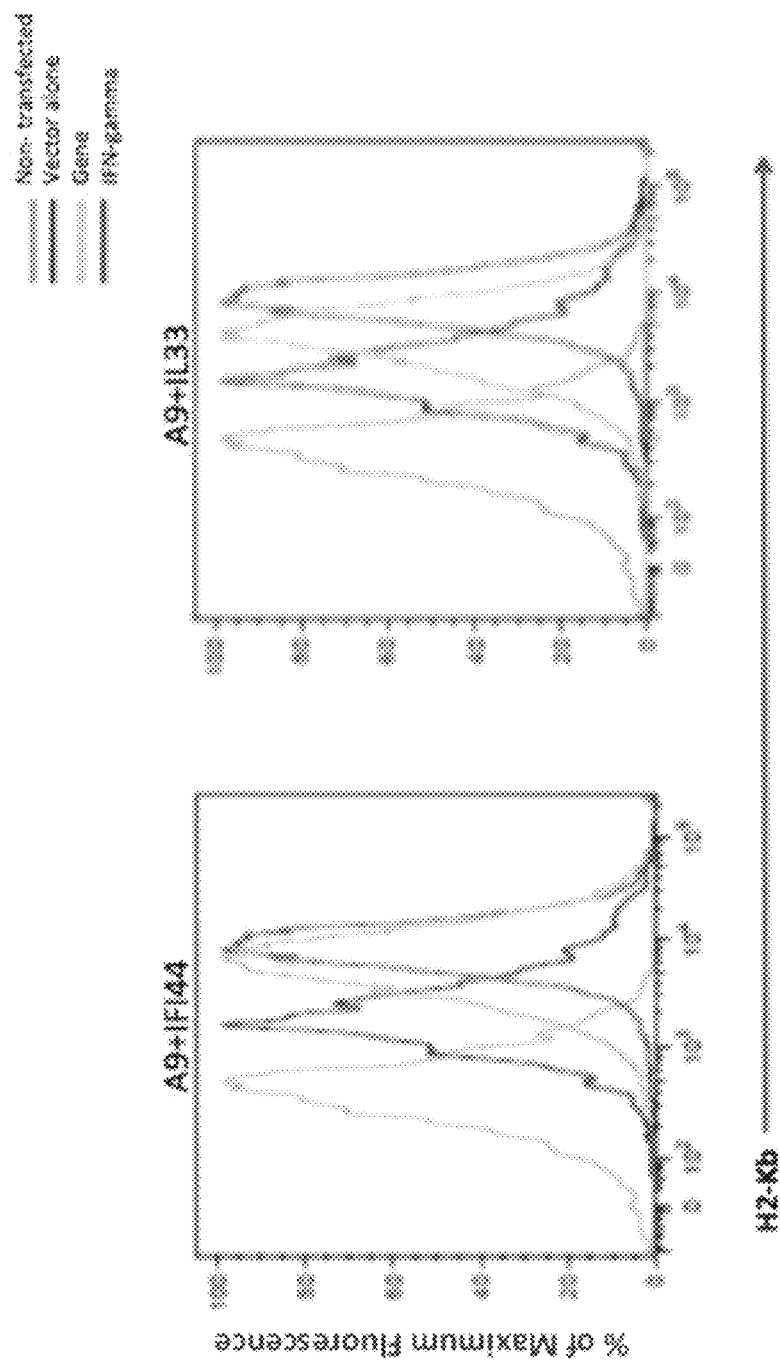

FIG. 27: IL-33, IFI44 genes contribute to increased TAP-1 and H2-Kb expression/signaling in the MHC-loss A9 murine lung carcinoma cells.

Figure 28:
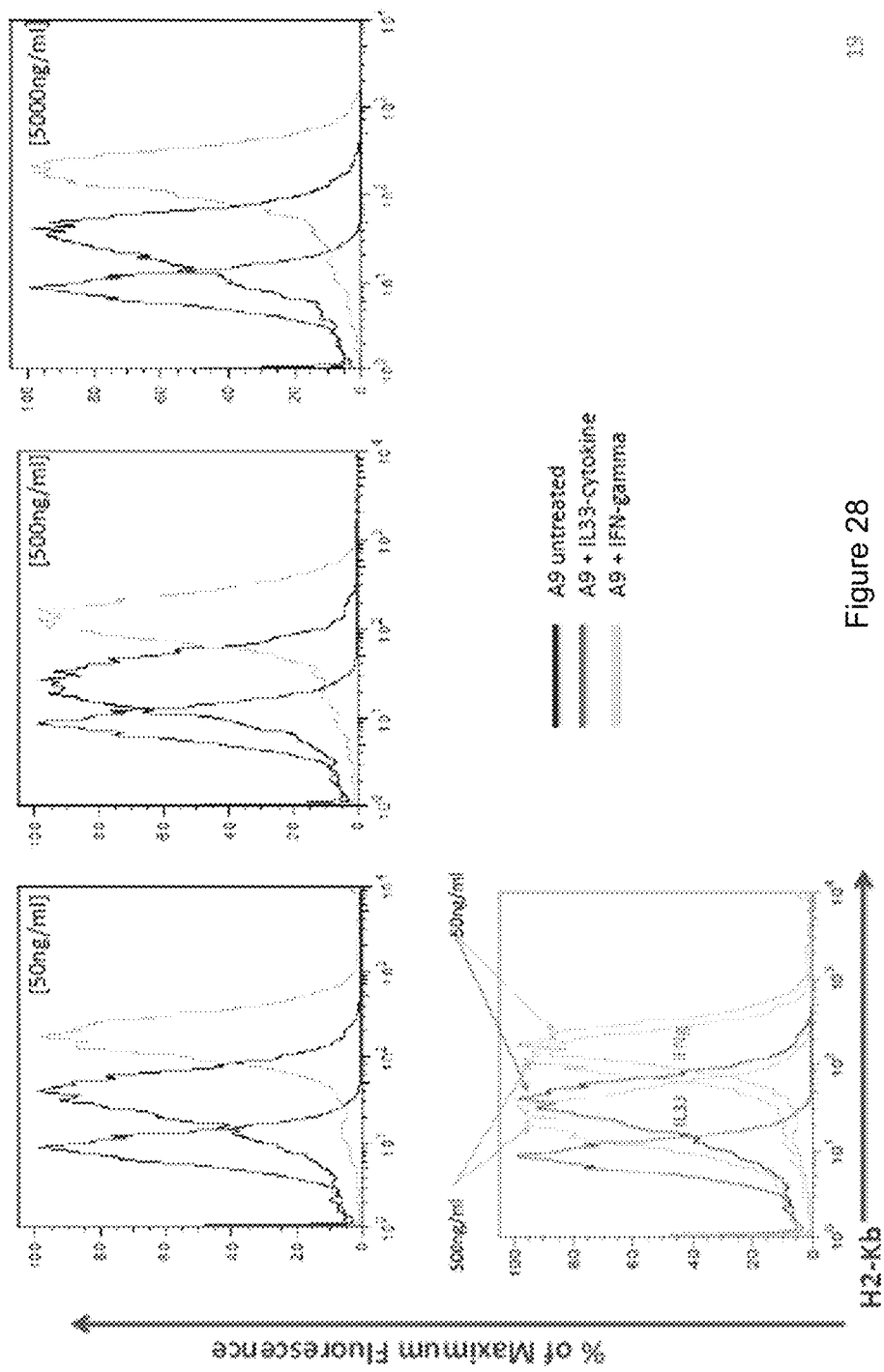

FIG. 28: IL-33-cytokine contributes to increased H2-Kb expression/signaling in the MHC-loss A9 murine lung carcinoma cells.

Figure 29:
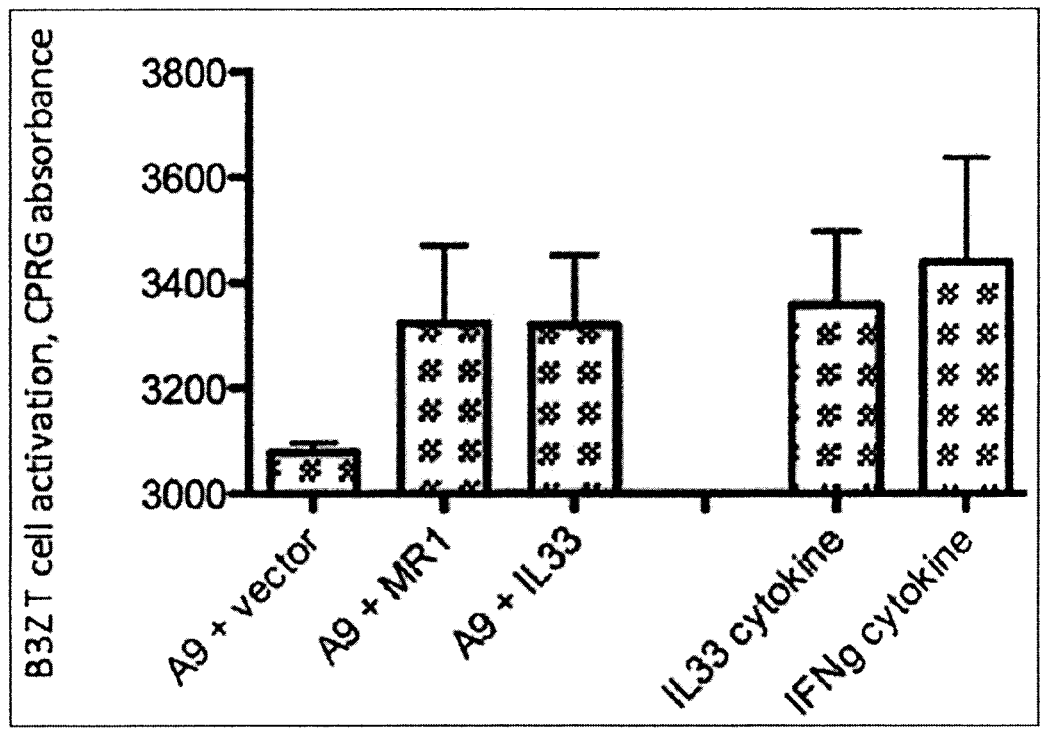

FIG. 29: IL-33, MR-1 contributed to increased H2-Kb expression/signaling in the MHC-loss A9 murine lung carcinoma cells.

Figure 30:
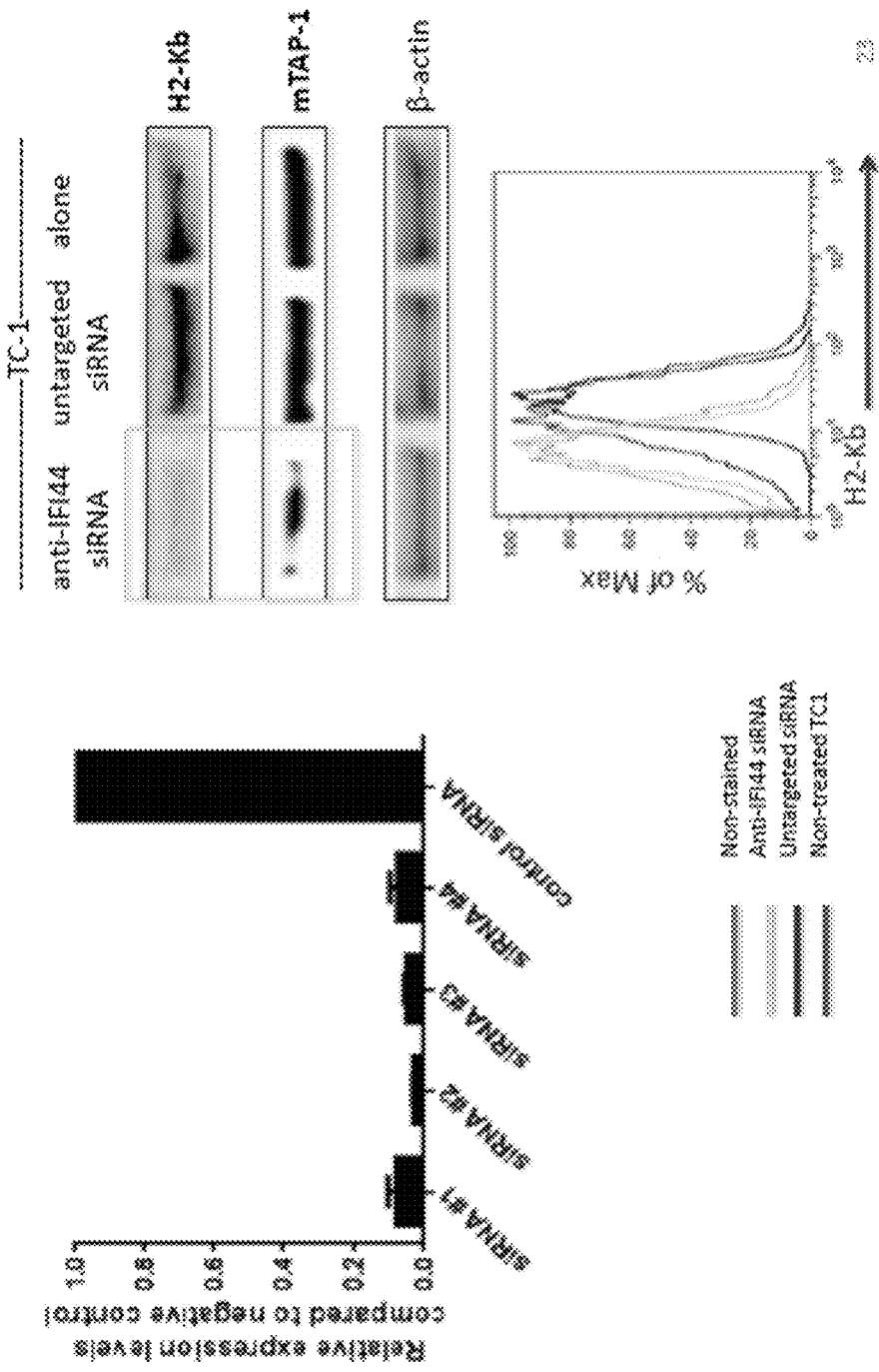

FIG. 30: Down regulation of IFI44 decreased H2-Kb expression.

Figure 31:
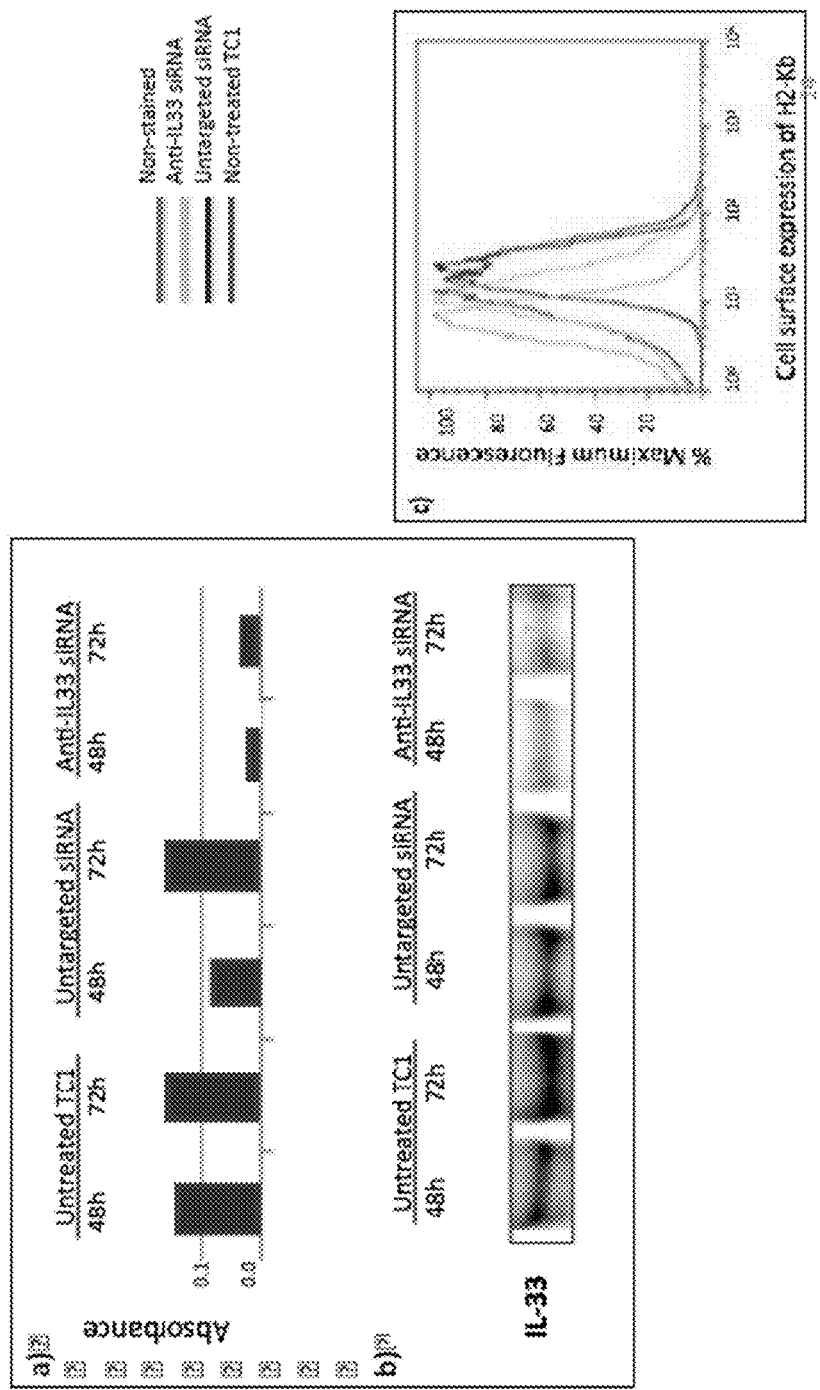

FIG. 31: Down regulation of IL-33 decreased H2-Kb expression.

FIG. 32: Down regulation of IL-33, MR-1 and IFI44 decreased H2-Kb surface expression.

Figure 33:
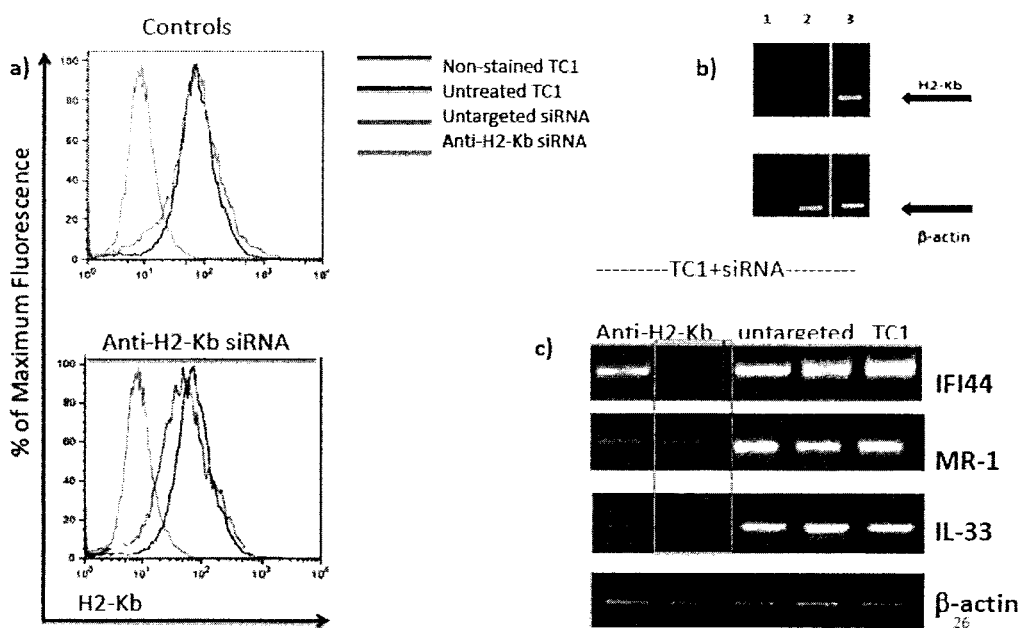

FIG. 33: Down regulation of H2-Kb decreased selected gene-candidates expression. A) Flow cytometry of H2-KB expression in controls and Anti-H2-kb siRNA in Non-Stained TC1 tumors, untreated TC1 tumors, untargeted siRNA, and Anti-H2-kb siRNA. B) H2-kb expression and c) down regulation of H2-Kb decreases selected gene-candidate expression.

Figure 34:
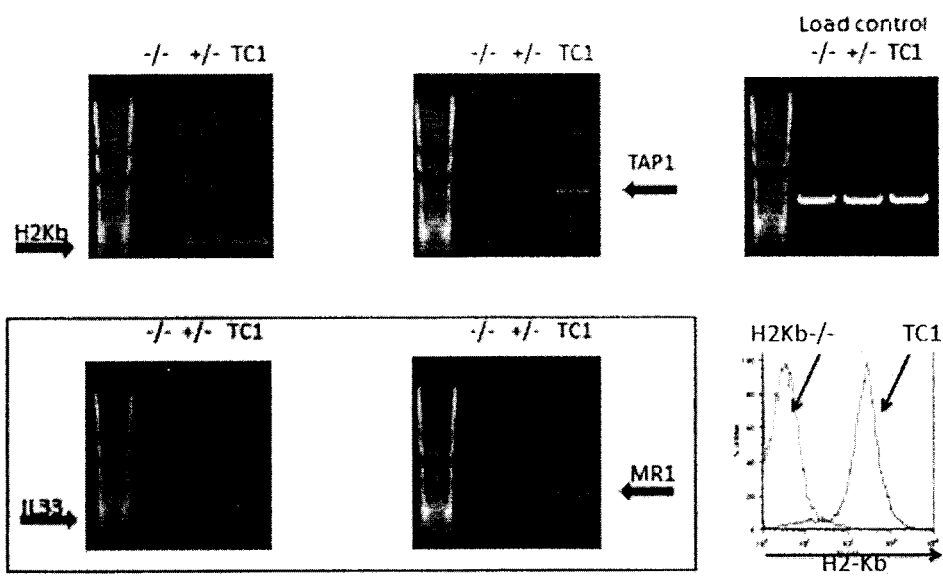

FIG. 34: Down regulation of H2-Kb appears to decrease selected gene-candidates expression in splenocytes of H2-Kb−/− mouse.

FIG. 35: siRNA targeted against IFI44 in TC-1 cells downregulated MR-1 gene expression.

Figure 36:
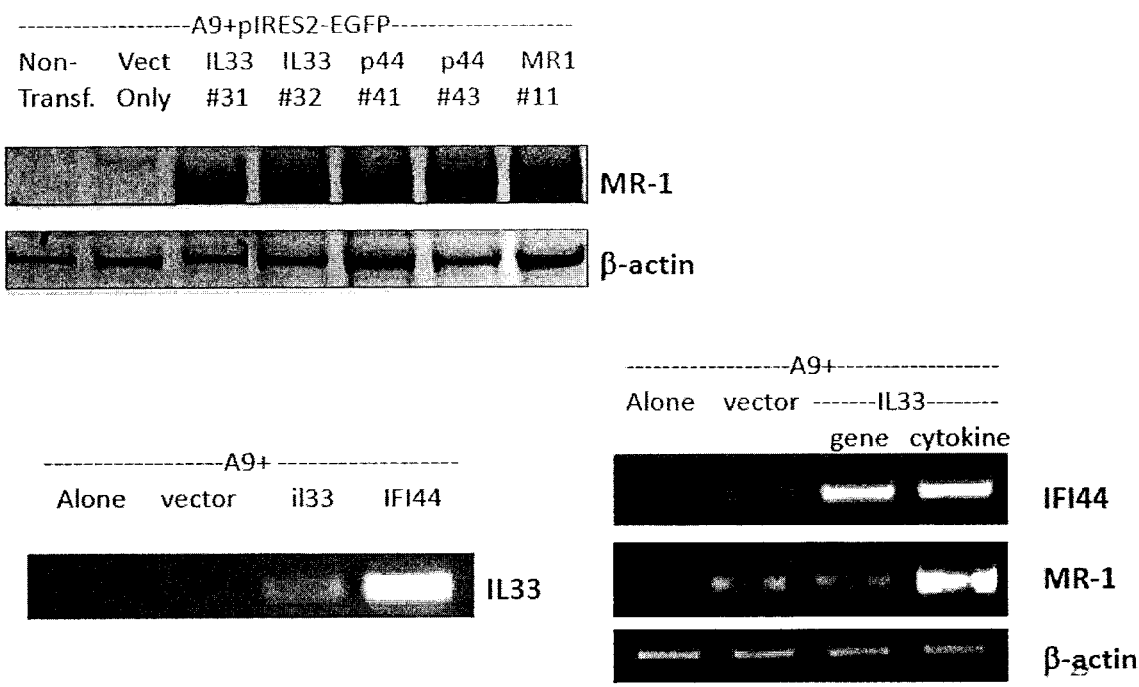

FIG. 36: MR1-protein expression was up regulated in all A9 clones stably transfected with gene-candidates.

Figure 37:
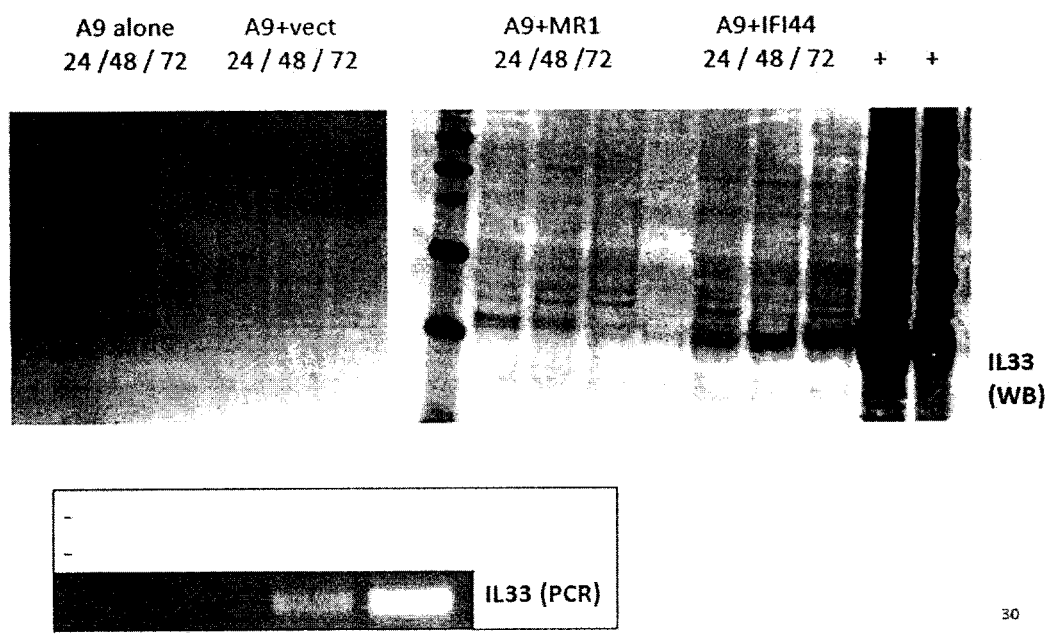

FIG. 37: IFI44 up regulated IL-33 protein production by A9 cells.

Figure 38:
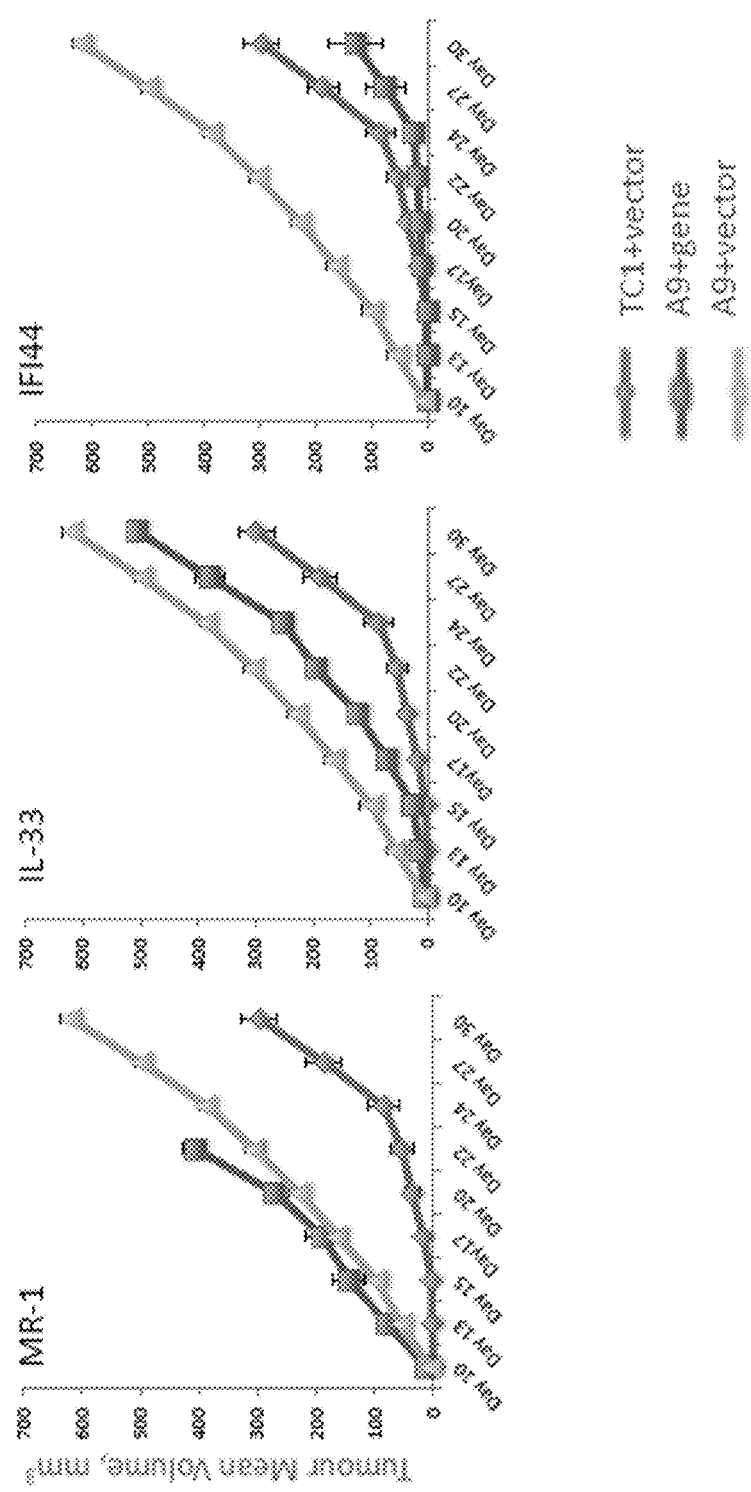

FIG. 38: IFI44 and IL-33 gene expression induced suppression of tumor growth rate in vivo.

Figure 39:
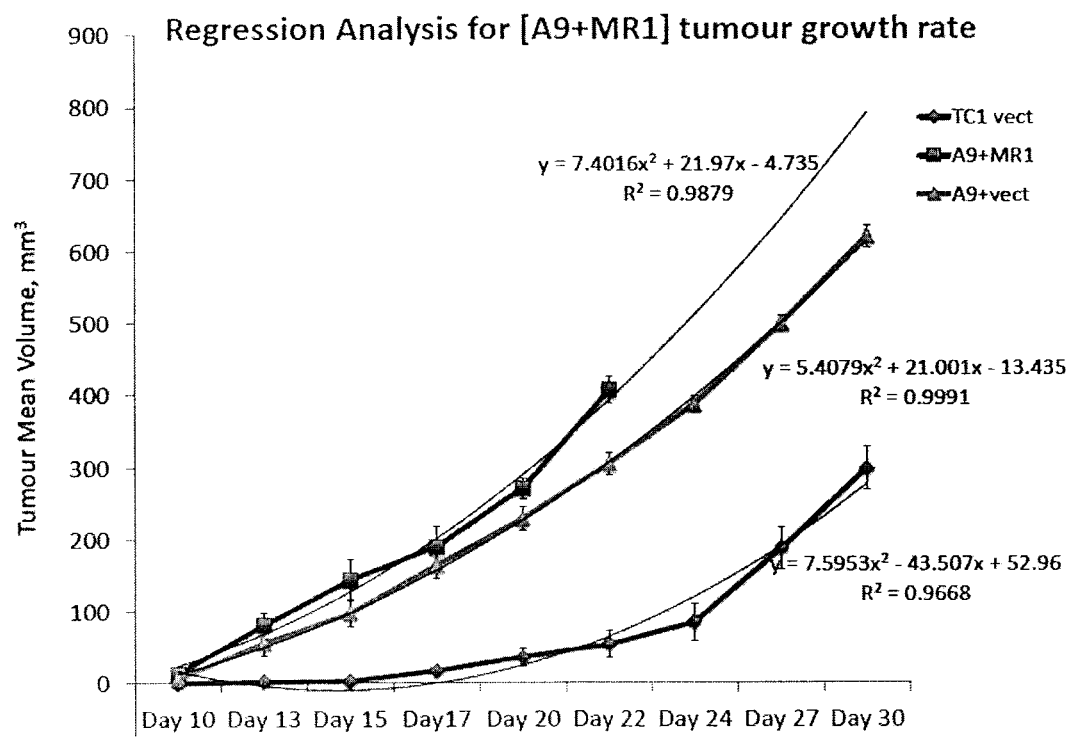

FIG. 39: Regression Analysis for [A9+MR1] tumor growth rate.

Figure 40:
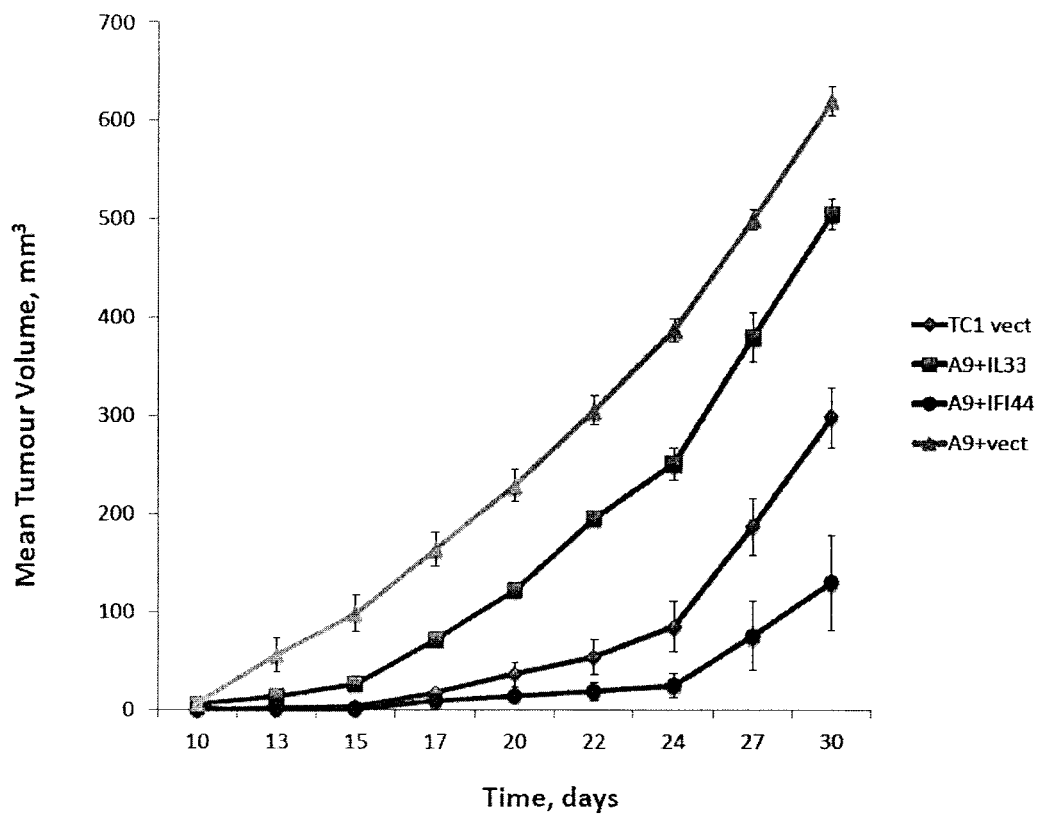

FIG. 40: IL-33 or IFI44 gene-complementation can alter the clinical manifestations of the disease in terms of severity of signs and symptoms and rate of progression. In particular, stable transfection of IL-33 or IFI44-gene into A9 cells suppresses tumor growth rate in vivo.

Figure 41:
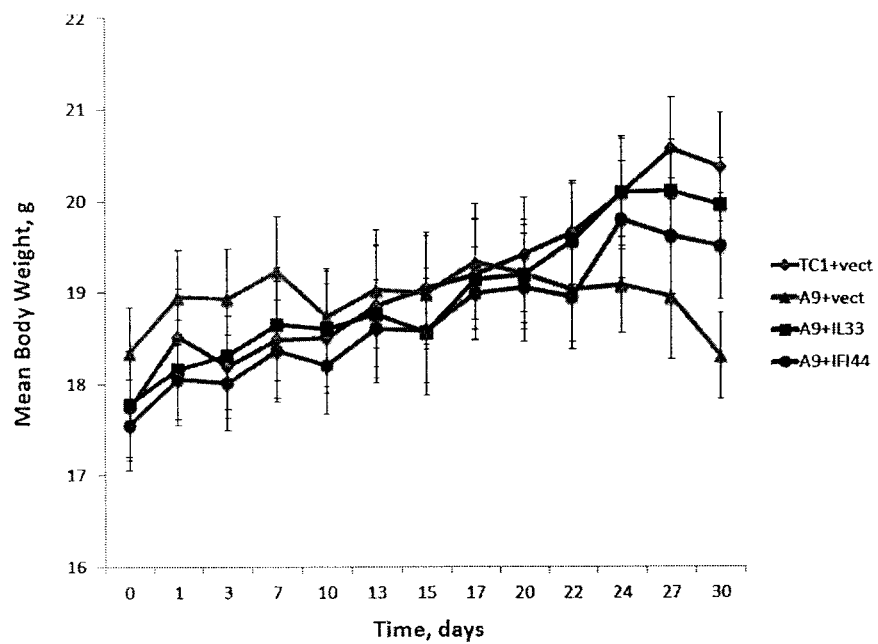

FIG. 41: IL-33 or IFI44 gene-complementation can alter the clinical manifestations of the disease in terms of severity of signs and symptoms and rate of progression. In particular, stable transfection of IL-33 or IFI44-gene into A9 cells maintains animal body weight in vivo.

Figure 42:
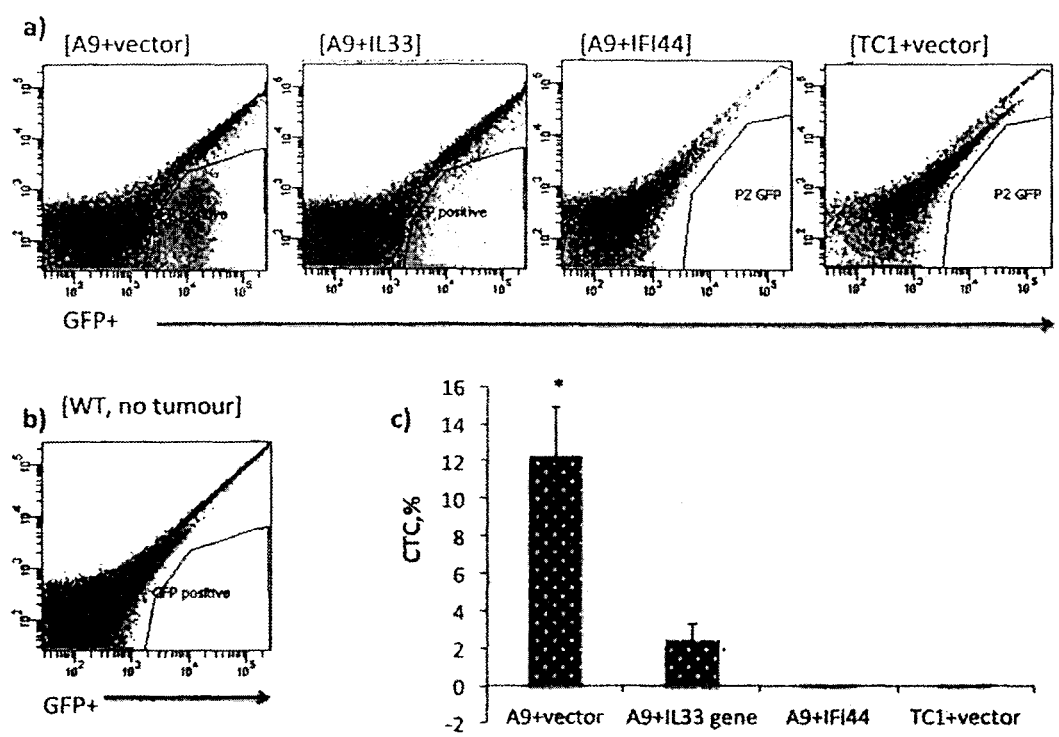

FIG. 42: IL-33 and IFI44 gene-complementation prevents metastatic spread of the disease in vivo. Flow cytometry (a) of GFP positive cells in A9+vector, A9+IL33, A9+IFI44, and TC1+vector and (b) GFP positive cells in wild type, no tumor. c). Graphic representation of percent CTC cells based on GFP positive flow cytometry results.

Figure 43:
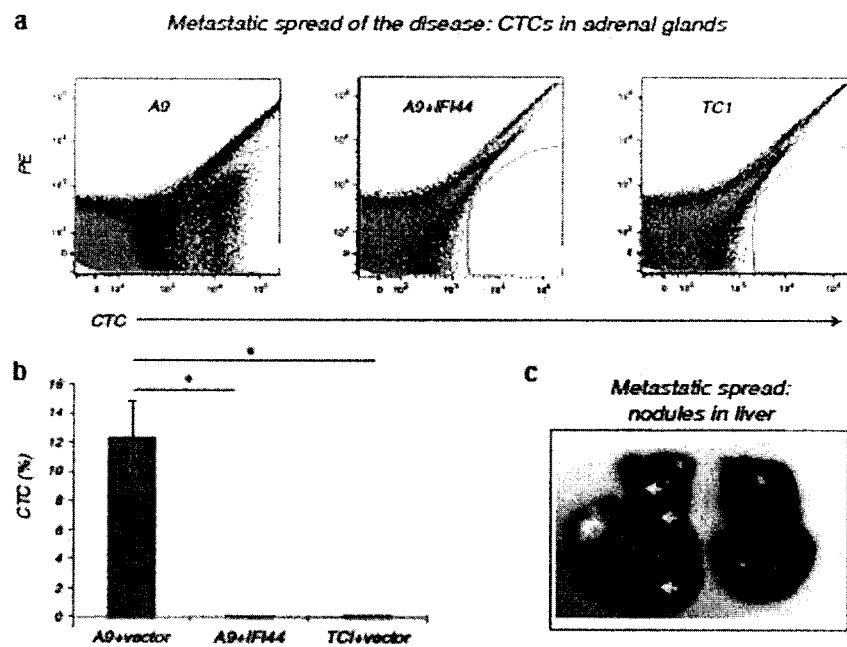

FIG. 43: IFI44 gene-complementation appears to arrest metastatic spread of the disease in a mouse model. (a) Stable transfection of IFFI44 gene into A9 cells effectively stopped the metastatic spread of GFP-positive tumor cells to adrenal glands that were distal from the initial site of subcutaneous inoculation of tumors. The presence of GFP-positive circulating tumor cells in adrenal glands was assessed by flow cytometry. Adrenal glands were isolated from animals bearing A9 (left) or A9+IFI44 tumors (centre) or primary tumors (right). Each graph corresponds to the data from one representative animal. (b) Quantification of GFP-positive circulating tumor cells in (a) as a percentage of total cells. The graph corresponds to the data from eight representative animals in each group. *P<0.05, comparing GFP-positive CTC cells isolated from mice bearing TC1 or A9 or A9+IFI44 tumours (Student's t-test). (c) Metastatic nodules were detected in enlarged livers isolated from animals bearing metastatic A9 tumors (left). Liver isolated from an animal bearing A9+IFI44 tumor (right).

Figure 44:
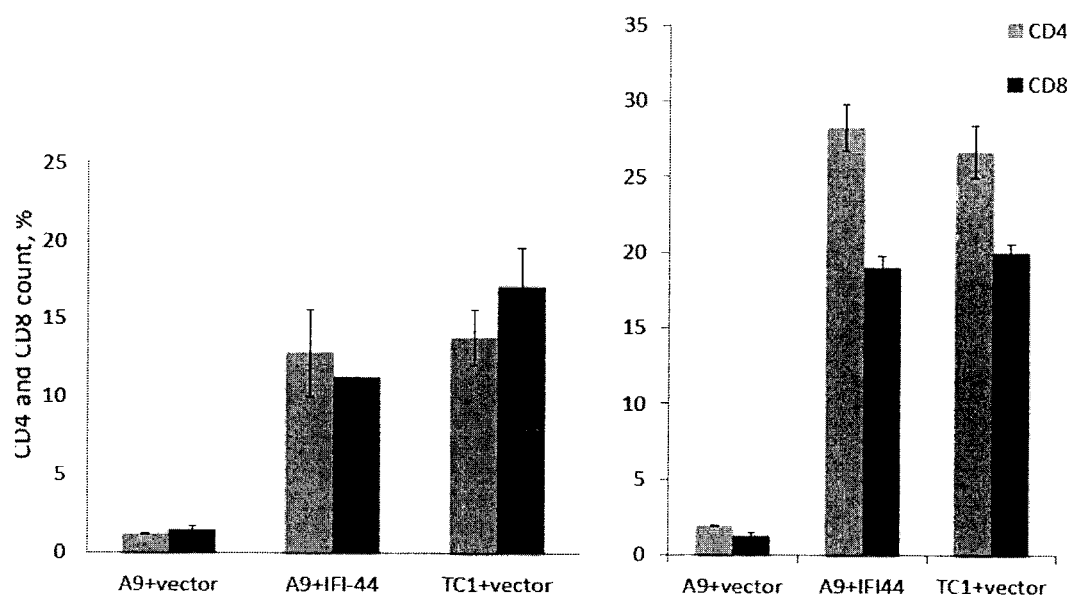

FIG. 44: CD4/CD8 count in IFI44 tumors and lymph nodes

Figure 45:
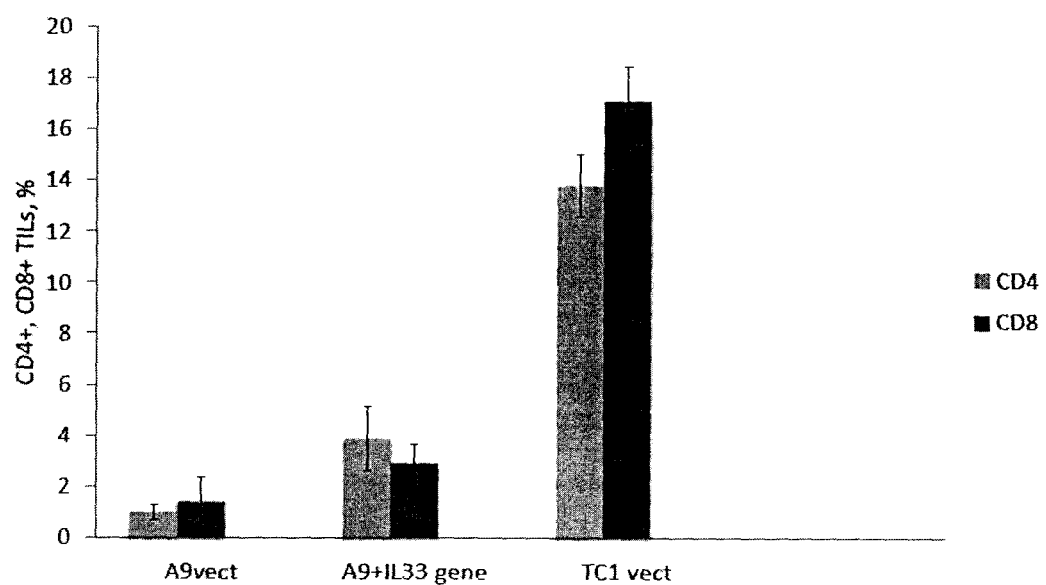

FIG. 45: CD4/CD8 count in IL-33 complemented tumors

Figure 46:
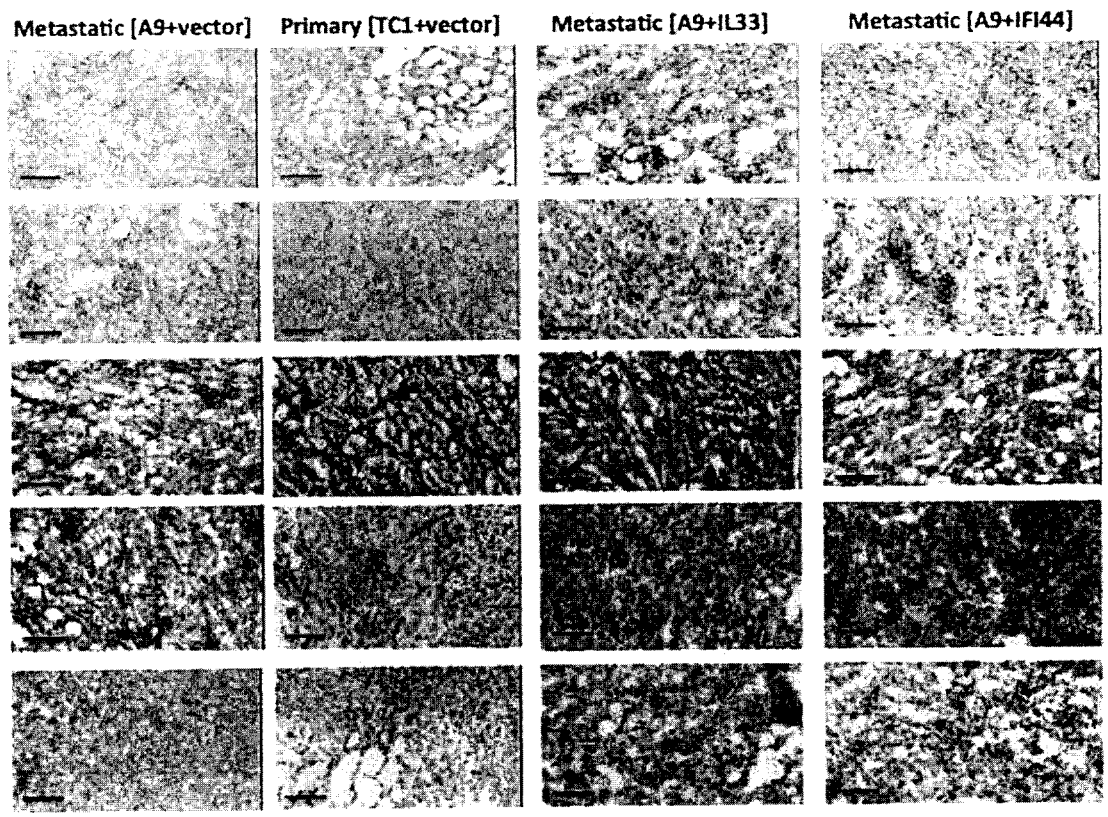

FIG. 46: Tumor morphogy

Figure 47:
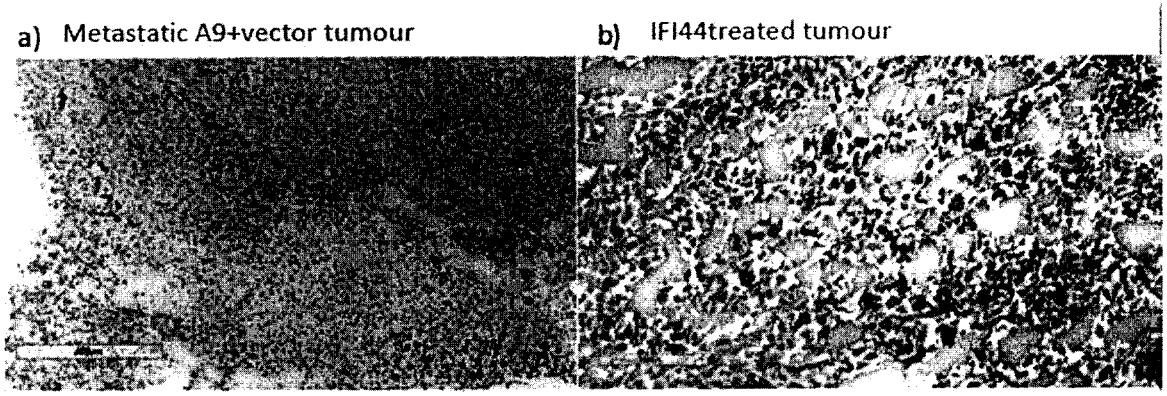

FIG. 47: Up regulation of inflammatory response in genetically modified tumors (Eosinophils, Giemsa staining).

Figure 48:
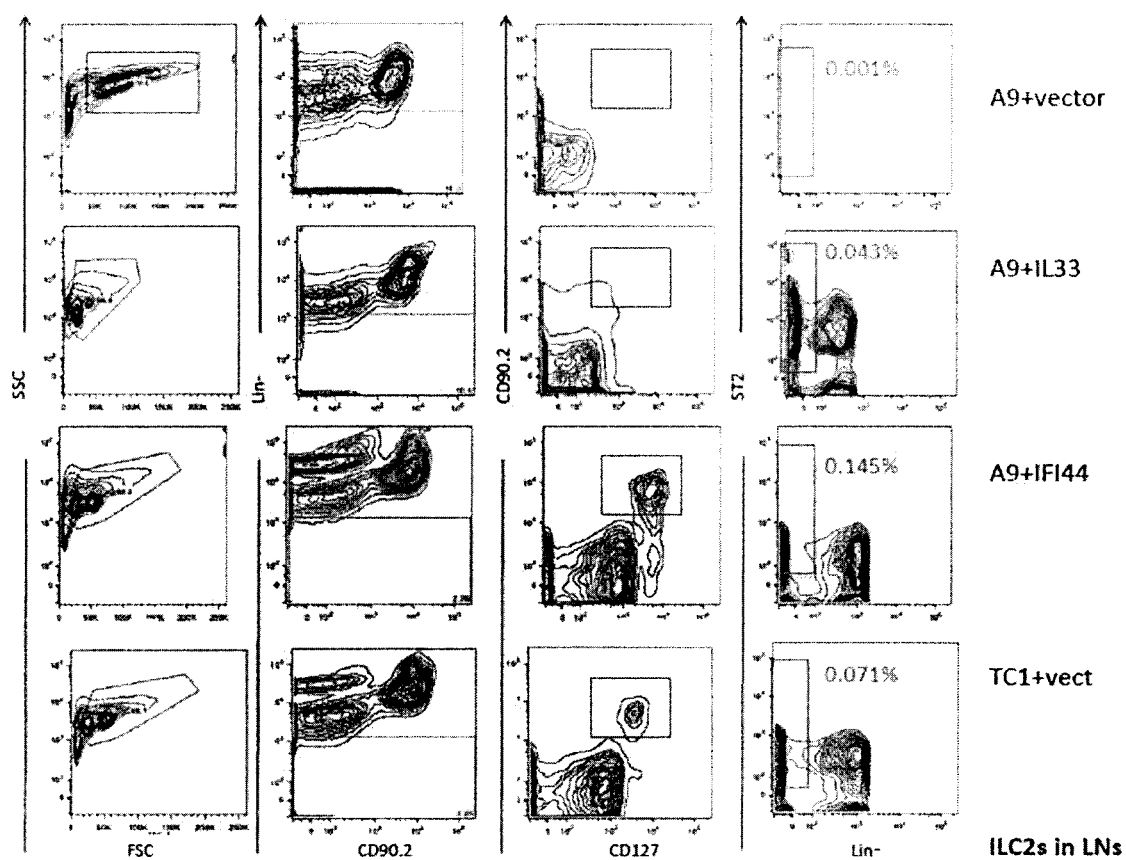

FIG. 48: ILC2s in lymph nodes.

Figure 49:
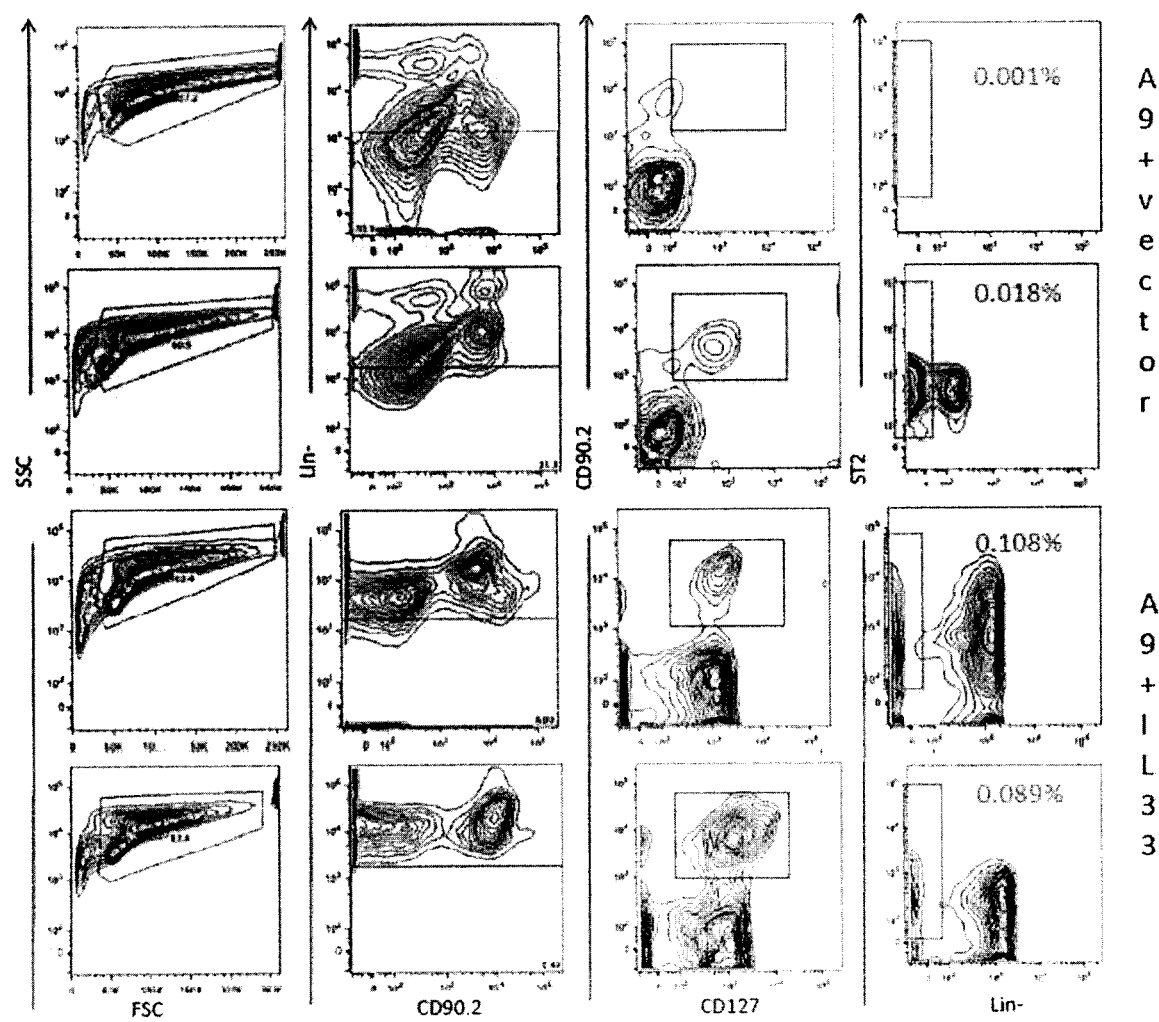

FIG. 49: ILC2s in: A9+vect, IL-33, TC1

Figure 50:
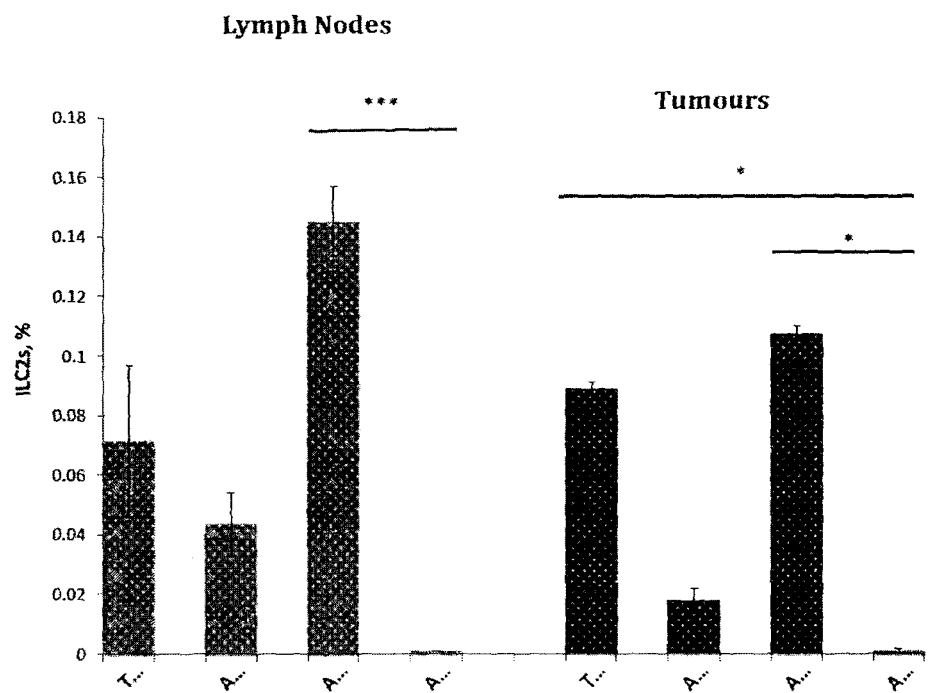

FIG. 50: ILCs in lymph nodes and tumor

Figure 51:
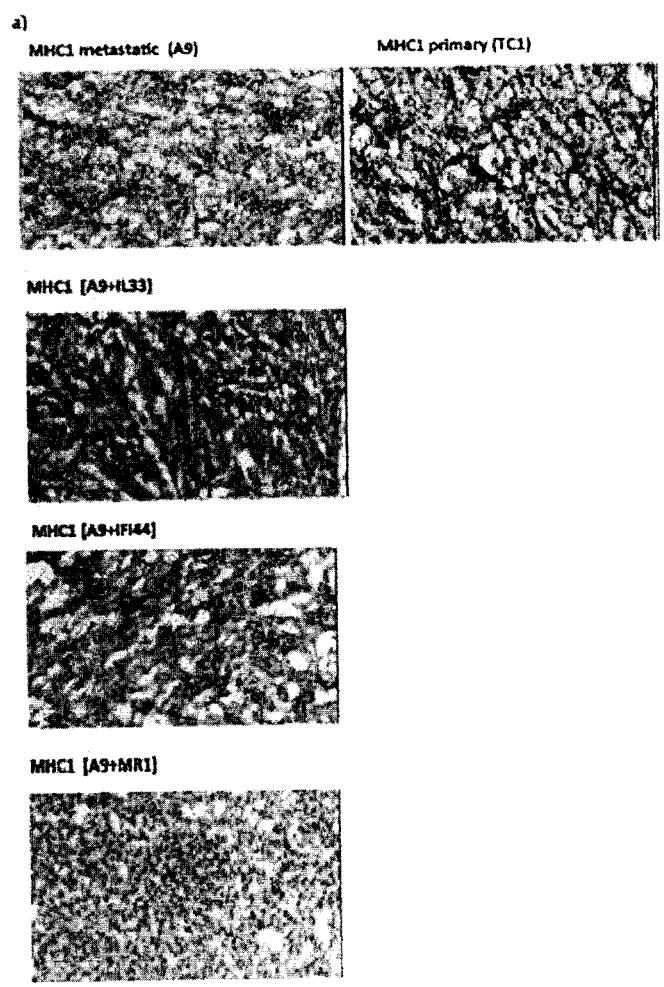
Figure 51:
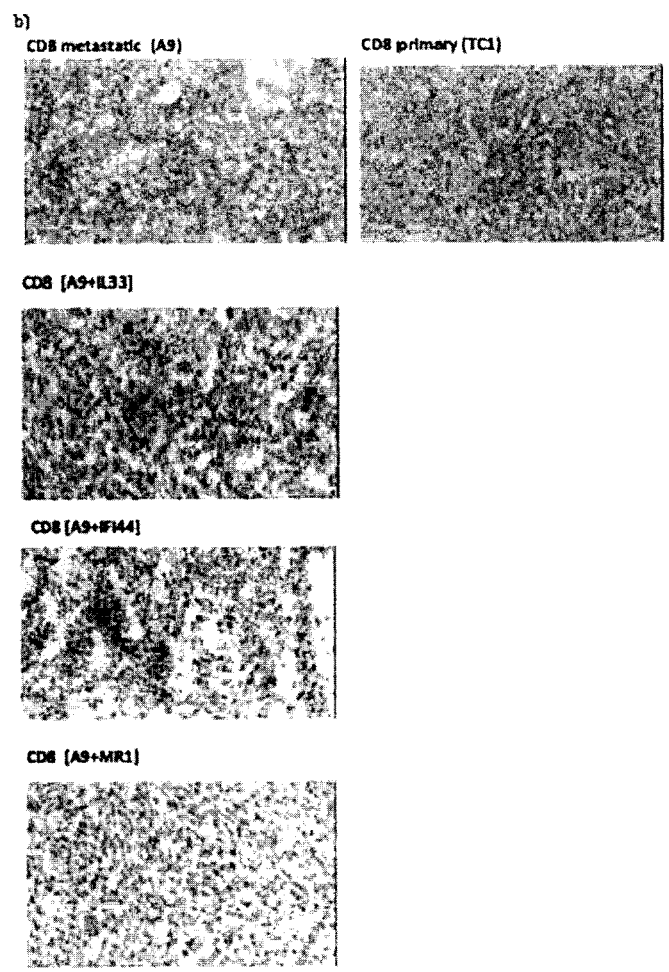
Figure 51:
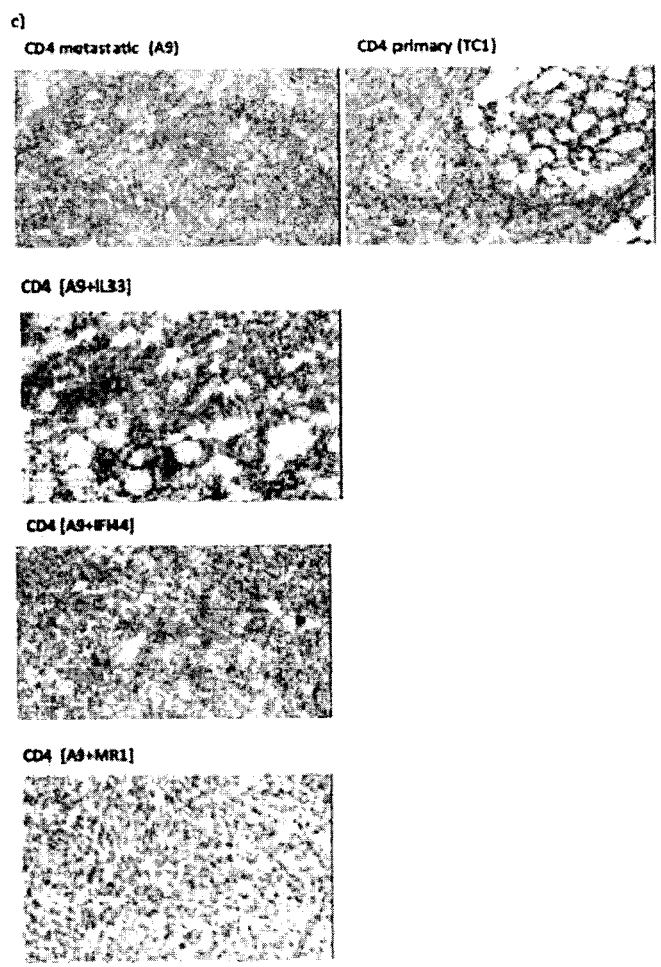
Figure 51:
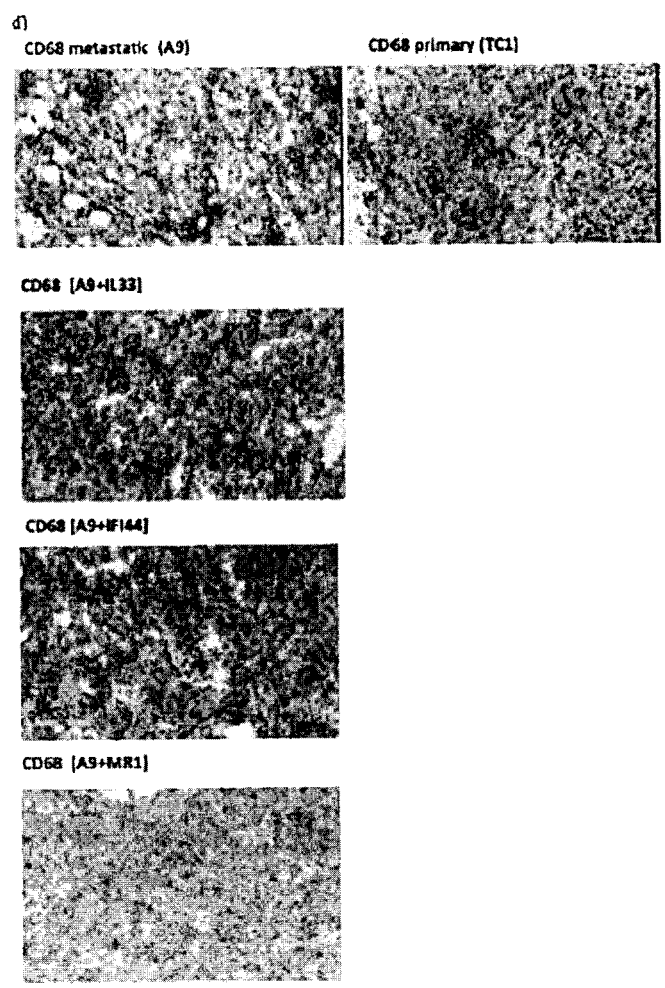
Figure 51:
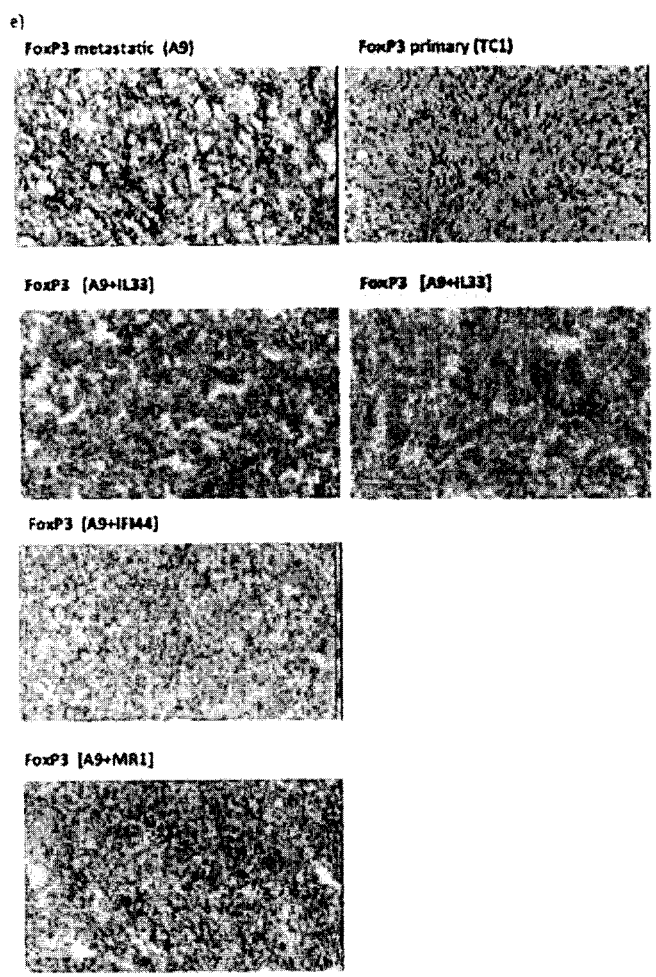
Figure 51:
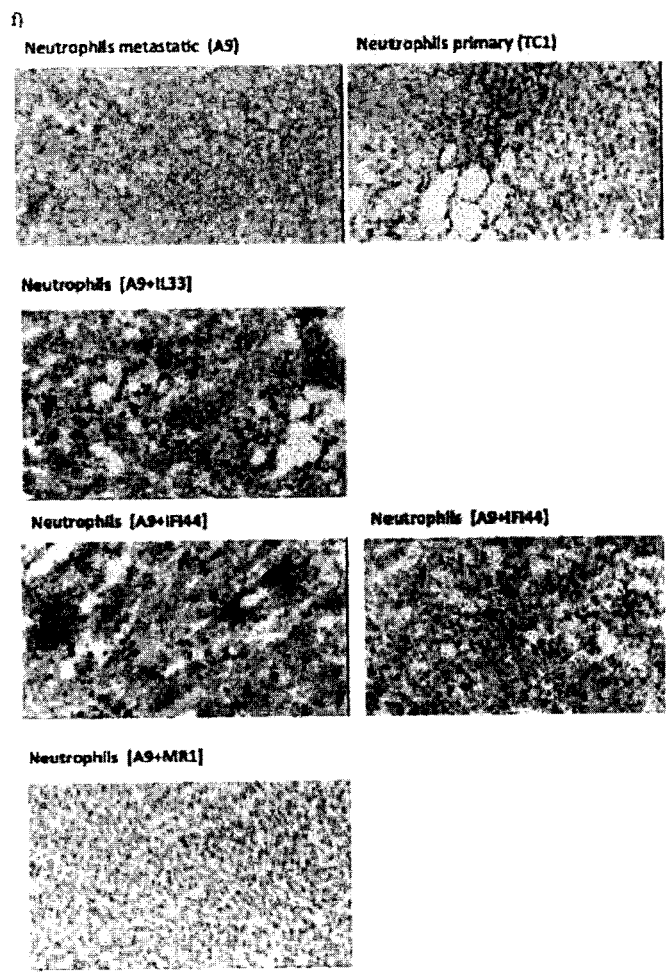

FIG. 51: Immunohistochemical staining for tumor-infiltrating lymphocytes and other targets (CD4, CDS, MHCI, CD68, Ly6G, Foxp3) in metastatic (A9+vector), primary (TC1) and genetically complemented metastatic (A9+IL-33), (A9+1FI44), (A9+MR1) tumors. Genetic complementation of immune evasive tumor with IFI44 or IL-33 shows phenotypic shift towards immune recognition. Genetic modifications of A9 cells with MR1 gene did not affect the immune recognition of metastatic tumor. 10 µm thick sections were stained with appropriate antibodies and imaged at 20× magnification. Visualization by IHC of tumor-infiltrating lymphocytes (TILs) on the sections from solid tissue showed increased staining intensity for MHC19 (a), CDS (b) and CD4 (c) positive cells within the tumors treated with IFI44 or IL-33 when compared to negative control. Positive changes in immune recognition by CTLs were well in line with immune suppressive cell content (e): malignant tumor microenvironment was characterized by up-regulation of resistance-associated markers (FoxP3+), whereas IFI44/IL-33 changes appeared to affect the expansion and accumulation of immune suppressive cells. The anti-tumor inflammatory response was analyzed after examining the infiltration of microphages (d) and neutrophils (f) throughout the tumor tissue. Tumor associated macrophages (TAM) were found to be uniformly distributed within all collected tumors with higher infiltration level in primary [TC1+vector] and IFI44 or IL-33 transfected ones compared to metastatic controls [A9+vector]. Upon tissue damage due to tumor growth in the area, local macrophages and other cells sense the insult and produce inflammatory mediators such as cytokines and chemokines that stimulate the infiltration of large numbers of polymorphonuclear leukocytes such as neutrophils into the tumor tissue. Acute inflammation of adipose tissue was characterized by neutrophilic infiltration in primary [TC1+vector] and genetically complemented metastatic tumors. As such, inflammatory cells and mediators are elevated in the microenvironment of primary [TC1+vector] and [A9+IFI44] or [A9+IL-33] tumors, but not in metastatic tumors [A9+vector], which is in line with our microarray data showing significant down-regulation of inflammation-related genes, such as prostaglandin and leukotriene families, as well as interleukin (IL)-related genes.

Figure 52:
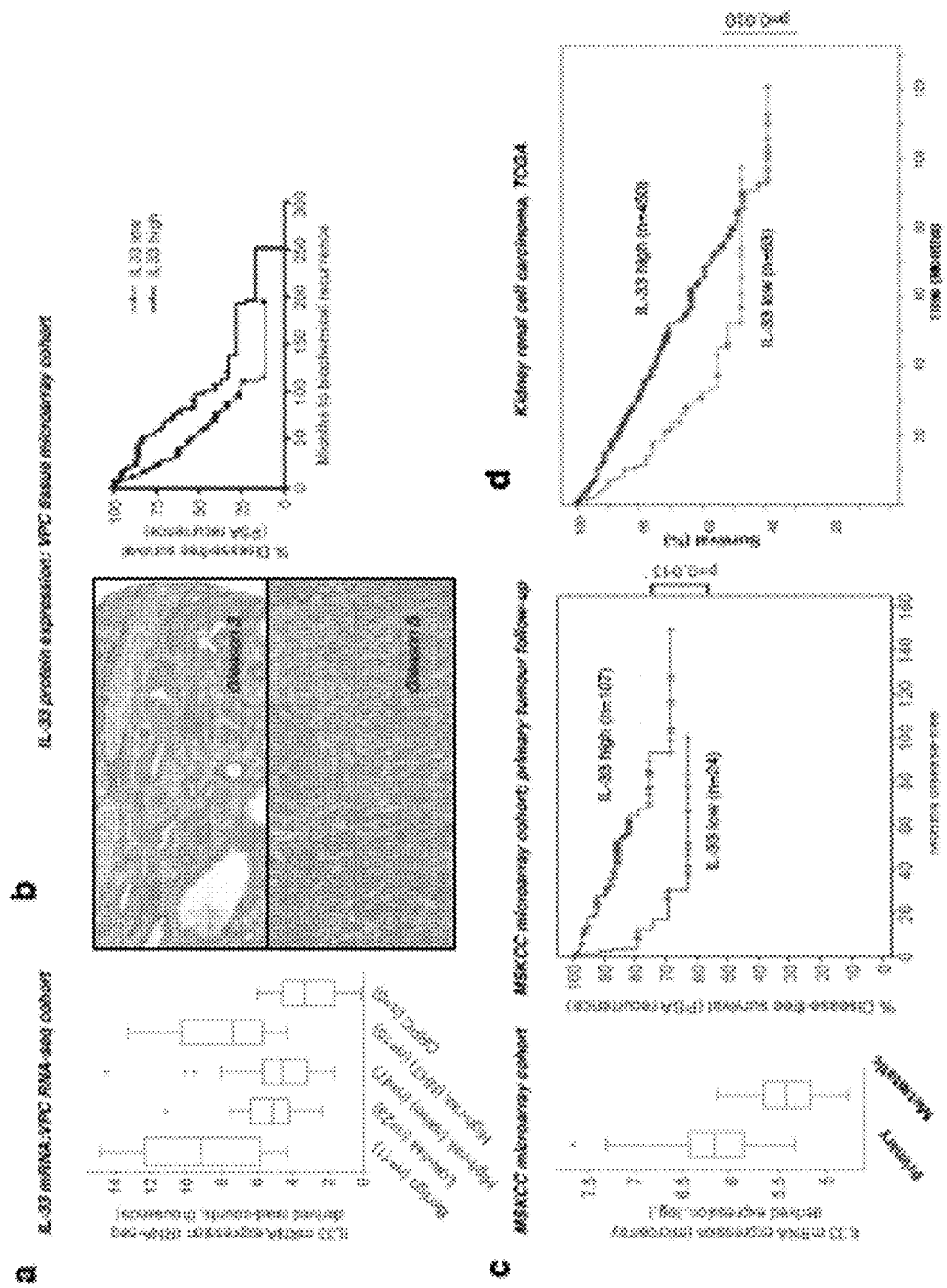

FIG. 52: Reduced IL-33 expression is associated with prostate and kidney renal cell cancer progression. (a) mRNA of IL-33 in CRPC, relative to benign prostate tissue and both low- and high-risk primary tumors. (b) Representative immunohistochemical stains (left panel) showing IL-33 expression in tissue microarrays in prostate tumors of differing Gleason grade. 5 μm thick sections were stained and imaged at 20× magnification. The right panel depicts the association of low IL-33 expression in primary tumors at radical prostatectomy, with significantly shorter time to PSA recurrence. (c) IL-33 mRNA expression in primary and metastatic prostate tumors confirms an association between low IL-33 expression (z-score relative to normal benign<−2) and time to PSA recurrence in this independent cohort of 131 prostate tumors; (d) association between low IL-33 expression (z-score relative to normal benign<−1) and survival of kidney renal cell carcinoma patients.

Figure 53:
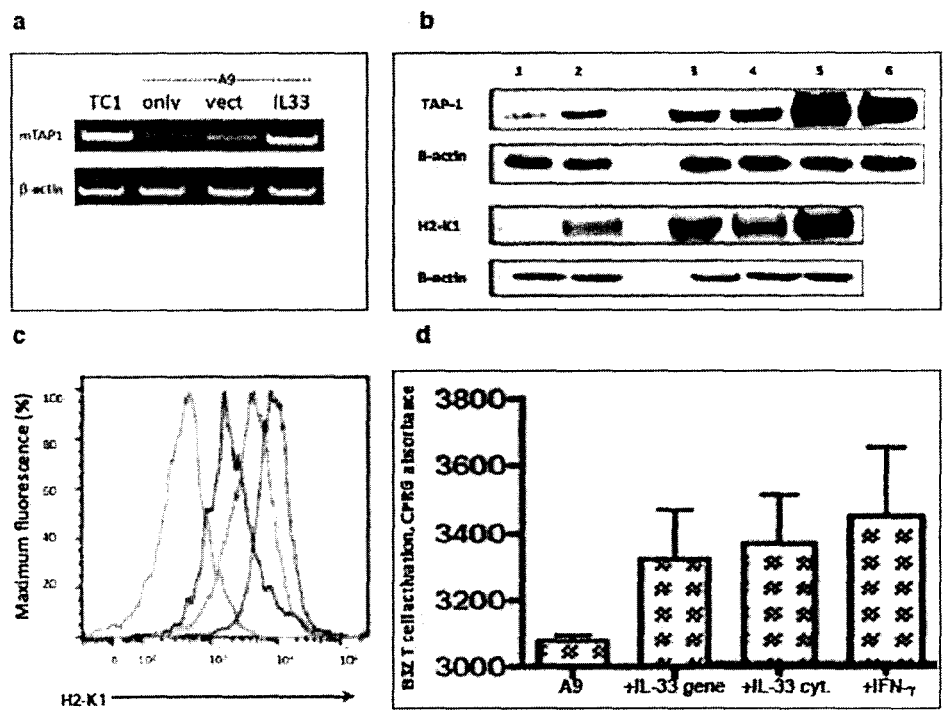

FIG. 53: IL-33 restores TAP-1 and H2-K1 expression/signaling in the MHC-I-loss A9 carcinoma cells, as well as immune recognition of tumors. (a) Transient transfection of A9 cells with IL-33 gene restores TAP-1 gene expression, as detected by RT-PCR. TC1 was used as a positive control for both IL-33 and TAP-1 expression, while A9 untransfected and A9+empty vector were used as negative controls. β-actin was used as loading control. (b) Transient transfection of A9 with IL-33 gene restores TAP-1 and H2-K1 protein expression. Lane 1=A9 cells, Lane 2=A9+empty vector; Lane 3=A9+IL-33; Lane 4=A9+IL-33 cytokine (50 ng/ml); Lane 5=A9+IFN-g cytokine (50 ng/ml); Lane 6=TC1+IL-33. (c) IL-33 induced changes increased H2-K1 surface expression in A9 cells: A9 transfected with the pIRES2-EGFP vector alone (blue); A9 transfected with IL-33 (green); a negative control—A9 untransfected (grey); a positive control—A9 treated with the IFN-gamma (IFN-γ) (red). (d) The expression of IL-33 gene or the addition of exogenous IL-33 cytokine protein enhanced antigen-specific recognition by B3Z T-cells of the OVA presented on the surface of tumor cells. IFN-γ was used as a positive control.

Figure 54:
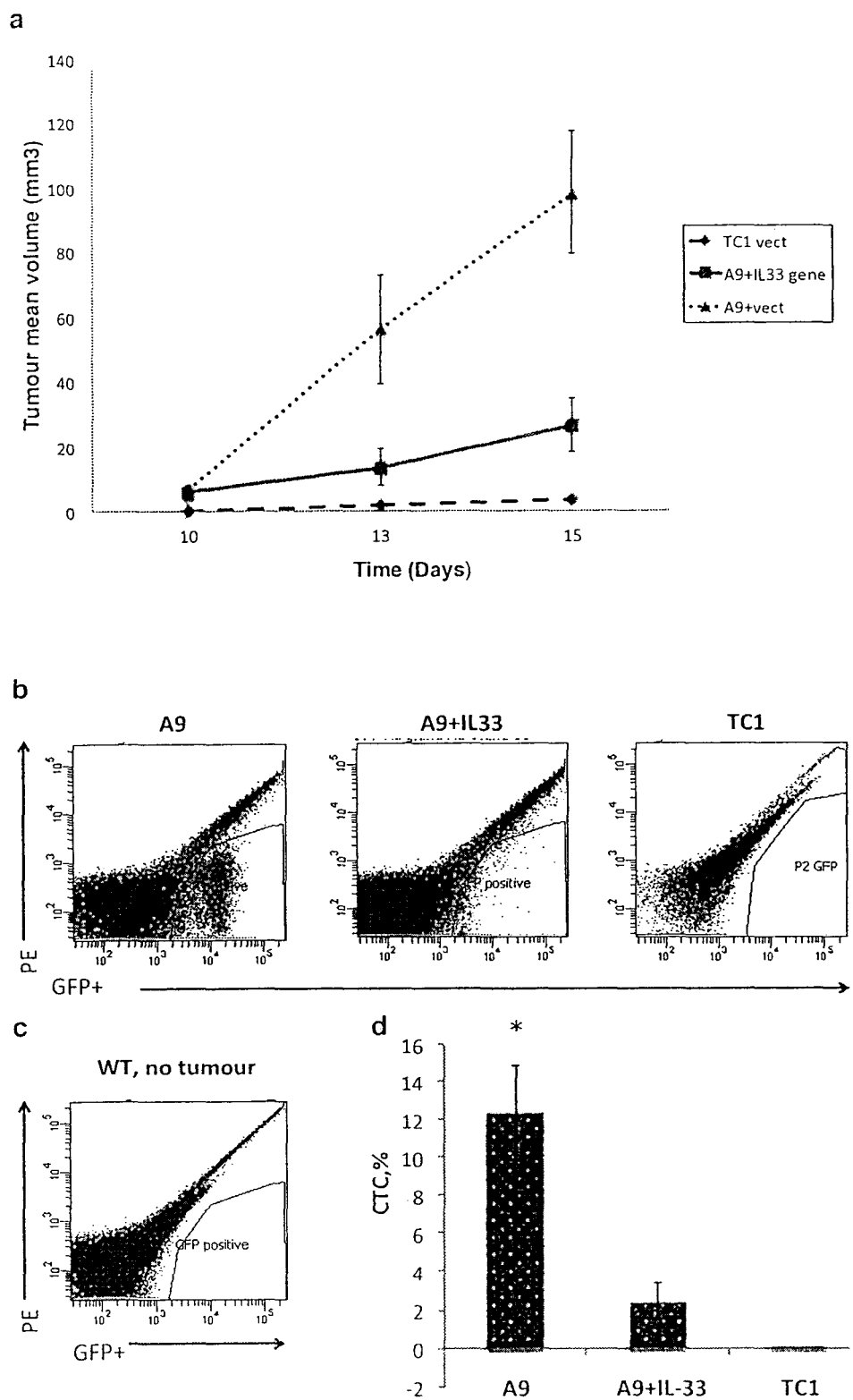

FIG. 54: IL-33 gene-complementation suppresses tumor growth rate in vivo and inhibits metastatic spread of tumor cells in a mouse model. (a) Stable transfection of IL-33 gene into A9 cells resulted in significantly inhibited tumor formation in mice. GFP-positive circulating tumor cells were isolated from adrenal glands that were distal from initial subcutaneous inoculation, and assessed using flow cytometry: (b) animals injected with A9 cells (left); animals injected with IL-33 expressed metastatic cells (centre); animals bearing primary tumors (right). (c) Adrenal glands were isolated from tumor-free wild type animals to indicate no overlapping autofluorescent cells in flow cytometry gating. (d) Quantification of GFP-positive circulating tumor cells in (b) as a percentage of total cells. Each graph corresponds to the data from one representative animal. *$P<0.05$, comparing GFP-positive CTC cells isolated from the primary (TC1) and metastatic (A9) bearing animals (Student's t-test).

Figure 55:
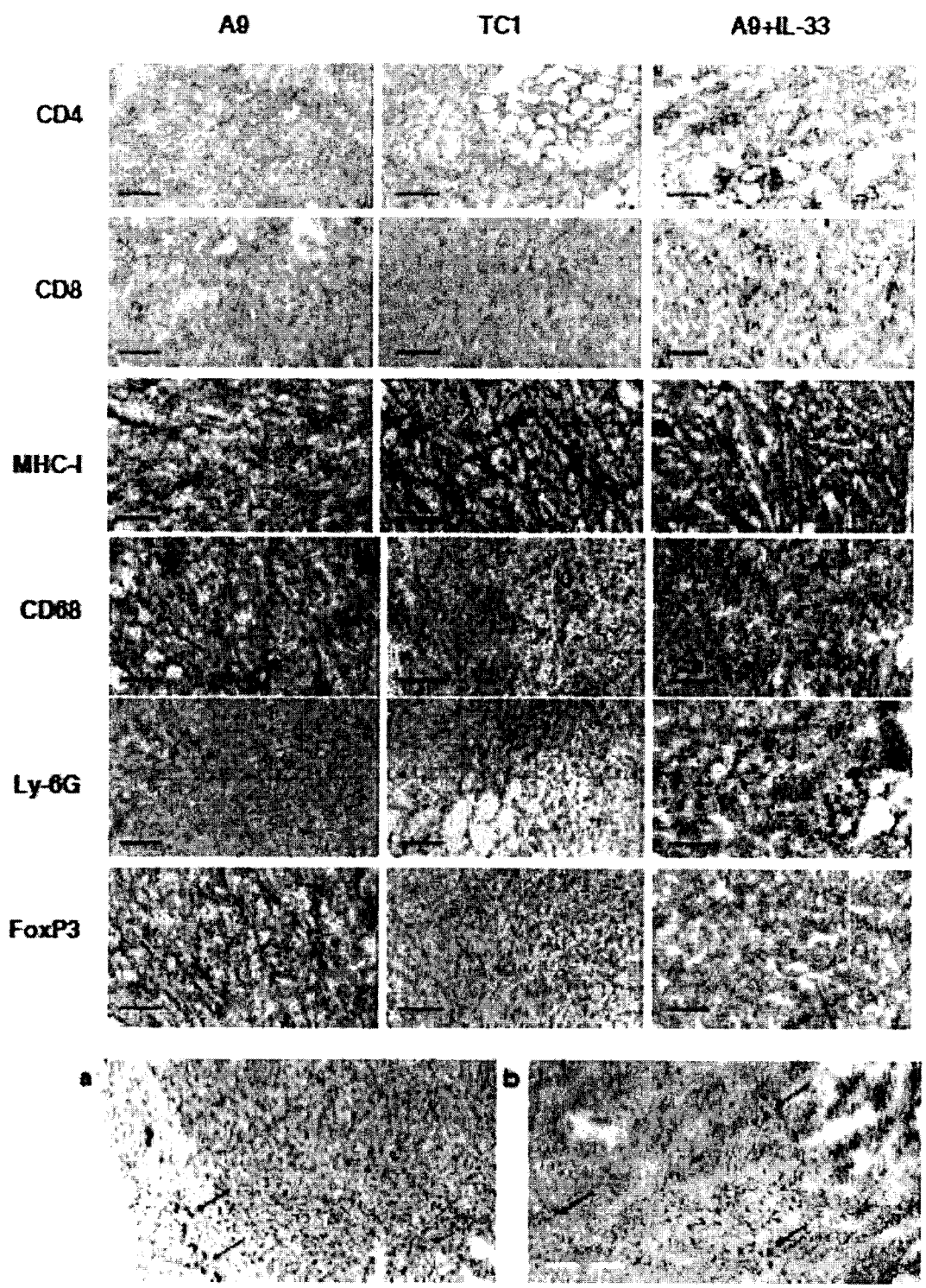

FIG. 55: Immunohistochemical staining of tumors. Upper panel: Tumor-infiltrating lymphocytes and other targets (CD4, CD8, MHC-I, CD68, Ly-6G, FoxP3) in metastatic A9, primary TC1 and metastatic tumors genetically complemented with IL-33. Genetic complementation of immune evasive tumor shows clear phenotypic shift towards immune recognition. 10 μm thick sections were stained with appropriate antibodies and imaged at 20× magnification. Bottom panel: Eosinophil recruitment into tumor tissue is induced by IL-33 expression (mouse). (a) Eosinophils are located on the border between metastatic (A9) tumor and normal tissue. (b) IL-33-induced changes allow eosinophilic infiltration into tumor tissue, which expresses IL-33. 10 μm thick tumor sections were stained with Giemsa stain and imaged at 10× magnification.

Figure 56:
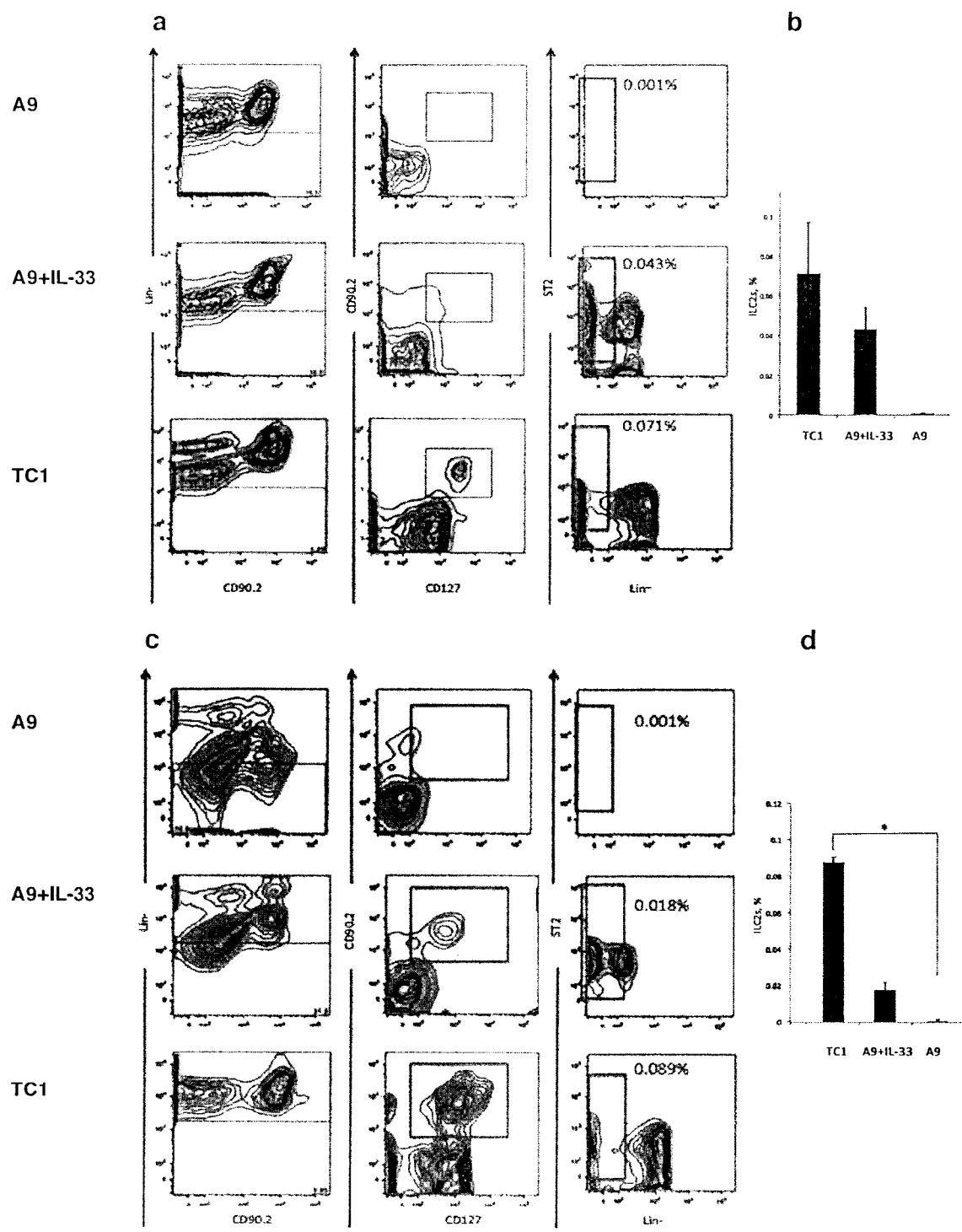

FIG. 56: The frequency of ILC2s is elevated in animals bearing primary tumors and metastatic tumors stably transfected with IL-33 gene. Innate Lymphocytes isolated from disaggregated lymph nodes and tumor tissues were analyzed by flow cytometry as Lin-ST2+CD127+CD90.2+ cells. Gating strategy included first gating on lineage-negative (Lin−) and (CD90.2)-positive leukocytes and further analyzing for ST2+ and CD127+ expression. (a) Gating and (b) quantification of ILC2s isolated from lymph nodes. The ranges represent the data comparing eight different animals in each treatment group. (c) Gating and (d) quantification of ILCs isolated from tumors. The ranges represent the data comparing four different animals in each treatment group; *$P<0.05$ compared ILC2 cells isolated from the primary and metastatic tumors (Student's t-test).

Figure 57:
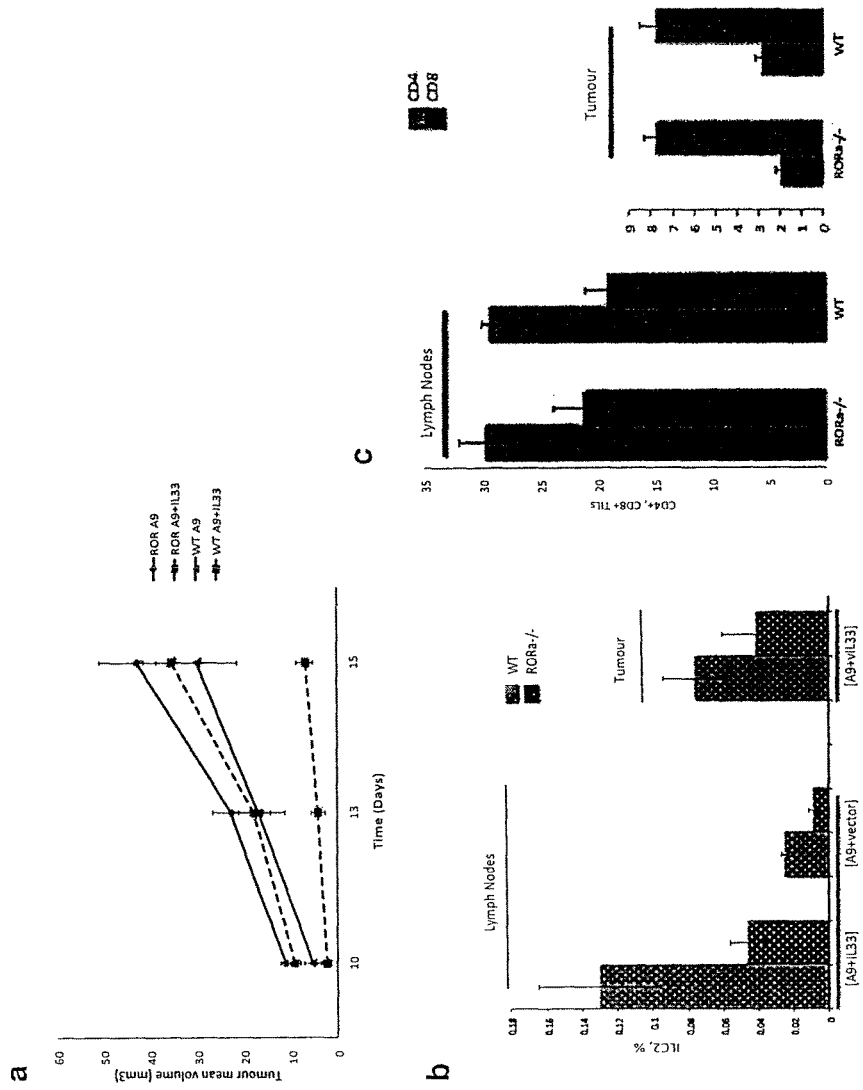

FIG. 57: IL-33 can modify tumor progression and support the conclusion that ILC2s participate in cancer immune surveillance through RORα-IL-33-ILC2 axis. Mice were transplanted with either RORα−/− or wild type bone marrow, and after successful bone marrow repopulation, metastatic tumors with and without IL-33 expression were injected into these chimeric mice. (a) Stable transfection of IL-33 gene into A9 cells resulted in significantly inhibited tumor formation in WT mice when compared to RORα−/− chimeras. (b) The numbers of ILC2 cells found in neighboring lymph nodes were significantly lower in RORα−/− mice compared to wild type chimeras. (c) RORα deficiency had no effect on the ratio of CD4/CD8 lymphocytes.

FIG. 58: IL-33-ILC2 axis links the adaptive and innate immune responses together during tumor development. IL-33 expressing tumor environment stimulates the development of ILC2 cells and functionally activates them through the ST2 receptor pathway. Functionally active ILC2s trigger the type 2 effector pathway through secretion of IL-4 and IL-13 together with a direct antigen presentation via MHCII molecules. Through the release of IL-5 by ILC2s and subsequent recruitment of eosinophils, the chemokine profiles of tumor microenvironment is changed to attract CD8+ T cells and to direct the activation of CTL mediated killing and cancer rejection.

Figure 59:
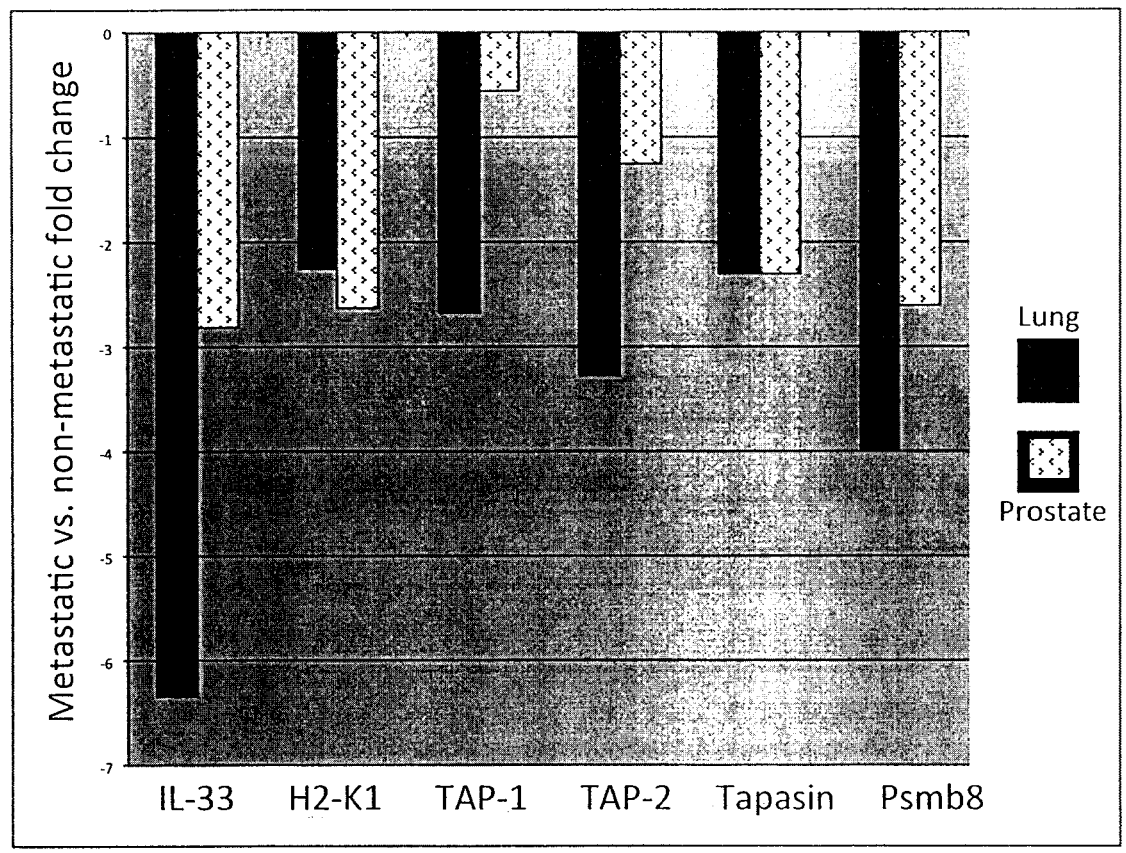

FIG. 59: The expression of IL-33 and various antigen-presentation processing genes was down regulated in murine metastatic lung and prostate carcinomas. Metastatic lung carcinoma (A9) gene expression was compared to primary, nonmetastatic tumor (TC1). Metastatic prostate carcinoma (LMD) gene expression was compared to primary, nonmetastatic tumor (PA). Microarray data was obtained using a human Agilent chip and the GeneSpring GX software. IL-33=interleukin 33; H2-K1=major histocompatibility complex class I; TAP-1=transporter associated with Antigen Processing 1; TAP-2=transporter associated with Antigen Processing 2; Tapasin=TAP-associated glycoprotein; Psmb8=proteasome subunit beta type 8.

Figure 60:
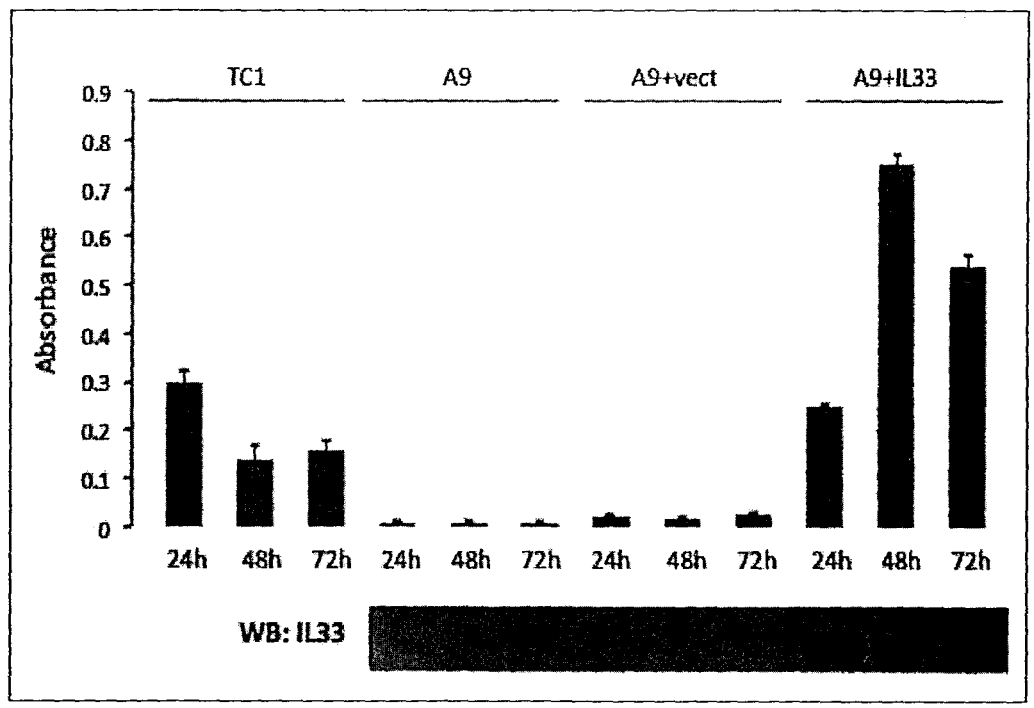

FIG. 60: IL-33 gene transient transfection up regulated IL-33-protein secretion by A9 cells (ELISA), as well as total intracellular IL-33 protein level (Western Blot). Gene expression construct with a full-length cDNA for IL-33 has been produced within the pIRES2-EGFP vector. IL-33 gene was introduced into the murine lung carcinoma cell line A9, which has MHC-I loss phenotype and is immune evasive. IL-33 protein secretion was measured by ELISA and the total intracellular IL-33 protein level was measured by Western Blot respectively at various time points: 24 h, 48 h, 72 h. TC1=primary tumor cells; A9=metastatic tumor cells; A9+pIRES2-EGFP vector=metastatic tumor cells transfected with pIRES2-EGFP; A9+IL-33=metastatic tumor cells transfected with pIRES2-EGFP vector+IL-33 gene.

Figure 61:
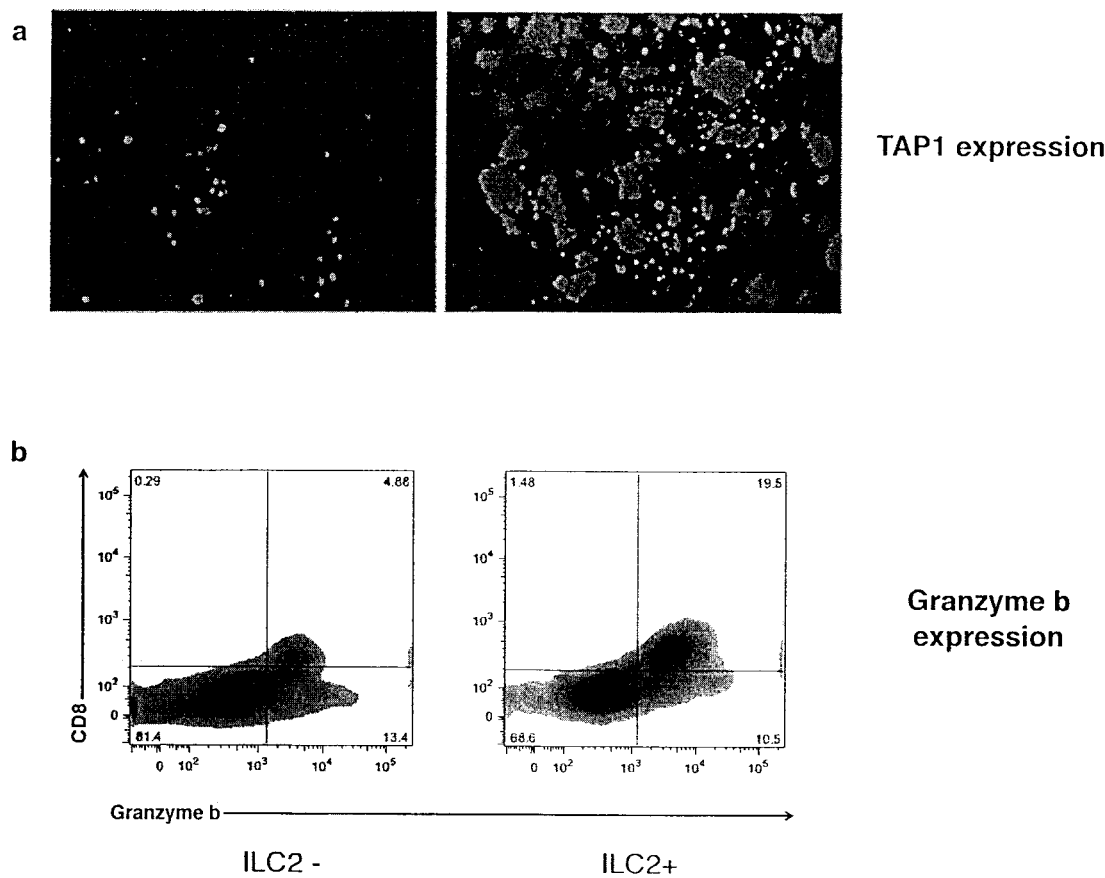

FIG. 61: Impact of ILC2s on specific cytolytic T cell effector mechanisms. Co-culture of murine prostate carcinoma cells (LMD) and CD8 T cells with ILC2s (right panel) or without ILC2 cells (left panel): (a) TAP-1 expression level in LMD cells before (left) and after (right) activation with ILC2 cells; (b) Granzyme b expression by CTL cells before (left) and after (right) activation with ILC2 cells.

Figure 62:
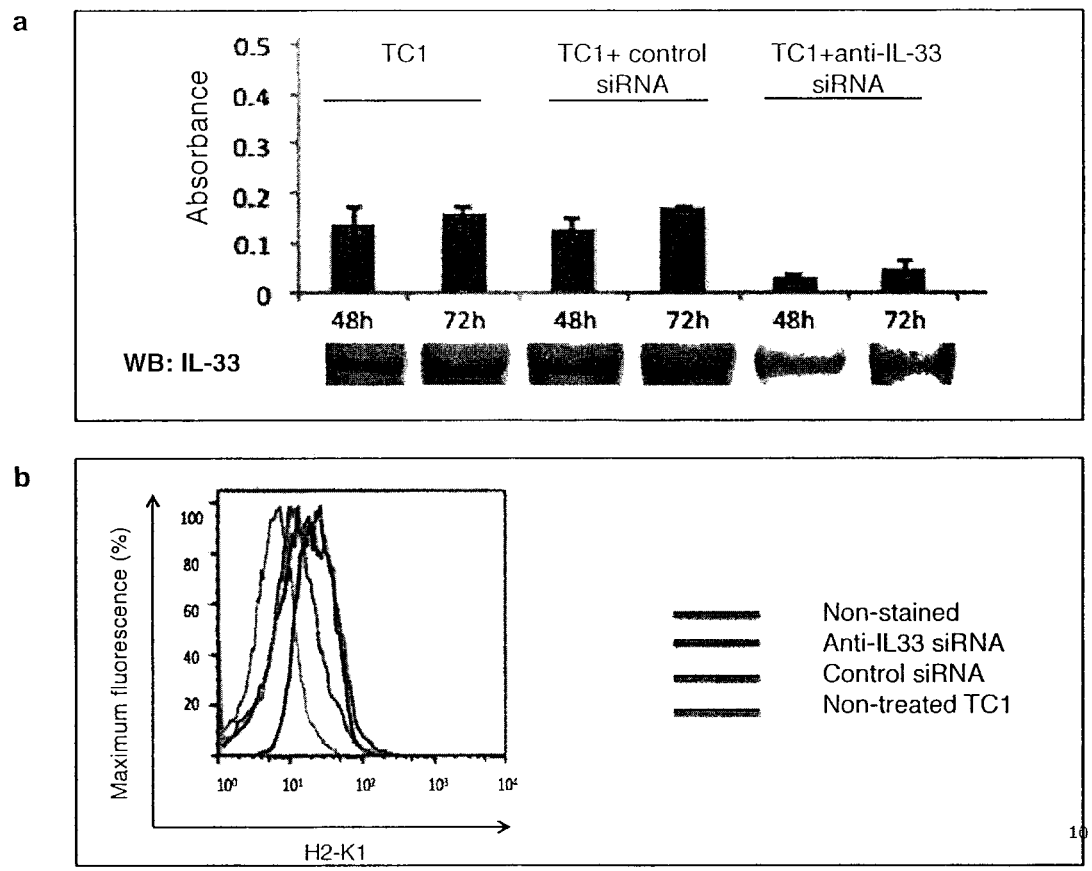

FIG. 62: Down regulation of IL-33 gene decreased H2-K1 protein expression in primary lung tumor cells. TC1 primary tumor cells were treated with siRNA targeted against IL-33 for 48 or 72 hrs. (a, top) ELISA assay was used to measure the level of secreted IL-33 in supernatants). (a, bottom) Western Blot analysis was used to measure the level of IL-33 protein in the cell pellet. (b) FACS was used to measure the expression of H2-K1 on the surface of tumor cells. TC1 cells were treated for 72 hrs with siRNA against IL-33 and cell surface expression of H2-K1 was assessed by flow cytometry.

Figure 63:
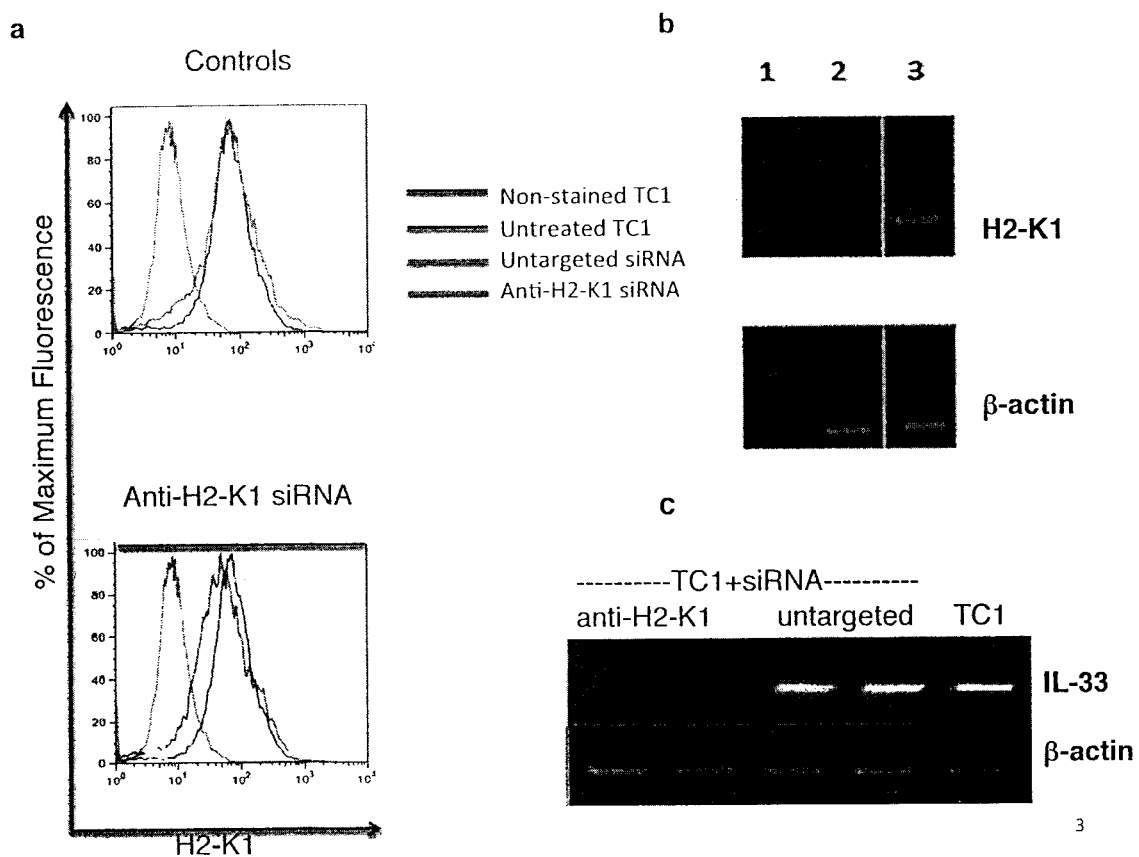

FIG. 63: Down regulation of H2-K1 decreased IL-33 gene expression in murine primary lung tumor cells. TC1 primary tumor cells were treated with two different siRNAs specifically targeted against mouse MHC-I (H2-K1) for 96 hrs, after which cDNA was isolated. (a) MHC-I surface expression down-regulated in TC1 cells in response to anti-H2-K1 siRNA treatment (FACS). (b) Primers against H2-K1 were used to examine the resulting transcription levels of the H2-K1 gene (RT-PCR): Lane 1=molecular weight control, (GeneRuler 1 kbDNA ladder, Life Technologies); Lane 2=TC1 cells treated with siRNAs against H2-K1; Lane 3=untreated TC1 cells; β-actin was used as loading control. (c) Primers against IL-33 were then used to examine the resulting transcription levels of the IL-33 gene (RT-PCR): Lanes 1, 2=TC1 cells treated with siRNA against H2-K1; Lane 3=untreated TC1 cells; Lane 4, 5=TC1 cells treated with nonspecific siRNAs; β-actin was used as loading control.

Figure 64:
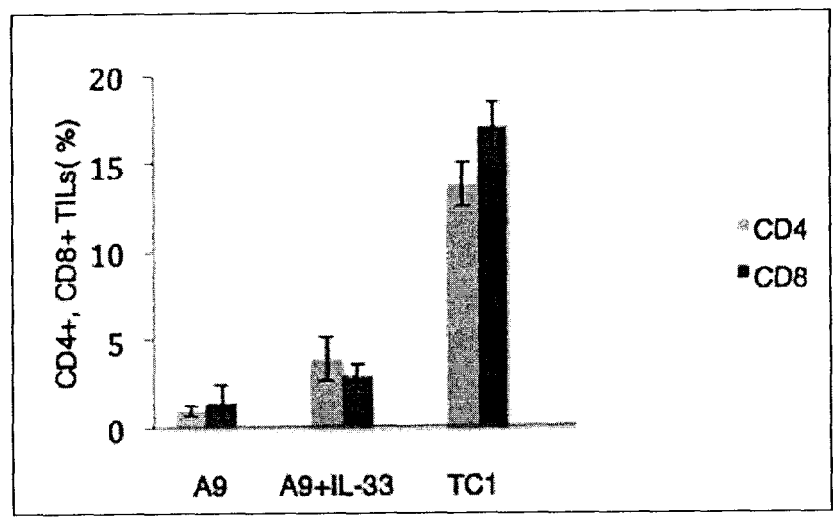

FIG. 64: IL-33 gene induced an increase in the number of tumor infiltrating lymphocytes (TILs). Flow cytometry was used to innumerate the TILs that were isolated from resected tumors, which is shown here as a percentage of total cells in the tumor. More TILs were found to be present in tumors that expressed IL-33, which includes both A9+IL-33 and the primary tumor, TC1.

Figure 65:
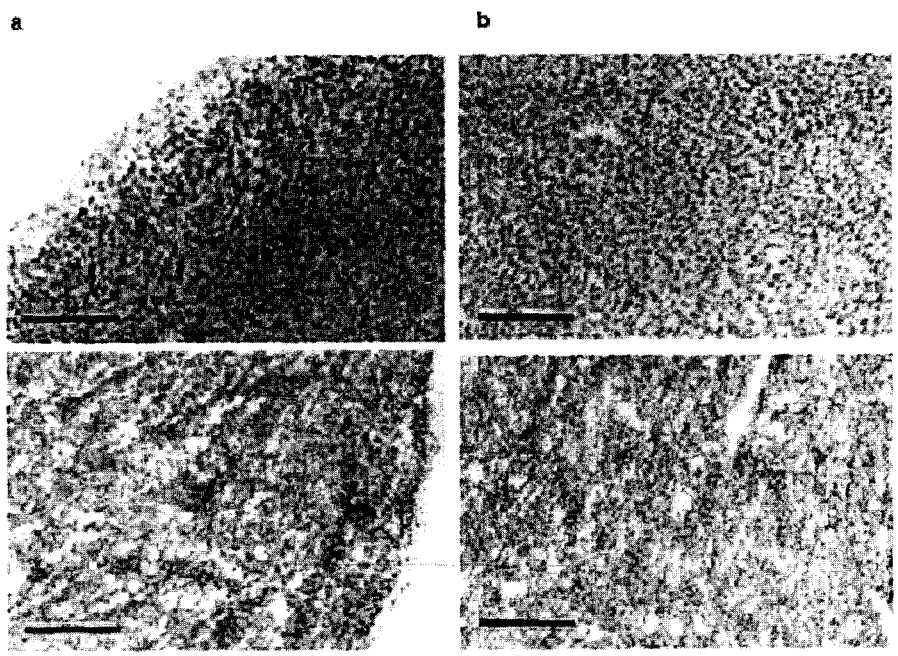

FIG. 65: IL-33 mediated changes decreased proliferation of tumor cells, but had no effect on apoptosis. (a) Intense proliferation along the periphery of the A9 metastatic tumor (top) is significantly reduced in vivo in metastatic tumors genetically complemented by IL-33 (bottom). (b) IL-33 expression does not affect cellular apoptosis: A9 metastatic tumors (top); in genetically modified tumors A9+IL-33 (bottom). 10 µm thick sections of tumors were stained with anti-Ki-67 (A) and anti-Caspase3 (B) antibodies and imaged at 10× magnification.

Figure 66:
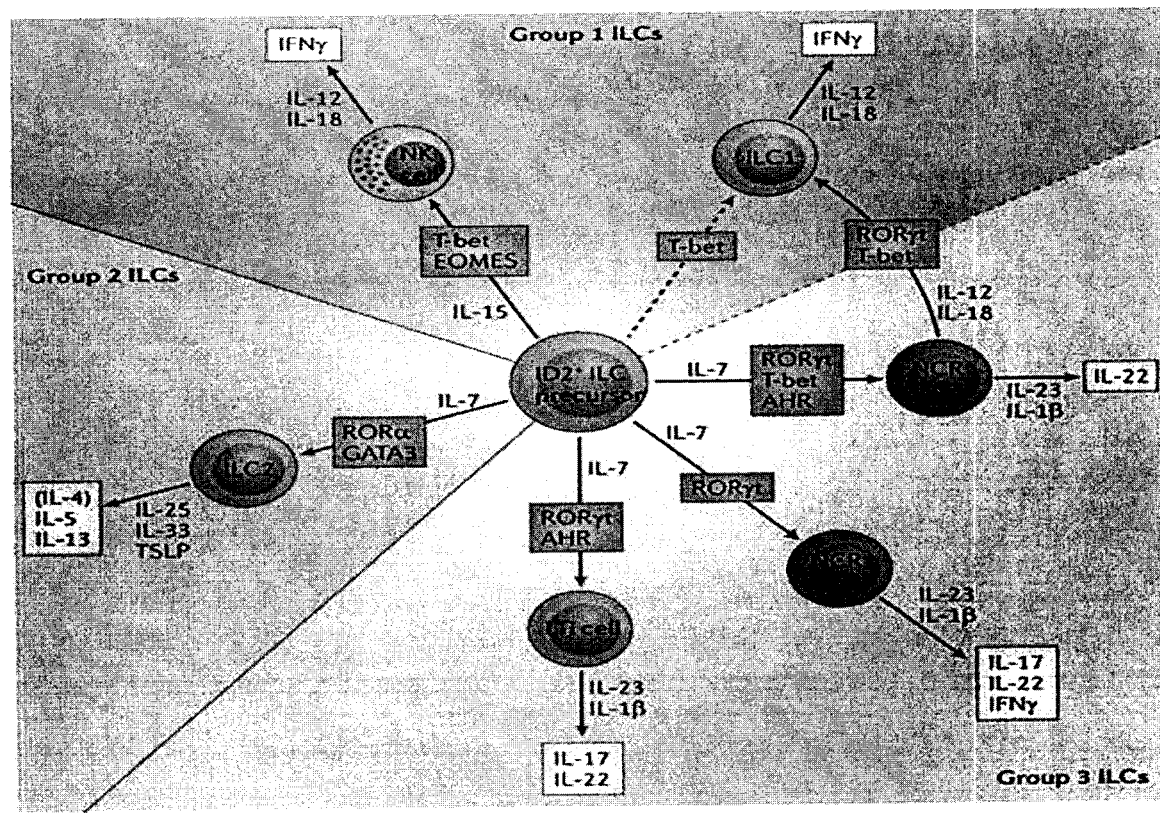

FIG. 66: GATA 3/RORα involvement into innate immune response. ILC2s development and functioning is dependent on the IL-33 presence in the microenvironment.

Figure 67:
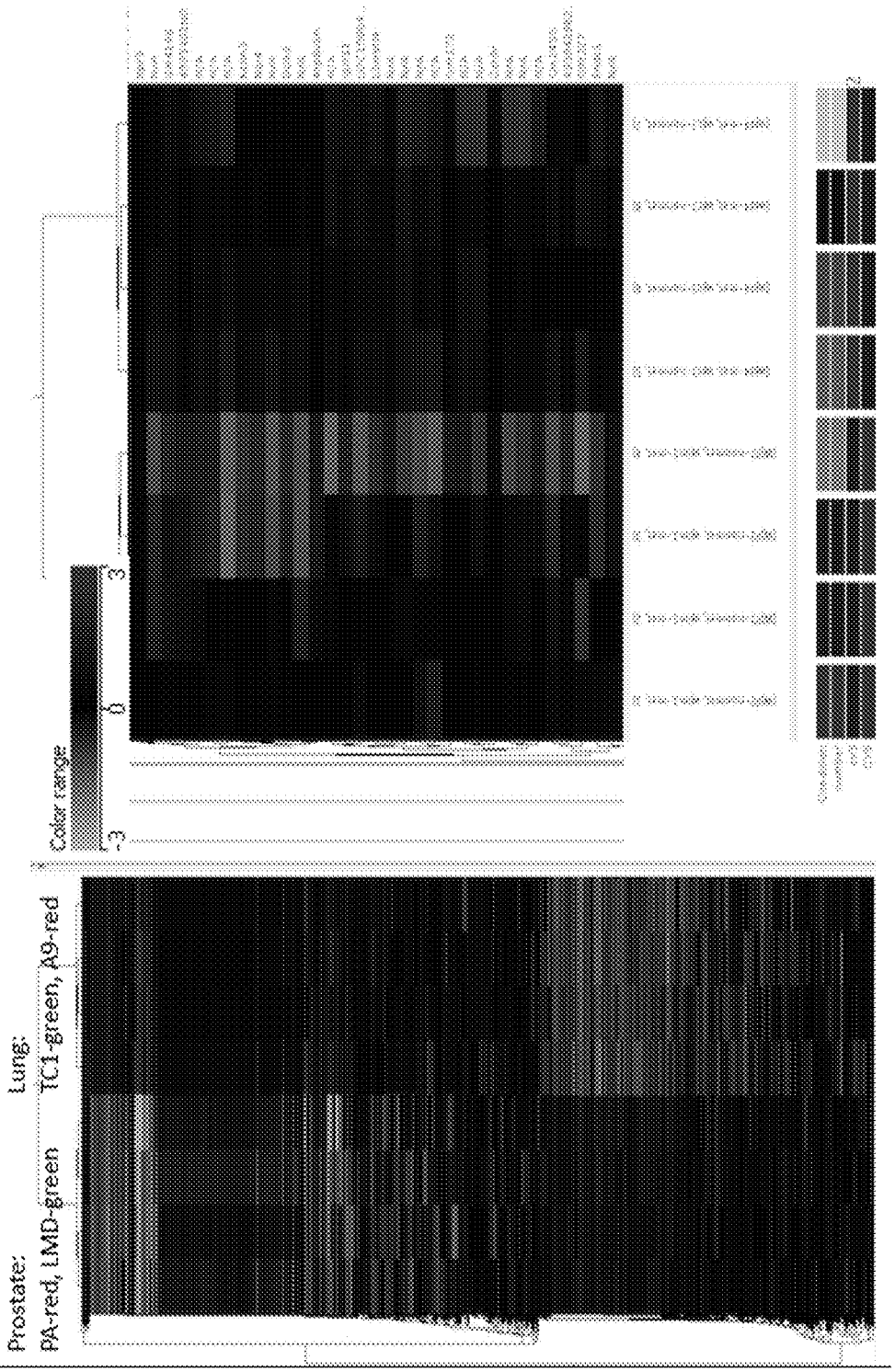

FIG. 67: Comparative microarray profiling of primary/metastatic tumor cells (an initial unsupervised clustering, 28005 Two-Colour Agilent array). An initial unsupervised clustering was performed using all probes on the array. This is shown in unsupervised cluster-allsamples-TREE.png. Genes are on the vertical axis and individual samples are on the horizontal. The left panel shows all of the samples and all of the probes on the array clustered together. The right panel is a blow-up of a region in the left panel. The right panel is included as it displays the sample identifiers along the bottom. Clustering was done using a two-way hierarchical clustering with a pearson centered distance metric following average linkage rules. As can be seen, the overwhelming conclusion is that the samples show a very different expression signature based on their tissue site. Genes that were statistically different between the two tissue types were identified. Data was first filtered to remove the confounding effect probes that show no signal at all in either channel may have on subsequent analysis. Only probes that were in the upper $80^{th}$ percentile of the distribution of intensities were allowed to pass through this filtering. The final set contained 48731 probes. Cy3 green, Cy5 red. Relative intensities of each fluorophore may then be used in ratio-based analysis to identify up regulated and down regulated genes. Fully complementary strands bind strongly, partially-weakly. The samples show a very different expression signature based on their tissue site.

Figure 68:
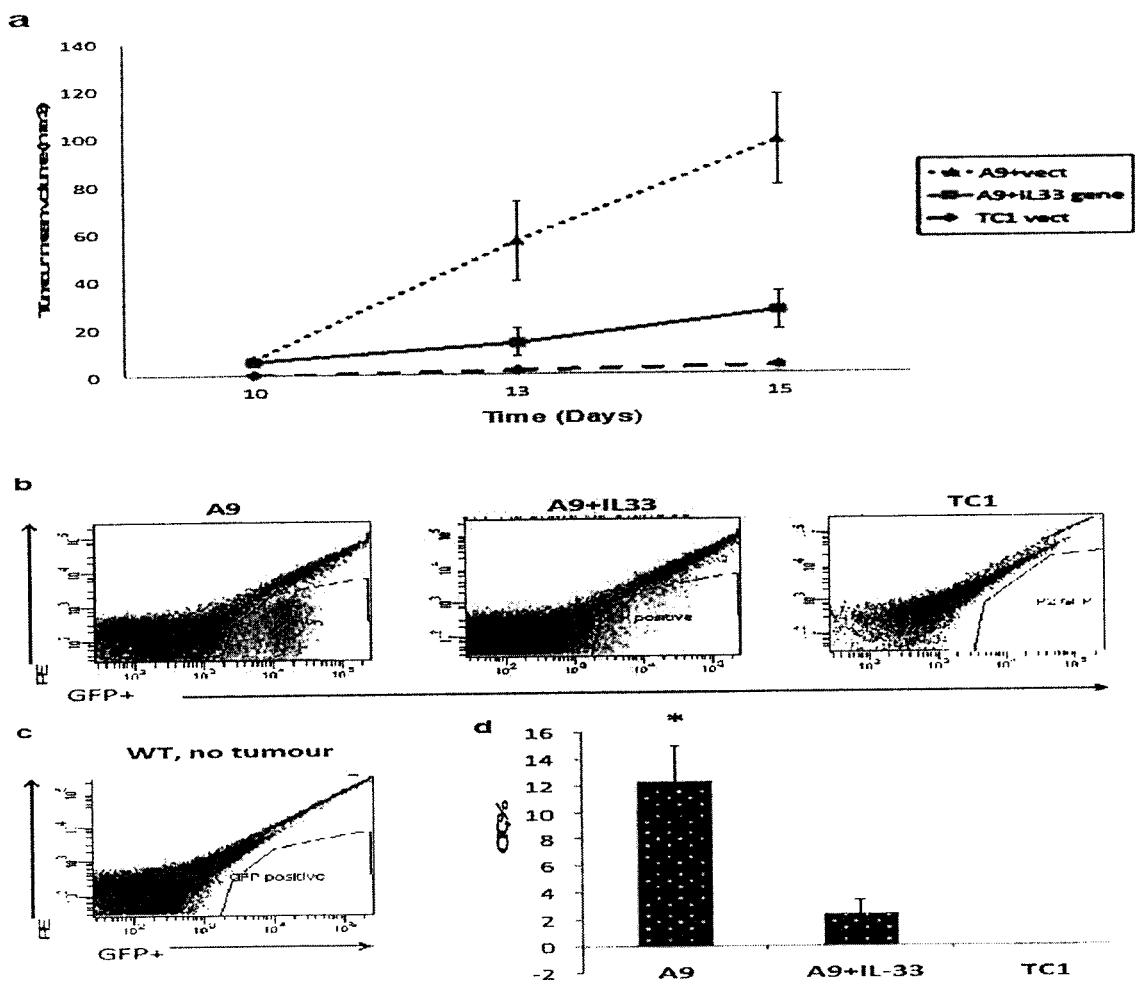

FIG. 68: IL-33 gene-complementation suppresses tumor growth rate in vivo and inhibits metastatic spread of tumor cells in a mouse model. (a) Stable transfection of IL-33 gene into A9 cells resulted in significantly inhibited tumor formation in mice. GFP-positive circulating tumor cells were isolated from adrenal glands that were distal from initial subcutaneous inoculation, and assessed using flow cytometry: (b) animals injected with A9 cells (left); animals injected with IL-33 expressed metastatic cells (centre); animals bearing primary tumors (right). (c) Adrenal glands were isolated from tumor-free wild type animals to indicate no overlapping autofluorescent cells in flow cytometry gating. (d) Quantification of GFP-positive circulating tumor cells in (b) as a percentage of total cells. Each graph corresponds to the data from one representative animal. *$P<0.05$, comparing GFP-positive CTC cells isolated from the primary (TC1) and metastatic (A9) bearing animals (Student's t-test).

Figure 69:
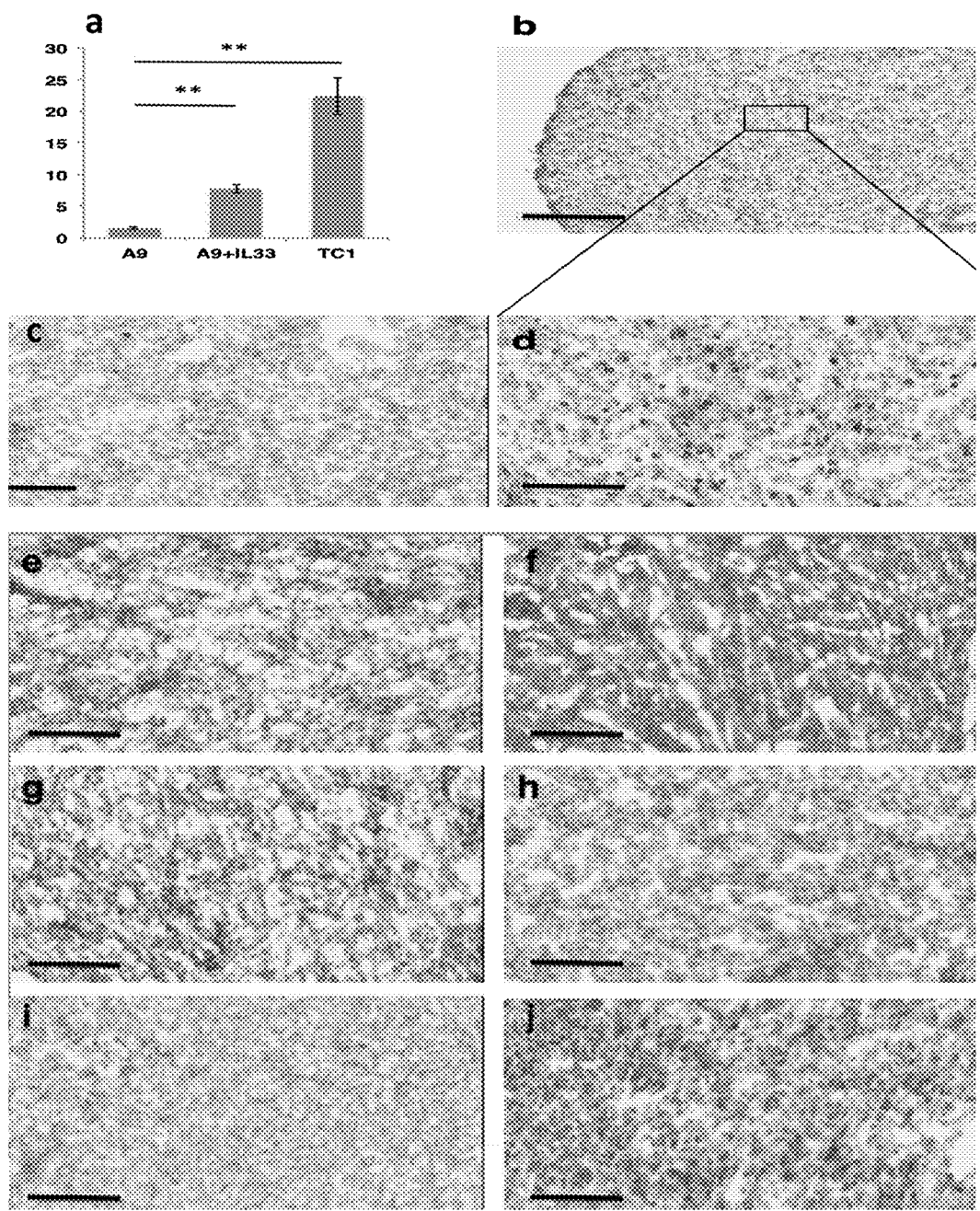

FIG. 69: Genetic complementation of immune evasive tumors shows a phenotypic shift towards immune recognition. (a) To overcome the issue of multi-focality, FACS analysis was used to count TILs. The expression of IL-33 by the tumor skews the TILs towards a cytotoxic T cell response, as a statistically significant increase in the number of CD8-positive cells can be shown in genetically modified (A9+IL-33) tumors versus in metastatic (A9), (Student's t-test), **$P<0.005$. (b-j) Immunohistochemical staining was used to support the FACS analysis. Greater numbers of CD8-positive cells can be seen within the genetically modified (A9+IL-33) tumors (b,d) versus unmodified (A9) tumors (c). IL-33 expression increased MHC-I expression on tumor cell surface; unmodified A9 (e) versus A9+IL-33 (f), thereby increasing antigen presentation. Fewer regulatory T cells are present in IL-33 expressing tumors, as indicated by lower FoxP3 staining; A9 (g) versus A9+IL-33 (h). Increased macrophage response is seen in IL-33 expressing tumors; unmodified A9 (i) versus A9+IL-33 (j). 10 µm thick sections were stained with appropriate antibodies and imaged at 5× (b) or 20× (c-j) magnification.

Figure 70:
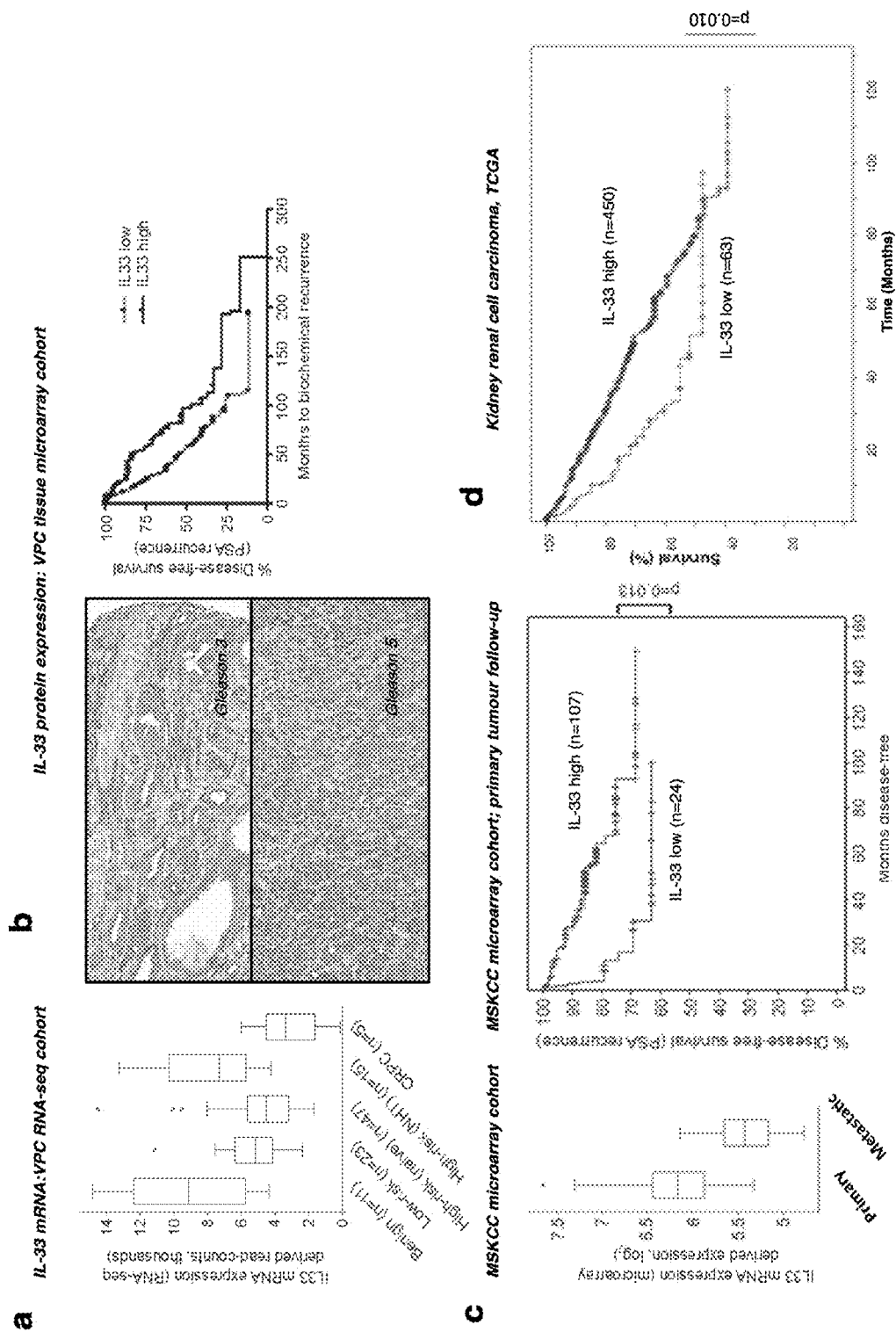

FIG. 70: Reduced IL-33 expression is associated with prostate and kidney renal cell cancer progression. (a) Expression levels of mRNA of IL-33 in castration-resistant prostate cancer (CRPC) are low relative to benign prostate tissue and both low- and high-risk primary tumors. According to the D'Amico Risk classification: low-risk=prostate-specific antigen (PSA) less than or equal to 10, Gleason score less than or equal to 6, and clinical stage T1-2a; high-risk=PSA more than 20, Gleason score equal or larger than 8, or clinical stage T2c-3a. (b) Representative immunohistochemical staining (left panel) showing IL-33 expression in tissue microarrays in prostate tumors of differing Gleason grade (also known as Gleason pattern). The overall Gleason score (3+3) was given for the image on the top and (5+5) for the image on the bottom. 5 µm thick sections were stained and imaged at 20× magnification. The right panel depicts the association of low IL-33 expression in primary tumors at radical prostatectomy, with significantly shorter time to PSA recurrence. (c) IL-33 mRNA expression in 131 case of primary prostate and 37 cases of metastatic prostate tumors confirms an association between low IL-33 expression (z-score relative to normal benign<−2) and time to PSA recurrence in this independent cohort of 131 primary prostate tumors; (d) association between low IL-33 expression (z-score relative to normal benign<−1) and survival of kidney renal cell carcinoma patients.

Figure 71:
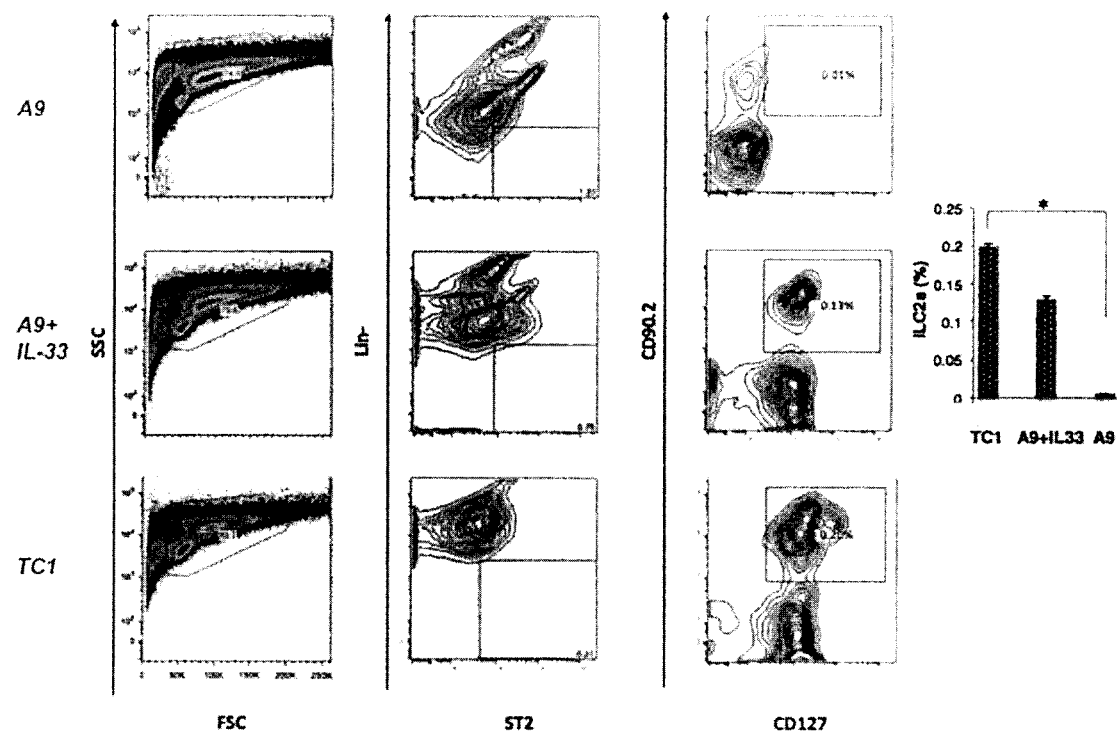

FIG. 71: The frequency of ILC2s is elevated in animals bearing IL-33 expressing tumors.

Figure 72:
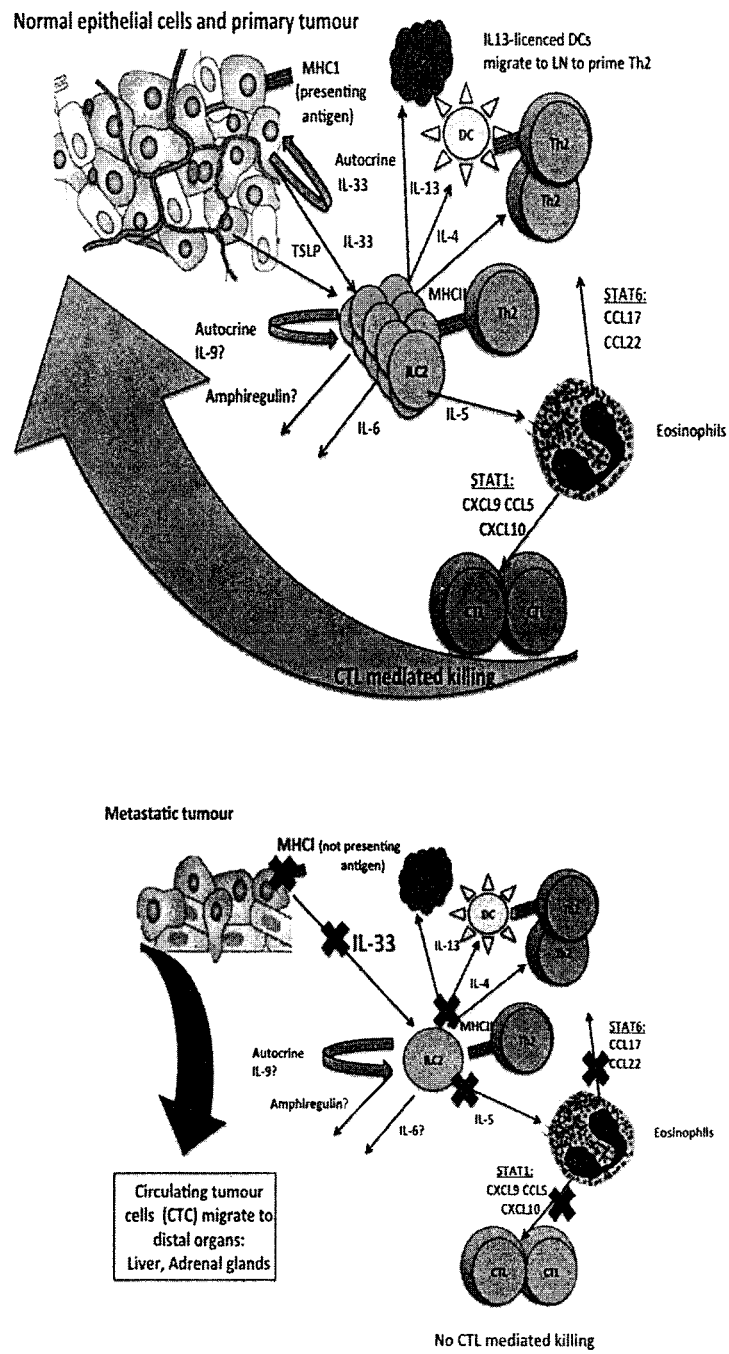

FIG. 72: IL-33-ILC2 axis links the adaptive and innate immune responses together during tumor development. IL-33 expressing tumor environment stimulates the development of ILC2 cells and functionally activates them through the ST2 receptor pathway. Functionally active ILC2s trigger the type 2 effector pathway through secretion of IL-4 and IL-13 together with a direct antigen presentation via MHCII molecules. Through the release of IL-5 by ILC2s and subsequent recruitment of eosinophils, the chemokine profiles of tumor microenvironment is changed to attract CD8+ T cells and to direct the activation of CTL mediated killing and cancer rejection. In metastatic tumors with low IL-33 content the IL-33-ILC2s pathway is halted.

Figure 73:
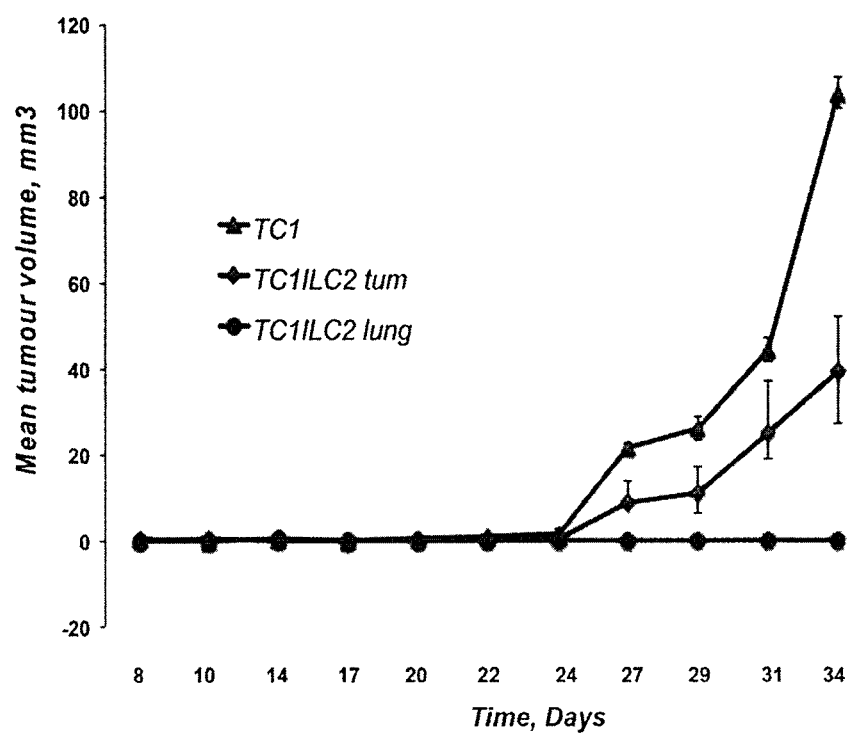

FIG. 73: A complete growth arrest of primary tumor in mice after adoptive transfer of ILC2s isolated from lungs.

Figure 74:
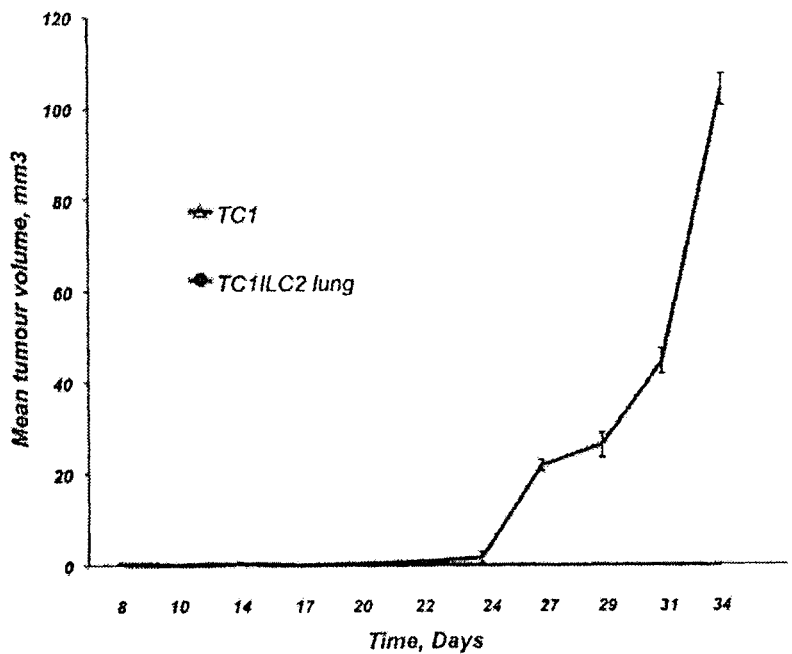

FIG. 74: Immune therapeutic study: ILC2s can boost the anti-cancer response in vivo. Adoptive transfer of activated ILC2s was able to suppress primary (TC-1) tumor growth rate: (blue) primary tumor growth rate without IV injection of ILC2s and a complete growth arrest of primary tumors (green) after IV injection of ILC2s isolated from donor lungs. Tumor volume was measured at initial site of subcutaneous injection.

Figure 75:
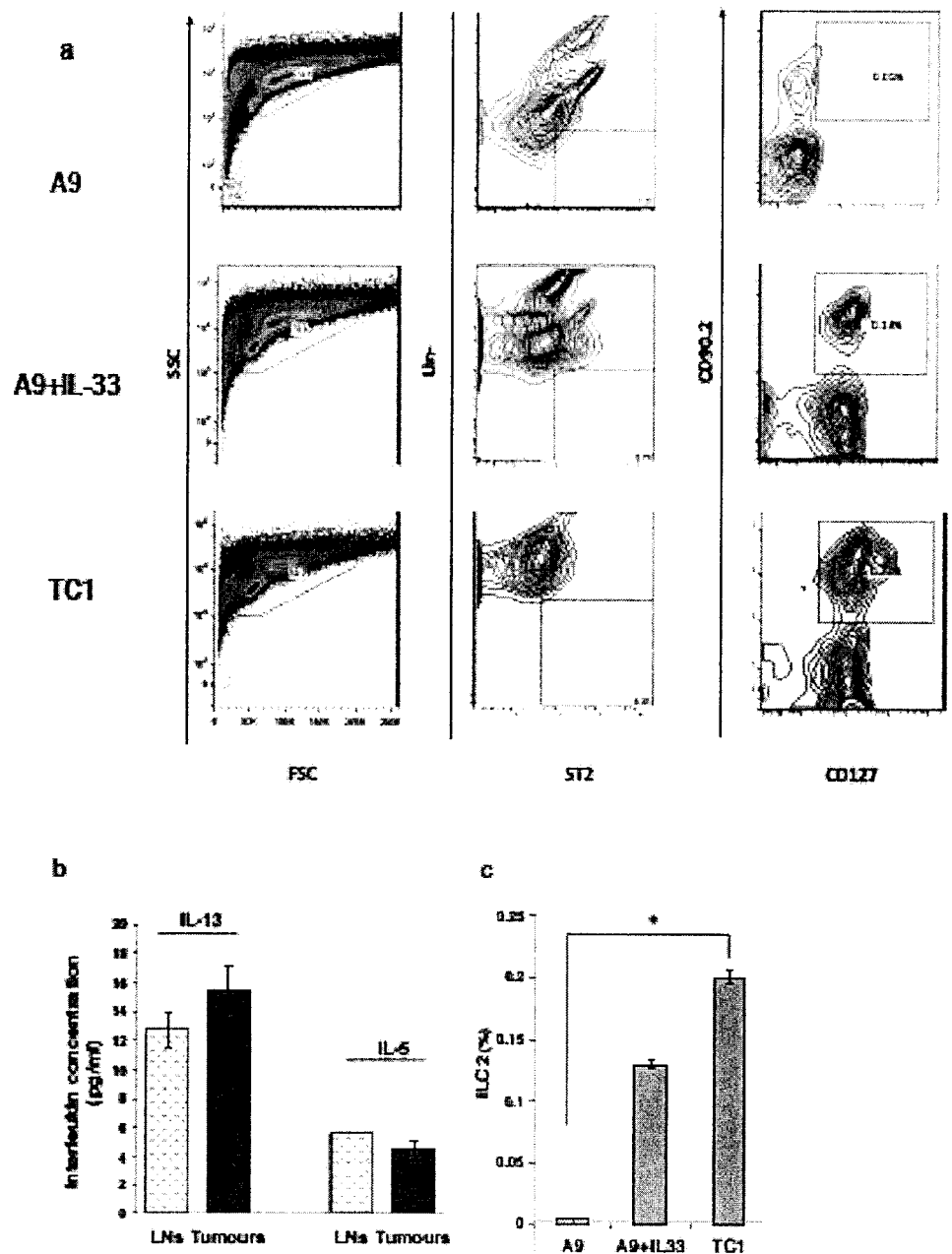

FIG. 75: The frequency of ILC2s is elevated in animals bearing primary tumors and metastatic tumors stably transfected with IL-33 gene. (a) ILC2s from tumors were sorted by FACS as LinST2+CD127+CD90.2+ cells. ILC2 detection strategy included: first gating on lineage-negative (Lin−) and (ST2)-positive lymphocytes with further analysis for CD90.2+ and CD127+ expression following quantification of ILC2s isolated from tumor tissue. (b) ILC2s isolated from disaggregated lymph nodes and primary tumor tissues appeared to be fully functional, and retained the ability to secrete IL-13 and IL-5. (c) The percentage of ILC2 cells that could be isolated from tumors went up in direct relation to the ability of the tumor cells to secrete IL-33. This difference was statistically significant between the number of ILC2 cells isolated from the primary and metastatic tumors (*P Student's t-test). The ranges represent the data from animals within each tumor group, where lymph nodes (n=8 animals) and tumors (n=4 animals).

Figure 76:
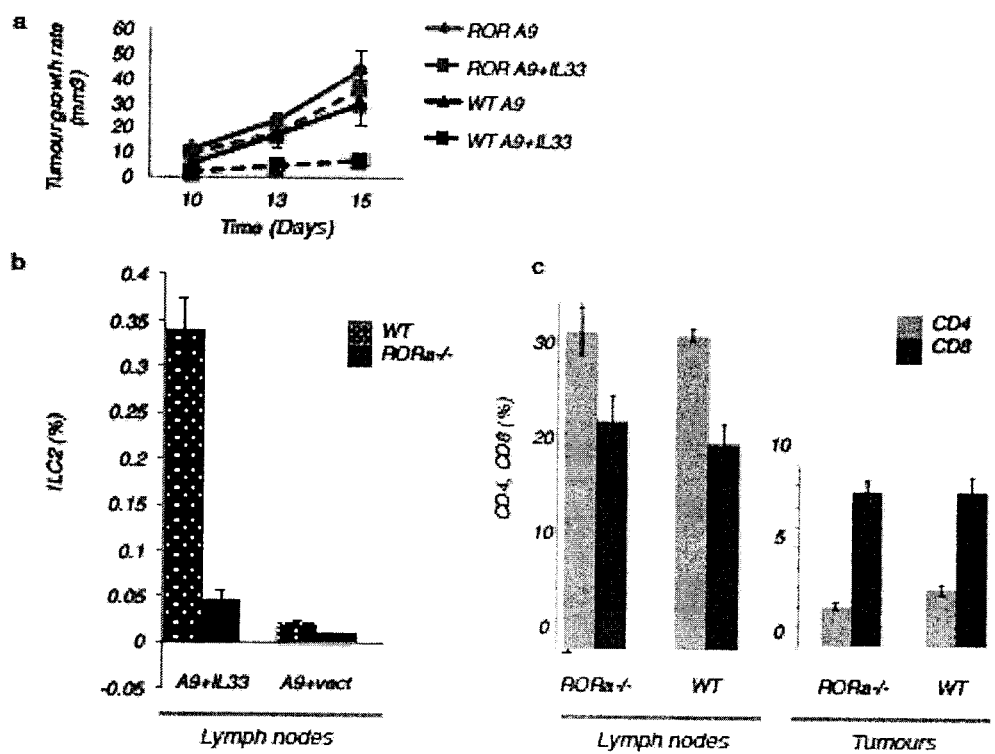

FIG. 76: IL-33 can modify tumor progression and support the conclusion that ILC2s participate in cancer immune-surveillance through RORα-IL-33-ILC2 axis. Mice were transplanted with either RORα−/− or wild type bone marrow, and after successful bone marrow repopulation, metastatic tumors with and without IL-33-expression were injected into these chimeric mice. (a) Stable transfection of IL-33-gene into A9 cells resulted in significantly inhibited tumor formation in WT mice when compared to RORα−/− chimeras. (b) The numbers of ILC2 cells found in neighboring lymph nodes were significantly lower in RORα−/− mice compared to wild type chimeras. (c) RORα deficiency had no effect on the ratio of CD4+/CD8+ lymphocytes in response to A9+IL-33 tumors.

Figure 77:
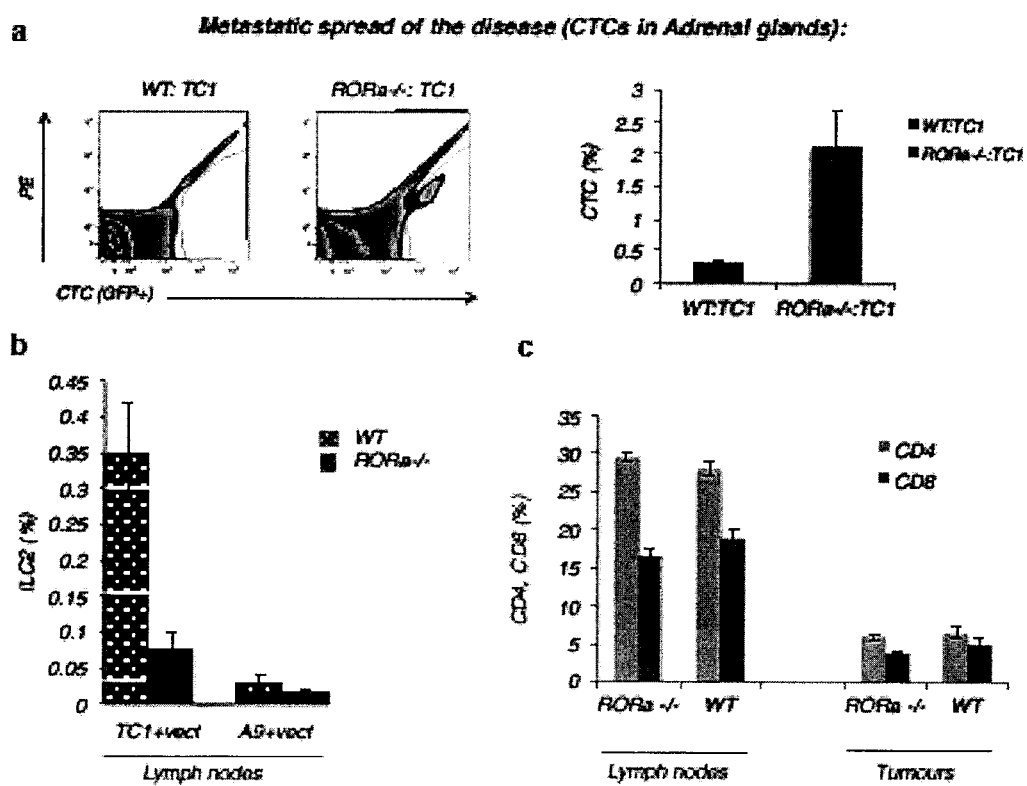

FIG. 77: RORα is an important transcription regulator, which affects the metastatic spread of the disease. (a) A population of circulating tumor cells was detected in adrenal glands of RORα−/− chimeric animals bearing tumors with local growing potential. (b) The numbers of ILC2 cells found in neighboring lymph nodes were significantly lower in RORα−/− mice compared to wild type chimeras. (c) RORα deficiency had no effect on the ratio of CD4+/CD8+ lymphocytes in response to A9+IL-33 tumors.

Figure 78:
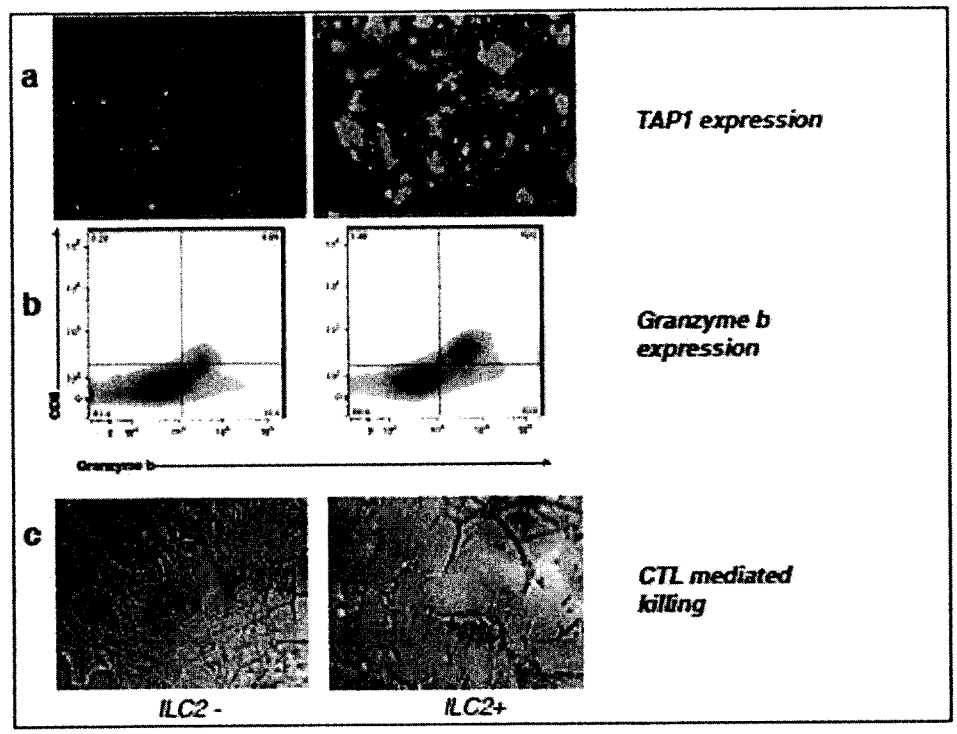
Figure 79:
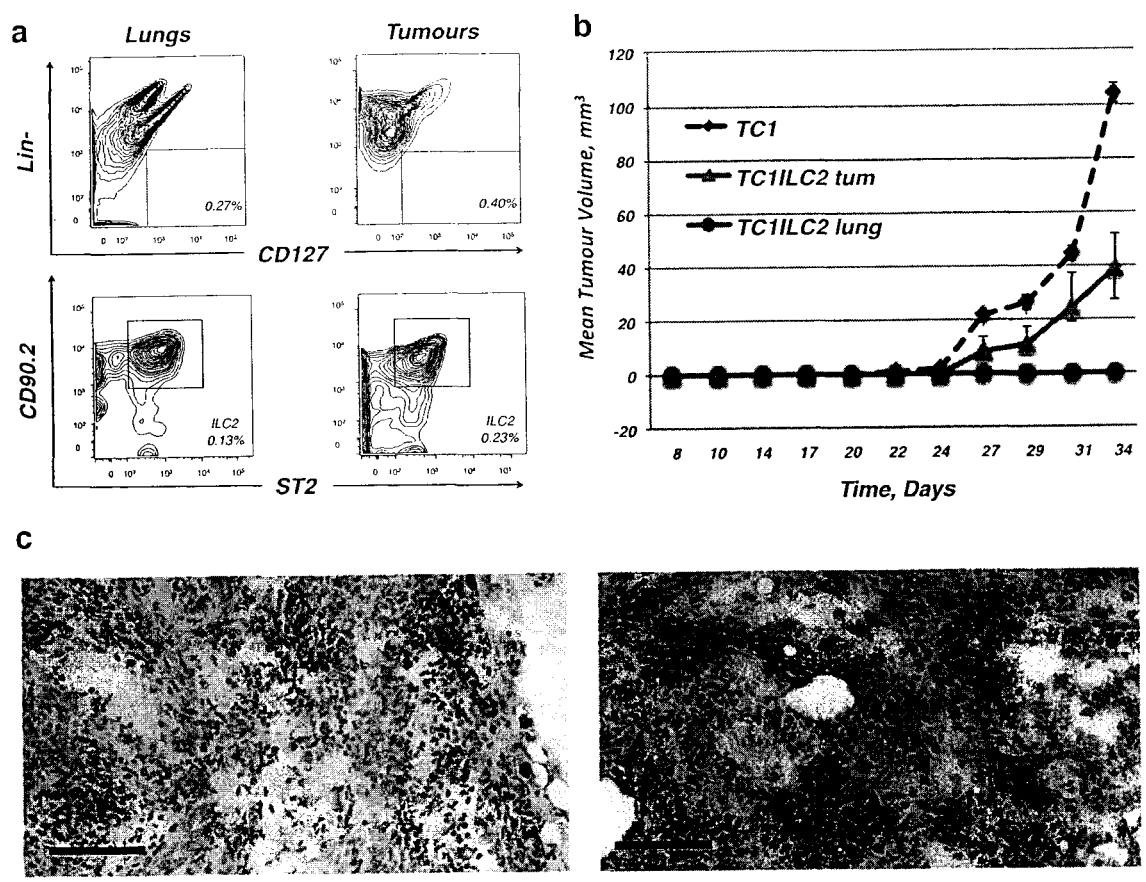

FIG. 78: Impact of ILC2s on specific cytolytic T cell effector mechanisms. Co-culture of metastatic murine prostate TAP-1 low carcinoma cells (LMD) and CD8 T cells with ILC2s (right panel) or without ILC2 cells (left panel): (a) TAP-1 expression level in LMD cells before (left) and after (right) activation with ILC2 cells; (b) Granzyme b expression by CTL cells before (left) and after (right) activation with ILC2 cells; (c) CTL mediated killing of tumor cells FIG. 79: (a) Gating strategies to select ILC2 cells for the Adoptive transfer: isolation from donor lungs and donor tumors (TC1 tumor-bearing mouse). (b) A complete growth arrest of primary tumors in mice after adoptive transfer of ILC2s isolated from donor-lungs. (c) Eosinophil recruitment into tumor tissue is induced by ILC2s.

Figure 80:
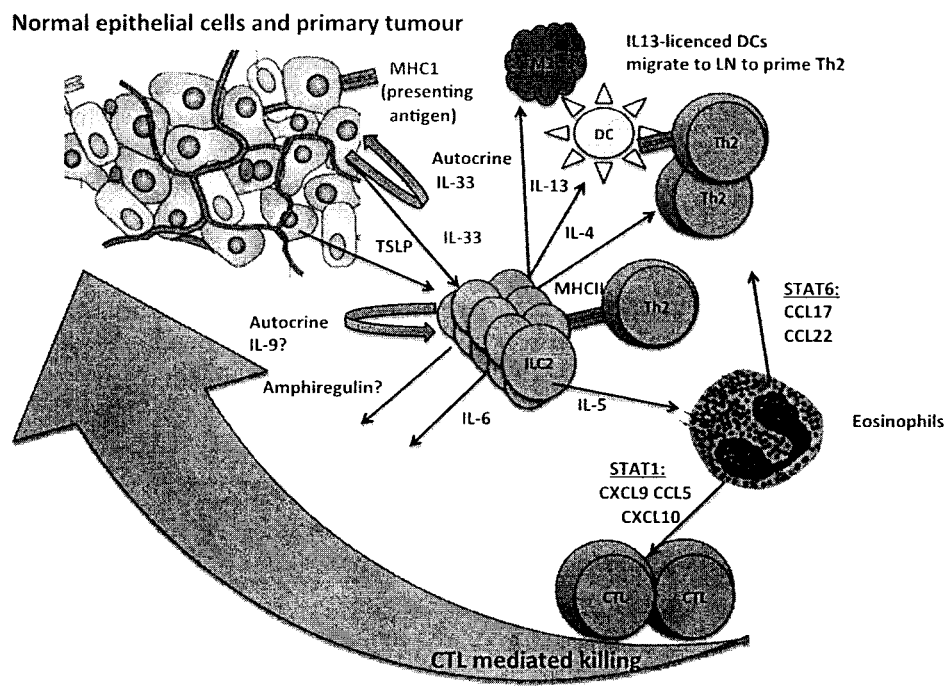

FIG. 80: IL-33-ILC2 axis links the adaptive and innate immune responses together during tumor development. IL-33 expressing tumor environment stimulates the development of ILC2 cells and functionally activates them through the ST2 receptor pathway. Functionally active ILC2s alter the tumor microenvironment triggering innate and adaptive immune responses. ILC2s recruit dendritic cells through IL-13 production and Th2 cells through direct antigen presentation via MHCII molecules. Through the release of IL-5 by ILC2s and subsequent recruitment of eosinophils, the chemokine profiles of tumor microenvironment is changed to attract CD8+ T cells and to direct the activation of CTL mediated killing and cancer rejection. In metastatic tumors with low IL-33 content the IL-33-ILC2 pathway is halted

DETAILED DESCRIPTION

The present invention is based on the discovery of the role of interleukin 33 (IL-33), interferon induced protein 44 (IFI44) and type 2 innate lymphoid cells (ILC2s) in cancer progression. In particular, the invention is based on the discovery that IL-33 and IFI44 are down regulated or mutated in metastatic tumors compared to benign or primary tumors and the growth of metastatic tumors and the frequency of circulating metastatic tumor cells (CTC) are reduced when the tumors are genetically engineered to express IL-33 or IFI44. The invention is further based on the discoveries that ILC2s aid in immune recognition of cancers in vivo, limit metastasis and tumor growth rate.

Accordingly, the present invention provides methods and compositions for inhibiting cancer progression and/or for providing treatment of cancer. Inhibition of cancer progression and/or cancer treatment includes but is not limited to inhibition of tumor growth, stimulation of tumor regression, enhancement of immune recognition of tumor cells, stimulation of anti-tumor immunity, treatment of the primary tumor, prevention and/or treatment of tumor metastases. Also provided are methods of stimulating antigen presentation by enhancing MHC-I and/or TAP-1 expression. In addition, methods of increasing tumor infiltrating immune cells (TILs such as ILC2 cells) are provided.

A worker skilled in the art could readily determine which types of cancers can be treated. The cancer may be a solid tumor. In certain embodiments, the cancer is a sarcoma, carcinoma or lymphoma. In certain embodiments the cancer is selected from a breast cancer, ovarian cancer, liver cancer, renal cancer, melanoma, colorectal cancer, head and neck squamous cell cancer, cervical cancer or prostate cancer. In certain embodiments, the cancer is a leukemia or other hematological cancers.

In certain embodiments, there is provided methods and compositions for inhibition of cancer progression and/or treatment of cancer by enhancing expression and/or activity of IL-33 and/or IFI44.

IL-33 and/or IFI44 may be provided as polypeptides, as a polynucleotide which expresses the protein, as a vector or a cell that expresses the polypeptide. The nucleic acid and polypeptide sequences of IL-33 and IFI44 are known in the art. Appropriate promoters, including constitutive and tumor specific promoters, and expression vectors would be apparent to a worker skilled in the art. It would also be apparent to a worker skilled in the art that such vectors may be administered directly to an individual. A worker skilled in the art would readily appreciate that the polypeptides, polynucleotides or vectors may be administered directly into a tumor site or distal to a tumor site (including but not limited to intravenous, subcutaneous or intraperitoneal administration).

Alternatively cells, either autologous or heterologous cells, may be engineered with a polynucleotide or vector ex vivo and the cells provided to the individual. In certain embodiments, the cells are immune cells, including but not limited to ILC2s. In other embodiments, the cells are tumor cells.

Accordingly, in certain embodiments, there is provided compositions comprising and methods utilizing IL-33 and/or IFI44 polypeptides or active fragments thereof. In other embodiments, there is provided polynucleotides, expression vectors and/or cells which express IL-33 and/or IFI44, or active fragments thereof. The polypeptides, polynucleotides, expression vectors and/or cells may be administered as a pharmaceutical composition with a pharmaceutically acceptable diluent or carrier.

In other embodiments, there is provided compositions and methods for inhibition of cancer progression and/or treatment of cancer by stimulating the activity and/or expanding the numbers of ILC2s. This may be done in vivo by administration of an ILC2 regulator (or a polynucleotide or vector encoding an ILC2s regulator) such as IL-33, interferon induced protein 44 (IFI44) and/or MR1.

In certain embodiments, there is provided a method of inhibiting metastatic spread of circulating tumor cells to distal organs with IL-33, IFI44 and/or ILC2 cells.

In certain embodiments, there is provided compositions and methods for inhibition of cancer progression and/or treatment of cancer by administering ILC2 cells. In certain embodiments, the ILC2 cells are autologous cells or heterologous. The cells may be isolated from various tissues including but not limited to lung tissue or tumor tissue. Following isolation, the cells are optionally stimulated or modified ex vivo. The ILC2 cells may be stimulated by co-culture with other cells and/or by culturing with one or more stimulatory molecules, such as various cytokines. Ex vivo modification may also include genetic modification of the ILC2s. In certain embodiments, the ILC2s have been modified to express immune modulatory molecules including but not limited to cytokines. In certain embodiments, the ILC2s have been genetically modified to express IL-33 and/or IFI44. In certain embodiments, the ILC2 cells have been genetically modified to express markers. In certain embodiments, the ILC2s have been genetically modified to express TCR, including but not limited to tumor antigen specific TCRs or Ig. In certain embodiments, the ILC2s have been genetically modified to expression CAR receptors. In certain embodiments, the ILC2s have been genetically modified to expression CAR receptors.

IL-33 (IL-33 polypeptide, polynucleotide encoding the IL-33 or vectors encoding IL-33), IFI44 (IFI44 polypeptide, polynucleotides encoding IFI44 or vectors encoding IFI44) and ILC2s may be used alone or in combination with each other and/or with other therapies which stimulate immunity, treat cancer and/or inhibit cancer progression. Other therapies include but are not limited to other cytokines (including but not limited other cytokines in the ILC2 axis such as IL-9 and IL-21), cellular therapies (including but not limited to administration of immune cells such as ILC2s), vaccine therapies, and chemotherapeutics.

Specific non-limiting examples of therapies that IL-33 and/or IFI44 and/or ILC2s may be used in combination with include but are not limited TNF alpha; interleukin-21; interleukin-13; a combination of interleukin (IL)-4, IL-5, IL-9 and IL-13; a combination of PD-1, CTLA-4, PDL-1; interferon, including but not limited to interferon alpha, beta or gamma; GM-CSF; G-CSF; HDACi; HATs; methylation inhibitors; T cells including but not limited to CAR T Cells, autologous T Cells, autologous T Cells transducer with specific TCRs, autologous B Cells, dendritic cells subsets, antigens of interest including but not limited to viral, bacterial and tumor antigens; antibodies including but not limited to antibodies targeting tumor antigens such herceptin; other biological therapies; hematopoietic stem-cell transplantation; natural killer cells; Toll receptor agonists; chemokines; anti-angiogenic molecules; other cytokines used in immune therapy including but not limited to IL-2; chemotherapies; viral vectors; oncolytic viruses; adjuvants; cytotoxic agents; and therapies which deplete regulatory T cells.

In certain embodiments, there is provided a method of modulating immunity and/or an immune response by modulating expression and/or activity of IL-33 and/or IFI44. In certain embodiments, there is provided a method of modulating antigen presentation by modulating expression and/or activity of IL-33 and/or IFI44. In certain embodiments, there is provided a method of modulating MHCI expression by modulating expression and/or activity of IL-33 and/or IFI44.

In certain embodiments there is provided a method of enhancing immunity and/or an immune response by enhancing expression and/or activity of IL-33 and/or IFI44. In certain embodiments, there is provided a method of enhancing antigen presentation by enhancing expression and/or activity of IL-33 and/or IFI44. In certain embodiments, there is provided a method of enhancing MHCI expression by modulating expression and/or activity of IL-33 and/or IFI44. Non-limiting examples of methods to enhance expression and/or activity a polypeptide interest include administration of the polypeptide of interest, administration of a nucleic acid or vector which encodes the polypeptide of interest or administration of one or more molecules which enhance expression of the polypeptide of interest.

In alternate embodiments, there is provided a method of decreasing immunity and/or an immune response by inhibiting expression and/or activity of IL-33 and/or IFI44. In certain alternate embodiments, there is provided a method of decreasing antigen presentation by inhibiting expression and/or activity of IL-33 and/or IFI44. In certain embodiments, there is provided a method of decreasing MHCI expression by inhibiting expression and/or activity of IL-33 and/or IFI44. Non-limiting examples of methods to inhibit expression and/or activity a polypeptide interest include administration of an antagonist, including but not limited to antibodies, against the polypeptide of interest and nucleic acids such as antisense oligonucleotides or siRNA which target the nucleic acids which encode the polypeptide of interest.

In certain embodiments, there is provided a method of modulating immunity and/or an immune response by modulating ICL2 cell numbers and/or activity. In certain embodiments there is provided a method of enhancing immunity and/or an immune response by increasing ICL2 cell numbers and/or activity. In certain embodiments there is provided a method of inhibiting immunity and/or an immune response by decreasing ICL2 cell numbers and/or activity.

Diagnostic Methods:

Microarray analysis demonstrates that gene expression differs between metastatic and non-metastatic cell lines. Differences in expression of extracellular matrix remodelling genes and genes involved in immune response may be observed in metastatic and non-metastatic cells. For example, microarray analysis demonstrated a number of up-regulated genes responsible for matrix remodeling (MMP2, MM9, MMP10, MMP13) and down-regulated immune- and inflammation-related genes in a metastatic cell line (such as prostaglandin and leukotriene, interleukin (IL)-related genes (e.g., IL-11ra1, IL-13ra, IL15, IL-33), tumor necrosis factor and caspase families (TNFsf9, Casp7, Casp12), antigen processing and presentation (e.g., H2-K1, H2-DMb1, H2-Q5, H2-Q6, TAP1, TAP2, Tanasin, LMP2)).

Accordingly, in certain embodiments, there is provided a method of distinguishing metastatic cells from non-metastatic cells by determining expression of one or more genes. In other embodiments, there is provided a method for determining progression to metastatic disease by determining expression of one or more genes. These genes may be genes responsible for matrix remodeling and immune- and inflammation-related genes. In certain embodiments, genes responsible for matrix remodeling are up-regulated and immune- and inflammation-related genes are down-regulated in metastatic disease.

The level of IL-33, IFI44 and various APP genes (such as MR1) appear to be down in metastatic lung and prostate carcinomas compared to benign or primary tumors. Accordingly, in certain embodiments, there is provided a method for determining progression to metastatic disease by determining expression of IL-33, IFI44 and/or various APP genes (such as MR1). In some embodiments, there is provided a method of diagnosing progression to a metastatic form of prostate cancer or metastatic lung cancer by determining level of expression of IL-33, IFI44 and/or various APP genes (such as MR1). In certain embodiments, expression of IL-33 is determined. In certain embodiments, expression of IFI44 is determined. In certain embodiments, expression of IL-33 and IFI44 is determined.

In certain embodiments, there is provided a method of determining clinical outcome of a cancer patient by determining expression of one or more genes. In specific embodiments, there is provided a method of determining clinical outcome of a cancer patient by determining expression of IL-33, IFI44 and/or MR1. In certain embodiments, expression of IL-33 is determined. In certain embodiments, expression of IFI44 is determined. In certain embodiments, expression of IL-33 and IFI44 is determined. In other embodiments, patient status is monitored other time by monitoring changes in expression of IL-33, IFI44 and/or MR1 over time. In certain embodiments, changes in expression of IL-33 are monitored over time. In certain embodiments, changes in expression of IFI44 are monitored over time. In certain embodiments, changes in expression of IL-33 and IFI44 are monitored over time.

In the absence of IL-33 and/or ILC2s in a metastatic tissue, eosinophils do not enter the metastatic tumor tissue but accumulate adjacent to the periphery of the malignant tumor. Accordingly, in certain embodiments of the present invention, there is also a method of determining prognosis, disease progression, including but not limited to progression to metastatic disease, and/or clinical outcome based on the presence of eosinophils in/or surrounding a tumor. Methods of identifying eosinophils are known in the art and include various stains such as Hansel's stain, Wright-Giemsa stain, and eosinophil specific antibodies such as Eosinophil Antibody (BMK-13) from Novus Biologicals.

To gain a better understanding of the invention described herein, the following examples are set forth. It will be understood that these examples are intended to describe illustrative embodiments of the invention and are not intended to limit the scope of the invention in any way.

Example 1: Identifying Inflammation Related Genes Correlating with Metastasis

Summary:

Type 2 innate lymphoid cells (ILC2s) potentiate adaptive immune responses and are one of the first responders to the pro-inflammatory "alarmin" interleukin 33 (IL-33) in the tissue microenvironment. Here we show that IL-33 is down-regulated or mutated in metastatic forms of mouse and human carcinomas compared to their benign or primary syngeneic forms. We demonstrate that the growth of metastatic tumors and the frequency of circulating metastatic tumor cells (CTC) are reduced when the tumors are genetically engineered to express IL-33. Finally, we show that tumor growth rate was significantly increased in mice lacking ILC2s as compared to in wild type (WT) animals. These observations demonstrate that IL-33 can modify metastatic spread of the disease and demonstrate a role for ILC2s in cancer immune surveillance through RORα-IL-33-ILC2 axis.

Results:

Array Analysis Identifies Inflammation Genes Correlating with Metastasis:

The immune system limits the development of tumors unless the tumor cells undergo chromosomal alterations, which cause a phenotypic shift to an immunologically non-recognizable form, resulting in malignancy. The metastatic gene signature is a combination of metastasis progression genes acting together in contributing to the malignant potential of tumors. To better understand potential MHC-I loss and mechanism of tumor progression to metastases, a comparative microarray was conducted profiling of gene expression levels in antecedent non-metastatic and metastatic cell lines of murine prostate and lung cancer. A murine lung tumor model represents the class of cells spontaneously acquired MHC-I-loss phenotype due to immunoselection from the primary tumor cells, but thought to correlate with tumor aggressiveness and metastases. A murine prostate tumor model represents a model of cancer progression with concordantly down-regulated MHC-I level during the metastatic process. As far as we are aware, no one has directly compared whether immunoselected MHC loss and natural MHC loss due to metastasis modulate similar gene expression or what this means for understanding cancer biology.

mRNAs were isolated from both model systems and sent to the microarray centre at the University Health Centre in Toronto, Canada where they were hybridized to a 28005 Two-Color Agilent microarray with a total of 55821 probes. Data from the Agilent chip was imported to GeneSpring GX and normalized using the recommended Agilent's spatial detrending Loess function. The data was then filtered to remove any probes that showed a lack of signal in both channels. Probes in the upper 80$^{th}$ percentile of the intensity distribution were kept for further analysis. Genes were then marked as potential regulators of metastasis, if they showed a fold change of at least 2 between the non-metastatic and MHC-I loss or metastatic forms of both prostate and lung cancers.

Figure 1:
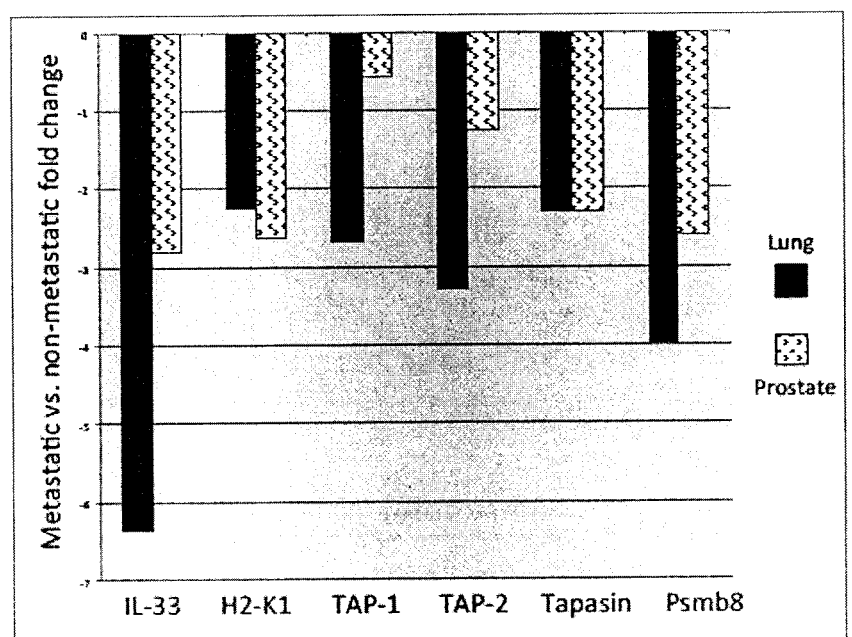
FIG. 1: IL-33 and various antigen presenting protein (APP) genes are down regulated in murine metastatic lung and prostate carcinomas. Metastatic lung carcinoma (A9, metastatic clones that were derived from the TC-1 tumor cells) gene expression was compared to primary, non-metastatic tumor (TC1). Metastatic prostate carcinoma (LMD) gene expression was compared to primary, non-metastatic tumor (PA). Microarray data was obtained using an Agilent chip and the GeneSpring GX software.

To further narrow the list of significantly different probes, genetic ontology (GO) analysis was performed using a Benjamini and Yuketiele hypergeometric corrected test statistic to determine the most significantly affected GO IDs. Extracellular matrix remodelling genes and genes involved in immune response were found to be the most affected group of gene products between MHC-I loss or metastatic and non-metastatic cell lines, supporting the idea that genes that were indicative for metastasis and immune evasion were expected to come from these ontologies. In particular, microarray analysis demonstrated a significant number of up-regulated genes responsible for matrix remodelling (MMP2, MM9, MMP10, MMP13) and down-regulated immune- and inflammation-related genes. There were many well-known interferon (IFN)-induced genes (e.g. IRF1, IRF5, IRF7, IRF9, IFI27, IFI44, PSMB8, PSMB9, IFIT2, IFIT1, Igtp), prostaglandin and leukotriene families (Ptgfr, Ptgir, Ptgr1, Ptgis, Ltb4r1), interleukin (IL)-related genes (e.g. IL-11 ra1, IL-13ra, IL15, IL-33), tumor necrosis factor and caspase families (TNFsf9, Casp7, Casp12), as well as genes coding for antigen processing and presentation (e.g. H2-K1, H2-DMb1, H2-Q5, H2-Q6, TAP1, TAP2, Tapasin, LMP2). The level of expression for selected genes was confirmed by real time quantitative reverse transcriptase polymerase chain reaction (qRT-PCR). Aberrant expression of genes in the metastatic/non-metastatic cell lines might provide an avenue to characterize and understand the mechanism of transition from immune recognition to immune evasiveness in tumors. Emphasis was placed on genes known to interact with the APM, those that are involved in novel aspects of inflammation or immunity and those that are induced by interferon (IFN) (FIG. 1).

Figure 2:
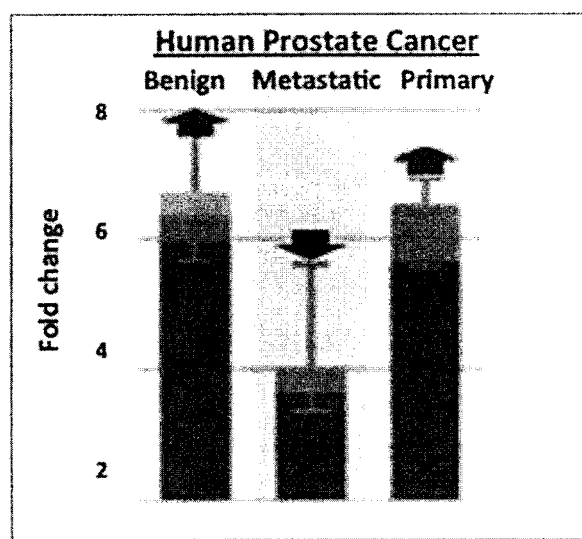
FIG. 2: IL-33 gene expression is down-regulated in human metastatic prostate cancer compared to human benign and primary prostate tumors. The data was obtained from the Gene Expression Atlas created by the European Bioinformatics Institute (access date: Jan. 30, 2013).

Validation in Human Cancers:

Using the data obtained from the Gene Expression Atlas created by the European Biostatistic Institute (access date: Jan. 30, 2013), it was determined that the level of IL-33 gene is down-regulated in human metastatic prostate cancer compared to human benign and primary prostate tumors (FIG. 2). The data from the Gene Expression Atlas mirrors the agreement between mRNA and protein expression, indicating that the expression level of IL-33 could potentially be used as a prognostic marker for prostate tumor transition to its metastatic form.

IL-33 Contributes to TAP-1 and H2-Kb Expression/Signaling:

Down-regulation of TAP-1/MHC-I has been shown in literature as a primary indicator for rapid tumor progression and metastasis in human and, therefore, has been used as the primary indicator in this study. To investigate the effects of IL-33-gene on TAP-1/MHC-I expression, the gene was introduced into the transporter TAP-1-deficient murine lung carcinoma cell line (A9), which has MHC-I loss phenotype and thus immune evasive. Gene expression construct with a full-length cDNA for IL-33 has been produced using the pIRES2-EGFP vector. Stably transfected clones were isolated from GFP-positive cells and used for the study. The immunomodulatory activities of selected gene candidate were first analyzed based on mRNA expression. We isolated mRNA from transfectants and performed reverse transcription-PCR (RT-PCR) using TAP-1 specific primers. Among mRNA encoding the eight different gene-candidates analyzed, IL-33 transcript had the highest expression (FIG. 3a). The overexpression of IL-33 was confirmed by ELISA and immunoblot analysis and studied the changes of TAP-1 and H2-K1 protein expression level in MHC-I loss carcinoma A9-transfectants. Western Blot analyses confirmed the increase of TAP-1 and H2-K1 production in study model (FIG. 3b). Furthermore, to test whether increased TAP-1 expression would be able to induce H2-K1 cell-surface representation, we used Flow Cytometry analysis. The fluorescent signal was significantly shifted after IL-33 transfection comparing to negative control possibly due to the restoration of APM functionality (FIG. 3c). Collectively, these findings indicated that transfection of IL-33 gene can induce TAP-1 and H2-Kb expression on mRNA, protein and molecular levels. It may infer that the gene participates in a pathway or pathways leading to TAP-1 and H2-Kb expression/signaling.

Figure 4:
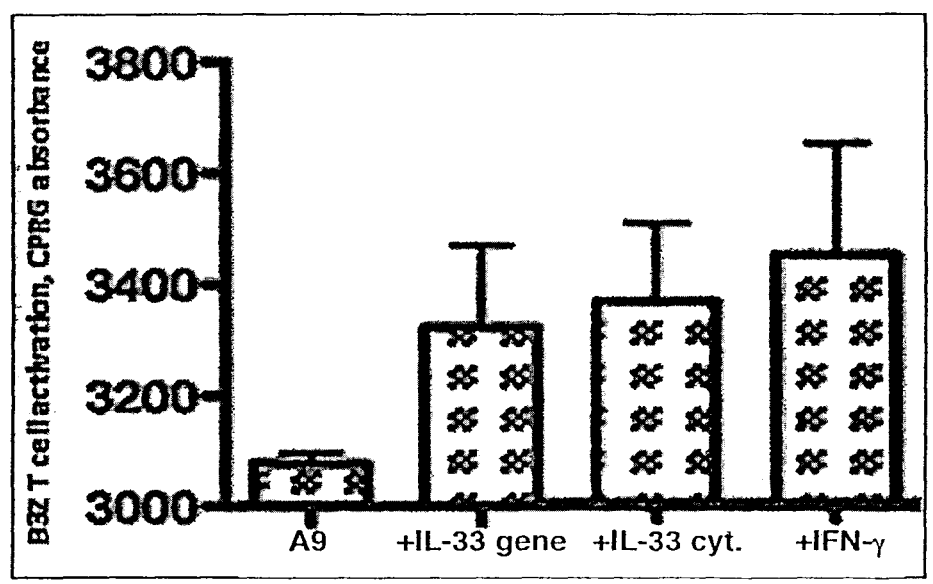
FIG. 4: The expression of the IL-33 within metastatic murine lung carcinoma cells (A9) enhanced antigen-specific recognition by B3Z T-cells. Furthermore, the addition of exogenous IL-33 cytokine protein induced activation of OVA-specific B3Z T-cells. The addition of IFN-γ was used as a positive control.

IL-33 Complements Immune Recognition of Metastatic Tumors:

To further evaluate the functionality of IL-33 induced changes, the ability of transfected and IL-33-cytokine treated A9 cells to present the H2-K1-restricted ovalbumin epitope OVA (257-264, SIINFEKL; SEQ ID NO. 9) was assessed. After incubation of cells with soluble OVA (257-264) for 16 h, we cultured them with B3Z, a T cell hybridoma that is activated by the recognition of H-2K$^b$ in association with OVA (257-264; SEQ ID NO. 9). In the presence of IL-33 cytokine, A9 cells had a higher abundance of H2-K1-OVA (257-264; SEQ ID NO. 9) complexes than did IL-33 transfectants. This resulted in a greater capacity for T cell priming and activation (FIG. 4), perhaps, due to the higher importance/activity of extra-cellular form of the IL-33 protein comparing to its intra-nuclear form. These data demonstrated that the IL-33 improves immune recognition of MHC-I loss lung carcinoma A9.

Figure 5:
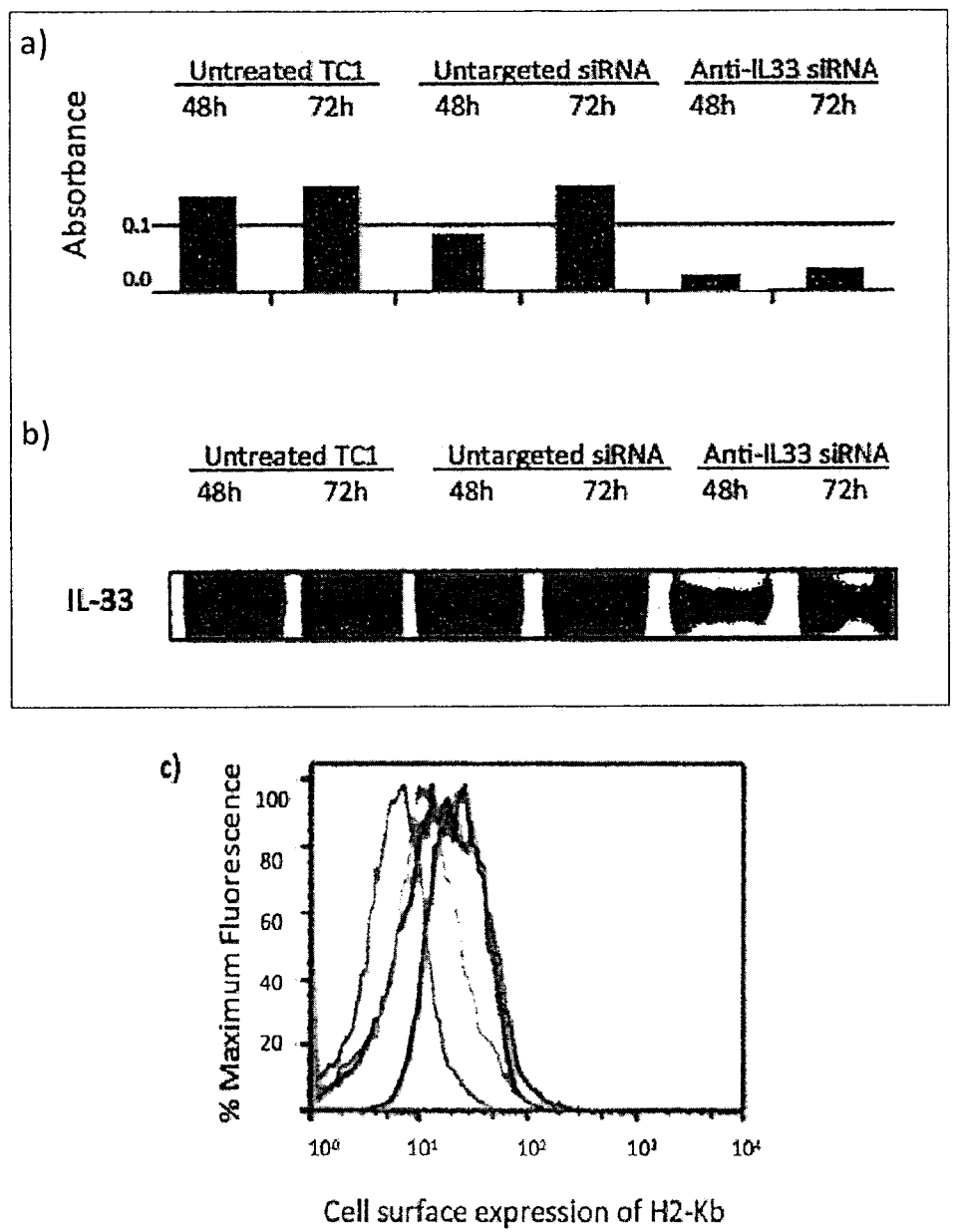
FIG. 5: Down regulation of IL-33 gene decreased MHC-I H2-Kb protein expression in primary lung tumor cells. TC-1 primary tumor cells were treated with siRNA targeted against IL-33 for 48 or 72 hrs. a) ELISA assay was used to measure the level of secreted IL-33 in cell supernatants; (Ready-Set-go ELISA kit Cat #88-7333-88 (eBioscience)); b) Western Blot analysis was used to measure the level of IL-33 protein in the cell pellet; ("Nessy-1" mouse antibody to IL-33 (Abcam) ab54385) was used as the primary antibody and Alexa Fluor 689 goat anti-mouse (Invitrogen) A21058 was used as the secondary antibody); c) FACS was used to measure the expression of MHC-I H2-Kb on the surface of tumor cells. TC-1 cells were treated for 72 hrs with siRNA against IL-33 and cell surface expression of MHC-I H2-Kb was assessed by flow cytometry: anti IL-33 siRNA (aqua), untargeted siRNAs (red) or left untreated (blue). Cells were then stained with a PE-conjugated anti-Kb mouse monoclonal antibody (mAb) or left unstained (grey) and analyzed on a FACScan cytometer.
Figure 6:
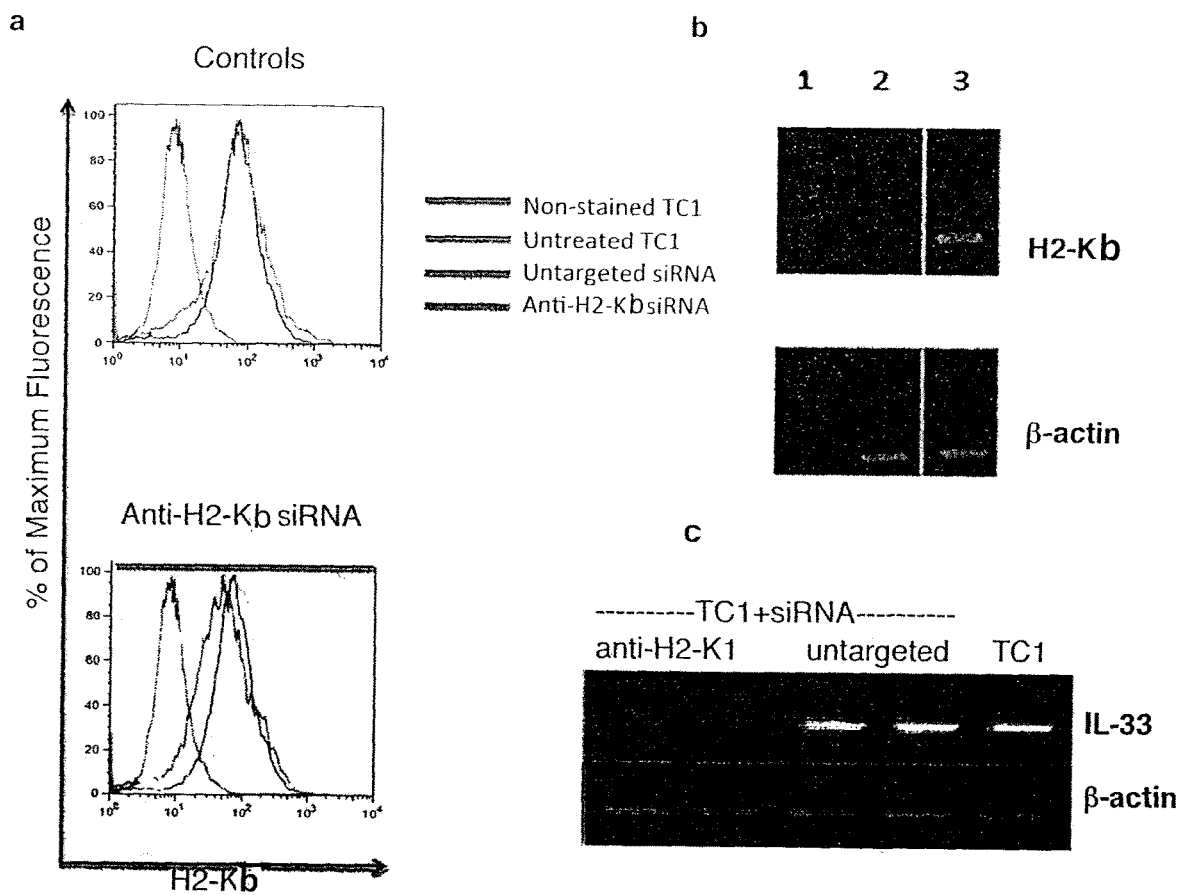
FIG. 6: Down regulation of MHC-I H2-Kb decreased IL-33 gene expression in murine primary lung tumor cells, as well as in H2-Kb–/– mouse. TC1 primary tumor cells were treated with two different siRNAs specifically targeted against mouse MHC-I (H2-Kb) for 96 hrs. Splenocytes isolated from H2-Kb–/– mouse were used to study co-regulation of IL-33 and H2-Kb genes. a) FACS: MHC-I surface expression down-regulated in TC1 cells due to anti-H2-K1 siRNA treatment. b) RT-PCR: Primers against H2-Kb were used to examine the resulting transcription levels of the H2-Kb gene: Lane 1 shows molecular weight control; Lane 2 shows TC1 cells treated with siRNAs against H2-Kb; Lane 3 shows untreated TC1 cells; β-actin was used as loading control. c) RT-PCR: Primers against IL-33 were then used to examine the resulting transcription levels of the IL-33 gene: Lanes 1 and 2 show TC1 cells treated with siRNAs against H2-Kb; Lane 3 show untreated TC1 cells; Lanes 4 and 5 show TC1 cells treated with nonspecific siRNAs; β-actin was used as loading control. d) RT-PCR.

Modulation of Malignant Gene Expression Programming:

To address the role of IL-33 in tumor immune evasiveness, a series of knockdown experiments were conducted using siRNAs specific for IL-33. siRNA targeted against IL-33 were used to assess whether down-regulation of MHC-I expression may occur in non-metastatic cells. Primary tumor cells (TC1) treated with irrelevant siRNA or left untreated were used as controls. We confirmed the down-regulation of IL-33 by ELISA and immunoblot analysis (FIG. 5a) and studied the changes of H2-K1 cell-surface expression level in primary tumor cells (TC1) by flow cytometry. TC1 cells treated with IL-33 directed siRNA had a much lower abundance of H2-K1 complexes than did control treated cells (FIG. 5c). To investigate the effect of MHC-I down regulation on IL-33 expression, siRNAs were used against MHC-I (FIG. 6), as well as splenocytes from H2-K1-/- mouse (FIG. 7). IL-33 appeared to be important for the expression of immune recognizable phenotype in TC1 cell line. Moreover, the data suggested that MHC-I and IL-33 may be co-regulated during the metastatic re-programming of primary tumor revealing the metastatic potential of IL-33 gene.

Metastatic Cells Possess a Mutation in the IL-33 Promoter-Enhancer Regions Leading to LOH:

To further verify the preliminary data, the promoter-enhancer regions of the IL-33, H2-K1 and IFNγ genes in primary TC1 cells and metastatic A9 cells were sequenced and analyzed using Genomatix software, the Eukaryotic Promoter Database (epd.vital-it.ch) and the Computational Biology Research Center Database. Putative binding sites were identified for common transcription factors, including CREB, AP-1, NF-kB, HSF, AML-1a, RORα, GATA (Table 1 below).

IL-33 Gene-Complementation Reverses Metastasis In Vivo:

The finding that IL-33 deficiency resulted in fewer H-2K1 complexes displayed on the cell-surface suggested that these molecules may be co-regulated during metastatic transformation of the primary tumor to its malignant form. To test whether IL-33-induced increase in TAP-1 and MHC-I expression in TAP-1/MHC-I-deficient cell line (A9) could contribute to the anti-tumoral effect of IL-33-gene in vivo, gene-complementation mouse study was performed. TC1 and A9 cells stably transfected with [pIRES2-EGFP] empty vector were used as positive and negative controls respectively. The importance of gene-complementation strategies using several parameters were compared: 1) tumor growth rate; 2) severity of clinical presentation; 3) spread of CTC to distant organs, as a potential to form metastases (FACS); 4) immune response: a) TILs: CD4, CD8, ILC2s; Macrophages, Neutrophils, Tregs (FACS, IHC); b) LNs: CD4, CD8, ILC2s (FACS).

TABLE 1

Promoter analysis of IL-33, MHC-I and IFN-γ has revealed high-scoring binding sites for several common transcription factors. In order to predict putative transcription factor binding sites the Matinspector software from Genomatix website and the database of the Computation Biology Research Consortium (www.cbrc.jp) were used.

| Matrix Family | Family Information | High-Score Sites (85-100) | | | | Scoring Sites (80-85) | | | | Scoring Sites Lower Than 80 | | | |
|---|---|---|---|---|---|---|---|---|---|---|---|---|---|
| | | IL33 | IFI44 | MHCI | IFNg | IL33 | IFI44 | MHCI | IFNg | IL33 | IFI44 | MHCI | IFNg |
| CREB | cAMP-responsive element binding protein | X | X | X | X | | | | | | | | |
| HSF | Heat shock factor | X | XX | X | X | | | | | | | | |
| IRF | IFN regulating factor | | X | | | | | X | | X | X | | |
| STAT | Signal transduser/activator of transcription | | | X | | | X | | | X | | | |
| AML-1a | HSC differentiation | X | X | X | X | | | | | | | | |
| AP | Activator proein | X | X | X | X | | | | | | | | |
| GATA | Cell differentiation | X | X | X | X | | | | | | | | |
| NF-kb | Nuclear factor kappa b | | | X | | | | | | X | X | | X |
| E2F | E2F-myc activator/cell cycle regulator | | | | X | | | | | | | | |
| EGR | Cell growth | | | | X | | | | | | | | |
| RORa | ILC2 development | | | | | X | | X | | | X | | X |
| P300 | Transcription co-activator | | | | | | X | | | | | | |
| HIF | Hypoxia inducible factor | | | | | | | | | | | | X |
| P53 | Tumour suppressor | | | | | | | | | | X | | X |
| MYC | Oncogene | | | | | X | X | X | | | | | |
| RREB Element | Ras-responsive | | | | | | | | | | X | X | |

Moreover, a single base pair mutation $A_{114}G$ on IL-33 promoter of metastatic A9 cell was found within a GATA binding area that affected one IL-33 allele and led to loss of heterozygosity (FIG. 8). Furthermore, the mutation led to the loss of three GATA transcription factors (TFs) that were present in non-mutated DNA sequence (GATA1, GATA2, GATA3) and were not substituted by any other TFs in the area. We assumed that signaling pathways dependent on the TFs GATA and IL-33, such as ILC2s development and function involved in the Th2 immune response, may be adversely affected. In addition, promoter analysis of IL-33, and MHC-I has revealed high-scoring binding sites for RORα TF, which in cooperation with GATA3 and IL-33 orchestrates ILC2s immune response. Moreover, it has been shown in literature that the activation of the orphan nuclear receptor RORα results in a significant decrease of cell proliferation and reduces the invasive and migratory capacities of cancer cells. The molecular mechanisms underlying IL-33 down-regulation in cancer progression are completely unknown, but may lie in RORα related processes that regulate ILC2's development and function. To directly address this we performed bone marrow transplantation experiment to compare the progression of the A9 tumors with and without IL-33-gene complementation in WT and RORα-/- mice.

Stable transfection of IL-33-gene into A9 cells was found to significantly inhibited tumor formation. The mean volume of tumors grown from [A9+IL-33-gene] cells was ~30%-~45% lower than from [A9+vector] comparing to primary tumors over the duration of study. The untreated tumors [A9+vector control] were characterized not only by the intensive growth rate (FIG. 9), but also by severe clinical presentation. A rapid weight loss for a control metastatic group during the second part of the study was detected, while animals with primary tumors and tumors transfected with IL-33 were stably gaining weight (FIG. 9a). Moreover, ulcerations (stage 4-5) with bleeding of adjacent tissues were detected for some tumors in the group, but not for primary or IL-33 treated tumors. However, the most important and unfavorable prognostic factor for the clinical course of tumor development is the metastatic spread of the disease. It was hypothesized that metastasis-initiating cells were present within circulating tumor cells (CTCs). To assess the dissemination of circulating tumor cells over the mouse body, we used Flow Cytometry. We were looking for GFP+ tumor cells in disaggregated tissues of the most common metastatic sites for lung carcinoma, such as brain, lungs, liver, adrenal glands, lymph nodes and blood tissue comparing IL-33-stably transfected tumors to different controls—WT (no tumor), A9 (untreated tumor), A9+vector control, TC1+vector control. Flow cytometry analysis detected the highest percentage of GFP-positive cells in Liver (~32%) and Adrenal glands (~16%) of animals bearing [A9+vector control] tumors. Transfection of A9 cells with IL-33 reduced the average number of GFP+ cells in Liver to ~0.15% and to ~2.63% in Adrenal Glands (FIG. 10). Single green cells were detected in Lung and Blood, while all the Brain samples were GFP-free. The circulating tumor cells were not detected in all the tested tissues and organs of animals bearing tumors with local growing potential (TC1), which are not programmed to disseminate to distant sites. This idea was supported by histopathological examination of the resected tumors, which showed a clear morphological differentiation between primary and metastatic tumor forms. The nuclei of metastatic cells were more pleomorphic. Malignant cells had a smaller cytoplasmic content and a higher nucleus/cytoplasm ratio, forming dense, uniformly distributed, solid architecture (FIG. 11a). Primary tumors were distributed amongst adjacent tissues (depository tissues on FIG. 11b), forming a "squishy" structure, resembling a sponge, which clearly distinguished them from malignant tumor cell proliferation. Moreover, primary tumors were enclosed by a well-defined fibrous capsule (FIG. 11c), composed of fibroblasts and collagen deposition. The presence of the capsule allows primary tumors to remain localized at the site of origin and defines a fundamental criterion of morphological and biological differentiation between primary and malignant tumors. Malignant tumors, in contrast, do not usually possess a capsule and, therefore, are able to disseminate to distal organs. Thus, a murine lung tumor model (A9), which spontaneously acquired MHC-I-loss phenotype due to immune selection, was able to retain its metastatic properties in vivo upon transplantation and allowed us to correlate MHC-I-loss phenotype to malignant potential with invasive spread of the disease. Moreover, IL-33-induced changes were able to alter the clinical course of tumor development. Collectively, these observations suggest that IL-33-gene-complementation can modify the malignant gene expression programming. As a result, it affects the metastatic potential of the cancer cell population by reducing the tumor growth rate, metastatic spread of the disease and its severity.

Tumor-Infiltrating Immune Cells:

Tumor-infiltrating immune cells are intimately linked to the kinetics of tumor growth. To quantify the gene-complementation induced changes in tumor-infiltrating immune cell count, flow cytometry was applied and visualized by immunohistochemistry (IHC). The involvement into immune response of innate (ILC2s, Neutophils, Macrophages) and adaptive immune (CD4, CD8 T cells) systems was assessed, as well as immune suppressive cell content (T regulatory cells). The percentage of CD8+ cells detected by Flow Cytometry in disaggregated tumor tissues was increased in tumorurs that expressed IL-33 (FIG. 12). The level of CD4+ cells in genetically complemented tumors increased comparing to negative control. Visualization by IHC of tumor-infiltrating lymphocytes (TILs) on the sections from solid tissue showed increased staining intensity for MHC1, CD8+ and CD4+ positive cells within the tumors complemented with IL-33, when compared to negative control (FIG. 13). Positive changes in immune recognition by CTLs were well in line with immune suppressive cell content. Thus, malignant tumor microenvironment was characterised by up-regulation of resistance associated markers (FoxP3+), whereas IL-33-induced changes appeared to affect the expansion and accumulation of immune suppressive cells. The increased frequency and number of CD4+ and CD8+ cells in tumors in IL-33 introduced into metastatic tumors suggested that the subset of TILs may mediate protective anti-tumor immunity in murine lung carcinoma. The fact that T cells also require antigen stimulation to up-regulate expression of CD8 implies that IL-33-induced changes may over-come TAP-1/MHC-I deficiency of metastatic tumors in vivo and support the conclusions from our in vitro complementation experiments. The anti-tumor inflammatory response was analyzed after examining the infiltration of microphages, neutrophils and eosinophils throughout the tumor tissue. Tumor associated macrophages (TAM) were found to be uniformly distributed within all collected tumors with higher infiltration level in primary [TC1+vector] and IL-33 treated [A9+IL-33] ones compared to metastatic controls [A9+vector]. Upon tissue damage due to tumor growth in the area, local macrophages and other cells sense the insult and produce inflammatory mediators such as cytokines and chemokines that stimulate the infiltration of large numbers of polymorphonuclear leukocytes such as neutrophils, eosinophils into the tumor tissue. Acute inflammation of adipose tissue was characterized by neutrophilic infiltration in primary [TC1+vector] and genetically-complemented metastatic tumors. As such, inflammatory cells and mediators are elevated in the microenvironment of primary [TC1+vector] and [A9+IL-33] tumors, but not in metastatic tumors [A9+vector], which is in line with our microarray data showing significant down-regulation of inflammation-related genes, such as prostaglandin and leukotriene families, as well as interleukin (IL)-related genes. The lack of important attractants of inflammatory response in metastatic tissue was demonstrated using Giemsa staining for eosinophils. Two focal areas of eosinophils accumulations were found within the normal tissue adjacent to the periphery of the malignant tumor. The release of factors brought on by IL-33 expression significantly modified the microenvironment and allowed eosinophils flow through the tissue. There was a marked infiltration of eosinophils randomly distributed through the section of IL-33 modified tumor (FIG. 19). These observations suggest that the presence of IL-33 in the system can alter the inflammatory response within tumor microenvironment, which may mediate protective anti-tumor immunity in murine lung carcinoma on the innate and adaptive levels.

The Frequency of ILC2s is Elevated in Primary Tumors and Metastatic Tumors Expressing IL-33:

To directly examine the involvement of ILC2s and IL-33 in cancer progression, a flow cytometry approach with complex polychrome staining was used. Flow cytometry analysis of disaggregated tumor tissues revealed the presence of cells that did not expressed leukocyte lineage cell-surface markers (Lin: CD3, CD8, CD19, CD11c, Gr-1, NK1.1, Ter119). These cells showed a distinct pattern of cell-surface-marker expression of the 11-33 receptor T1/ST2 (ST2) chain, IL-7 receptor subunit IL-7Ra (CD127) and Thy1.2 (CD90.2). The population of Lin-ST2+CD127+CD90.2+ cells was morphologically similar to lymphocytes: round in shape with a high nuclear to cytoplasm ratio. To prove that phenotypically selected population of ILC2 were functionally capable to produce Th2 cell-type cytokines, cytokine production was measured using an ELISA assay. A subset of Lin-ST2+CD127+CD90.2+ cells was found that was able to grow and secrete IL-5 and IL-13 upon stimulation with a combination of thymic stromal lymphopoietin (TSLP) and IL-33. These data suggested that the population of Lin-ST2+CD127+CD90.2+ cells detected in tumors was phenotypically and functionally similar to innate lymphocyte group 2 cells.

ILC2s development and function is strongly dependent on the IL-33 presence in the microenvironment. The difference in IL-33 expression between primary and metastatic tumors allowed us to examine the involvement of ILC2s and IL-33 in cancer progression. We compared the level of ILC2s in primary (TC1) and metastatic (A9) tumors with or without IL-33 complementation. A significant decrease of the ILC2s count in disaggregated tissues of metastatic tumors versus primary or IL-33 complemented neoplasms was found (FIG. 14). These data suggested that ILC2s were involved in immune surveillance towards tumors. This was further supported by our in vivo study demonstrating that IL-33 expression suppressed tumor growth and metastatic spread of the disease.

Direct Demonstration that ILC2s Aid in Immune Recognition of Cancers In Vivo:

To examine the role of ILC2s and IL-33 in cancer progression, we compared the progression of metastatic A9 tumors with and without IL-33 complementation in RORα-deficient (lacking ILC2s) and wild-type (WT) mice. Bone marrow chimeras were constructed. For this, lethally irradiated B6.Pep3b (CD45.1) mice were reconstituted with whole bone marrow (BM) cells from either 4-week-old WT or RORα −/− (CD45.2) mice. Nine weeks later, the quality of transplantation was assessed by determining the ratio between CD45.1 and CD45.2 positive cells in peripheral blood and established tumors on CD45.2 re-populated chimeras. Tumors were allowed to grow for one month. Stable transfection of IL-33-gene into A9 cells significantly inhibited tumor growth rate in WT mice comparing to mice lacking ILC2s (FIG. 15). The percentage of ILC2s detected by Flow Cytometry in lymph nodes was increased in [A9+IL-33-gene] WT animals comparing to RORα−/− ones (FIG. 16). These observations demonstrated that IL-33 can modify tumor progression and support the conclusion that ILC2s participate in cancer immune surveillance through RORα-IL-33-ILC2 axis.

Example 2: Regulators of Immune Escape

The immune system limits the development of tumors unless the tumor cells undergo chromosomal alterations, which cause a phenotypic shift to an immunologically unrecognizable form, resulting in metastasis. There are several mechanism for immune evasion in tumors and one of them is down-regulation of the major histocompatibility class I gene (MHC-I), known in humans as the human leukocyte antigen (HLA). The loss of HLA class I molecules is associated with tumor aggressiveness and metastatic potential. Several types of cancer, including breast, renal, melanoma, colorectal, head and neck squamous cell, cervical and prostate cancer show a correlation between HLA down-regulation, poor prognosis and metastatic spread of the disease. However, the metastatic gene signature is a combination of genes, acting together to define the malignant potential of a tumor. Modifications of gene expression could render them immunologically recognizable and potentially halt immune evasion of tumors.

Aiming to find possible regulators of tumor transition to metastasis, a comparative microarray profiling of antecedent non-metastatic and metastatic cell lines of murine lung and prostate cancers, using Two Colour Agilent Microarray Technology was conducted. Total RNA samples of primary tumor cell lines and their metastatic derivatives were collected from both murine lung and prostate carcinomas and sent to the University Health Network (UHN) Microarray center. Fluorescence-labeled samples were hybridized on one array, using a two-way hierarchical clustering with a pearson centered distance metric following average linkage rules. From Agilent chip the data was imported to Genespring v11.0.1 for analysis and normalized using the recommended Agilent's spatial detrending Loess function. A "per probe" median centered normalization for visualization purposes was used to visualize the differences between the tissue types when clustering. All data analysis was performed on log 2 transformed data. There were a total of 55821 probes on the Agilent 28005 array. The data was then filtered to remove any probes that showed no signal in either channel. Probes in the upper 80th percentile of the intensity distribution were kept for future analysis reducing the number of probes to 48731. Next, the normalized and filtered dye intensity values were averaged across all eight samples. 37898 probes were available for further analysis. Gene expression between non-metastatic and metastatic cell lines was compared using a T-test against zero with multiple test corrected threshold of p<0.05. 5401 probes were found to be significant. Genes were marked as potential regulators of tumor progression to metastasis, if they showed a fold change in excess of two between non-metastatic and metastatic forms of both tumor types. This limited the number of probes to 1577.

To further narrow down the list of 1577 significantly different probes, genetic ontology (GO) analysis was performed using a Benjamini and Yuketiele hypergeometric corrected test statistic to determine the most significantly affected gene products. The gene ontology project is a collaboration of several gene databases, including the mouse genome database. GO describes gene products in terms of association to common biological processes, cellular components and molecular functions. Using GO analysis, ten groups of genes most differentially regulated between the metastatic (i.e. loss of MHC-I) and non-metastatic (i.e. MHC-I expressing) cell lines were identified. In particular, ten groups of gene products include examples of extracellular matrix remodelling genes and genes involved in immune response, giving us increased confidence in the microarray results and supporting the idea that genes that were indicative for metastasis and immune evasion were expected to come from these ontologies (see Table 2).

TABLE 2

Most significantly affected gene products between metastatic and non-metastatic cell lines.

| Go ID | GO Accession | GO Term | Corrected p-value | Count in selection | % Count in selection |
|---|---|---|---|---|---|
| 3317 | GO:0005578 | proteinaceous extracellular matrix | 2.56747E−5 | 17 | 35.41 |
| 12440 | GO:0031012 | extracellular matrix | 3.03565E−5 | 17 | 35.41 |
| 782 | GO:0001730 | 2′-5′-oligoadentlate synthetase activity | 2.00696E−4 | 4 | 8.33 |
| 16345 | GO:0044421 | extracellular region part | 0.00175302 | 18 | 37.50 |
| 16344 | GO:0044420 | extracellular matrix part | 0.02591157 | 3 | 6.25 |
| 4476 | GO:0006955 | immune response | 0.03232145 | 12 | 25.00 |
| 10826 | GO:0019882 | antigen processing and presentation | 0.03546091 | 6 | 12.50 |
| 3315 | GO:0005576 | Extracellular region | 0.07770341 | 32 | 66.66 |
| 591 | GO:0001503 | ossification | 0.09065761 | 4 | 8.33 |
| 3113 | GO:0005201 | extracellular matrix structural constituent | 0.09065761 | 4 | 8.33 |

To select the regulators for the transition of primary tumor to its metastatic form, the 10 most affected GO IDs were assessed using interactomes and resent literature sources. From this assessment a number of up-regulated genes responsible for matrix remodelling (e.g. MMP2, MM9, MMP10, MMP13) and down-regulated immune- and inflammation-related genes were identified. There were many well-known interferon (IFN)-induced genes (e.g. IRF1, IRF5, IRF7, IRF9, IFI27, IFI44, PSMB8, PSMB9, IFIT2, IFIT1, Igtp), prostaglandin and leukotriene families (e.g. Ptgfr, Ptgir, Ptgr1, Ptgis, Ltb4r1), interleukin (IL)-related genes (e.g. IL-11ra1, IL-13ra, IL15, IL-33), tumor necrosis factor and caspase families (e.g. TNFsf9, Casp7, Casp12), as well as genes coding for antigen processing and presentation (e.g. H2-K1, H2-DMb1, H2-Q5, H2-Q6, TAP1, TAP2, Tapasin, LMP2). The data showed that the inflammatory phenotype of primary tumors was down-modulated along with MHC-I-related genes and genes involved into IFN-signaling in the transition to a metastatic form. A similar pattern of somatic aberrations during the development of two different types of neoplasms suggested that the genes possibly were co-regulated.

IL-33 and IFI44 were selected for further study.

The level of expression for selected genes was confirmed by real time quantitative reverse transcriptase polymerase chain reaction (qRT-PCR). Aberrant expression of genes in the metastatic/non-metastatic cell lines provides an avenue to characterize and understand the mechanism of transition from immune recognition to immune evasiveness in tumors.

Interleukin 33 (IL-33) is a cytokine belonging to the IL-1 superfamily, which is known to affect the host response after inflammatory/immunological challenge. IL-33 is a dual-function protein that acts not only as a pro-inflammatory cytokine, but also as a nuclear factor. Nuclear localization and association with heterochromatin is mediated by the N-terminal domain and allows IL-33 to function as a novel transcriptional regulator of the p65 subunit of the NF-κB complex. The C-terminal domain is sufficient for binding to the ST2 receptor and activating the production of type 2 cytokines from polarized Th2 cells 22 and ILC2 cells.

Interferon-induced protein 44 (IFI44) is 48 kDa cytoplasmic protein mainly expressed by immune tissue: monocytes, dentritic cells, NK cells, T cells (CD4+), T cells (CD8+), B lymphoblasts. Overexpression of IFI44 cDNA induces an anti-proliferative state in vitro, even in cells that are not responsive to IFN-α. IFI44 contains a perfect GTP binding site. The observation allows to propose a functional model, in which IFI44 binds intracellular GTP, and this depletion abolishes extracellular signal-regulated kinase (ERK) signaling and results finally in cell cycle arrest and anti-proliferative activity of IFI44.

To validate the potential of selected genes, human tissue data from European Biostatistics Institute (EBI) was taken into account before final gene selection. It was confirmed that IL-33 and IFI44 are reduced in metastatic forms of human prostate carcinomas when compared to benign or primary tumors. Both genes were in concordance between gene expression level and/or protein level, indicating they may be good predictors for metastases.

Co-Regulation of Selected Gene-Candidates:

A similar pattern of gene expression profile during the development of two different neoplasms suggested that the genes possibly were co-regulated. Coordinately controlled genes in eukaryotic cells are expected to be activated by the same chemical signals and share a set of control elements. The promoter-enhancer regions of the IL-33, IFI44, H-2K1 and IFNγ genes in primary TC1 cells and metastatic A9 cells were sequenced and analyzed using Genomatix software, the Eukaryotic Promoter Database (epd.vital-it.ch) and the Computational Biology Research Center Database (www.cbrc.jp). Aligning the promoter-enhancer regions of the IL33, IFI44, H-2K1 and IFNg genes, we identified possible binding sites for common transcription factors, including CREB, AP-1, NF-kB, HSF, AML-1a, RORα, GATA (see Table 1 above).

Reciprocal Action of Selected Gene-Candidates:

To examine the reciprocal action of these genes, we used overexpression and siRNA targeted down-regulation of IL-33 and IFI44 in metastatic and primary tumor cell lines respectively. We found that overexpression of IFI44 in A9 cell line results in up-regulation of IL33 production on RNA and protein levels compared to un-treated cells or cells transfected with empty vector, where as the down-regulation of IFI44 in TC1 cell line leads to suppression of both IFI44 and IL-33 gene expression level compared to untreated TC1 cells or TC1 cells treated with irrelevant siRNA. Reciprocally, both IL-33 gene and protein were able to elevate IFI44 in immune evasive study model. Interestingly, that spleenocytes from animals with H-2K1 deficient backgrounds showed decreased IL-33 expression. This suggests that IL-33 and IFI44 are likely to be co-regulated or to be involved into the same signaling pathway in the development of carcinomas.

The selected gene-candidates were tested to determine if they complement immune recognition of MHC class I-loss tumors. In particular:
- IL-33, IFI44 genes contribute to increased TAP-1 and H2-Kb expression/signaling in the MHC-loss A9 murine lung carcinoma cells (FIG. 26).
- IL-33, IFI44 genes contribute to increased TAP-1 and H2-Kb expression/signaling in the MHC-loss A9 murine lung carcinoma cells (FIG. 27).
- IL-33-cytokine contributes to increased H2-Kb expression/signaling in the MHC-loss A9 murine lung carcinoma cells (FIG. 28).
- IL-33, MR-1 contributed to increased H2-Kb expression/signaling in the MHC-loss A9 murine lung carcinoma cells (FIG. 29).
- MHC-1 and selected gene-candidates were demonstrated to be co-regulated during the metastatic re-programming of primary tumor revealing their (genes') metastatic potential. Specifically, FIGS. 30 to 32 illustrate that down regulation of IL-33, MR-1 or IFI44 decreased H2-Kb expression and FIGS. 33 and 34 illustrate that down regulation of H2-Kb decreased selected gene-candidates expression.

To test whether candidate gene-induced increase in TAP-1 and MHC-I expression in TAP-1/MHC-I-deficient cell line A9 could contribute to the anti-tumoral effect of these gene in vivo, a gene-complementation mouse study was conducted. A pIRES2-EGFP-expressing vector system (both plus and minus the IFI44 gene) was stably transfected into A9 and TC1 cells. The EGFP was constitutively expressed and allowed green tumor cells to be tracked for spread beyond the initial site of injection. Expression of IFI44 or IL-33 significantly inhibited A9 tumor formation (FIGS. 38 to 40). The mice injected with A9 alone also suffered from severe clinical presentation in the form of significant weight loss while mice injected A9+IFI44 of IL-33 did not (FIG. 41). In addition, IL-33 and IFI44 gene-complementation reverses metastatic spread of the disease in vivo (FIGS. 42 and 43, Table 3 below).

TABLE 3

IL-33 and IFI44 gene-complementation inhibits metastatic spread of circulating tumor cells to distal organs.

|  | WT control | A9 control | A9 + vect control (gated range) | A94 + IL33 (gated range) | A94 + p44 (gated range) | TC1 + vector control |
|---|---|---|---|---|---|---|
| Liver | 0.00% | 0.00% | 24.0%-37.2% | 0.0%-0.2% | 0.00% | 0.00% |
| Adrenal glands | 0.00% | 0.00% | 3.7%-14.9% | 0.9%-4.3% | 0.00% | 0.00% |
| Lungs | 0.00% | 0.00% | 0.00%-1.3% | 0.00%-0.2% | 0.00%-0.1% | 0.00% |
| Blood | 0.00% | 0.00% | Single cells 1-33 cells/ 0.5 mil = 0.00% | 0.00%-0.2% | 0.00% | 0.00% |
| Brain | 0.00% | 0.00% | 0.00% | 0.00% | 0.00% | 0.00% |

Tumor-infiltrating immune cells are intimately linked to the kinetics of tumor growth. The involvement of innate immunity (e.g. ILC2s, neutrophils, macrophages, eosinophils) and adaptive immunity (CD4+ and CD8+ T cells) was assessed by flow cytometry and immunohistochemistry. See FIGS. 44 to 50 for immune cell counts primary (TC1) tumors, metastic (A9 tumors) genetically modified to with vectors expressing IFI44 or IL-33 or control vector.

Conclusions:
- IL33 and IFI44 affects the metastatic potential of the cancer cell population reducing the tumor growth rate, metastatic spread of the disease and its severity.
- The increased content of CD4+ and CD8+ cells in tumors suggested that this subset of TILs may mediate protective antitumor immunity.
- A significant decrease of the ILC2s count in disaggregated tissues of metastatic tumors versus primary or complemented neoplasms suggests that ILC2s are involved in immune surveillance towards tumors.
- The Th2 immune response may participate in cancer immune surveillance through IL-33-ILC2s axis.

Example 3: Type 2 Innate Lymphoid Cell Mediated Immune Defenses are Subverted in Metastatic Cancer Resulting in Summary Immune-Escape Summary:

Transition from primary to metastatic carcinoma is marked by reduction of IL-33 expression and loss of antigen-processing machinery (APM) function. Induction of IL-33 expression in metastatic tumors stimulated APM function, reduced tumor growth and numbers of circulating tumor cells while increasing the frequency of Type-2 Innate Lymphoid Cells (ILC2). Furthermore, tumors had increased growth rates in mice lacking ILC2s. Clinical studies additionally demonstrated that prostate and kidney carcinoma patients with low tumor expression of IL-33 have a shorter median time of survival. Overall, the absence of IL-33 expression resulted in both the reduction of APM functionality, rendering tumors invisible to effector T-lymphocytes, and the failure to induce ILC2s, providing a new paradigm for understanding immune-escape and cancer metastasis.

Results

IL-33 Expression is Decreased in Malignant Carcinomas:

To address the metastatic gene signature network, a comparative microarray analysis was conducted on antecedent non-metastatic and metastatic cell lines of murine lung and prostate cancers, using Two Colour Agilent Microarray Technology. Aberrant expression of genes in the metastatic/non-metastatic cell lines provides an avenue to characterize and understand the mechanism of transition from immune recognition to immune evasiveness in tumors. To validate the translational potential of a selected gene, primary human tissue data was taken into account. It was confirmed that gene-candidates are reduced in metastatic forms of human prostate carcinomas. Specifically, using the data obtained from the Gene Expression Atlas created by the European Biostatistics Institute (access date: Jan. 30, 2013), it was determined that genes of interest are downregulated in metastatic prostate cancer compared to benign and primary prostate tumors. The gene expression level in the data was in concordance with its protein expression level, indicating that it may be a good predictor for metastasis.

Genes known to be involved in novel aspects of inflammation or immunity, those that may interact with the antigen presentation machinery, and those that may be involved into Interferon (IFN)-signaling pathways were selected for further study. One gene in particular, IL-33, was found to be downregulated in metastatic tumors and was selected for further study since it is a key inducer of helper T cells and innate immune cells. According to our microarray data, IL-33 is down-regulated 3-6 fold in the metastatic murine carcinomas (FIG. 59). This was confirmed by separate qRT-PCR on cells grown in vitro.

The involvement of the immune response in limiting prostate cancer and potential effectiveness of immunotherapeutic approaches in decreasing cancer recurrence is still widely debated. The expression of IL-33 in prostate cancer specimens obtained at the Vancouver Prostate Centre (VPC) was examined. At the mRNA level, IL-33 expression was higher in benign prostate tissue than primary tumors ($p<0.0001$; t-test), and further reduced in castration-resistant prostate cancer (CRPC) in a large cohort of RNA-sequencing data (FIG. 52a), suggesting a correlation with disease progression. Next, the protein expression of IL-33 was evaluated by immunohistochemistry in 342 prostate cancer specimens obtained at prostatectomy (FIG. 52b). Remarkably, low IL-33 expression was significantly associated with reduced time to prostate-specific antigen (PSA) recurrence (a marker of relapse) after prostatectomy ($p<0.0001$; Logrank test) (FIG. 52b). Patients with low tumor IL-33 expression had a median time to recurrence of 56.7 months, compared to 97 months for patients with higher tumor IL-33 expression. This effect appeared to be dependent of Gleason grade, since there was a significant difference in IL-33 expression between tumors of Gleason pattern 3 and 5. To confirm this clinical association, IL-33 expression was further explored in an independent publically-available cohort of mRNA expression data from 131 prostate cancer specimens obtained at prostatectomy, and 19 metastatic tumors (PMID: 20579941). Again, IL-33 showed reduced expression with disease progression, and IL-33 down-regulation was significantly associated with reduced time to PSA recurrence ($p=0.013$; Logrank test) (FIG. 52c). Overall this data suggests that reduced IL-33 expression in prostate cancer cells is associated with progression to metastatic disease. A similar trend was observed in patients with Kidney renal cell carcinoma (The Cancer Genome Atlas' data set was obtained from 513 cases (cancergenome.nih.gov). IL-33 down-regulation was significantly associated with reduced survival time (FIG. 52d) and patients with low IL-33 expression had a shorter median time of survival (52.04 months), compared to patients with higher tumor IL-33 expression (80.62 months).

IL-33 Complements MHC-I, Antigen Processing and Immune Recognition of Metastatic Tumors:

Down-regulation of TAP-1/MHC-I has been shown to be a primary indicator for rapid tumor progression and metastasis in human (Blades et al., 1995; Naoe et al., 2002; Zhang et al., 2003) and, therefore, we wanted to investigate the effects of the IL-33 on TAP-1/MHC-I expression. We overexpressed IL-33 (FIG. 60) in the TAP-1-deficient murine lung carcinoma cell line (A9), which has very reduced MHC-I expression. Overexpression of IL-33 in these cells induced increased expression of both TAP-1 and H2-K1 (FIG. 53a, 53b). The addition of recombinant IL-33 protein also up-regulates TAP-1 and H2-K1 expression yet does not affect DNA-dependent innate immune signaling pathways (FIG. 53b). Furthermore, increased surface H2-K1 expression was observed suggesting that IL-33 acts upstream of the antigen presentation pathway to restore MHC-I expression in these cells (FIG. 53c).

To further evaluate the functionality of changes induced by IL-33, the ability of IL-33-transfected and IL-33-cytokine treated A9 cells to present the H2-K1-restricted ovalbumin epitope (OVA (257-264); SIINFEKL; SEQ ID NO. 9) was assessed. After incubation of cells with soluble OVA (257-264; SEQ ID NO. 9), the treated A9 cells were cultured with B3Z cells (Karttunen et al., 1992), which are a T cell hybridoma that is activated by the recognition of H-2Kb in association with OVA (257-264; SEQ ID NO. 9). A9 cells treated with exogenous IL-33 cytokine were able to present a higher number of H2-K1-OVA (257-264; SEQ ID NO. 9) complexes on their surface than did A9 cells transfected with IL-33 gene alone. This resulted in a greater capacity for B3Z T cell priming and activation (FIG. 53d). This may stress the role of IL-33 as a secreted cytokine and the importance of the signaling cascade triggered by IL-33 binding to its corresponding cell surface receptor, over its role as a nuclear protein. These data directly demonstrate that IL-33 improves immune recognition of MHC-I-loss lung carcinoma A9.

Furthermore, ILC2s are able to induce TAP-1 promoter transcription in co-incubated metastatic prostate tumor cells supporting the idea that ILC2s may directly induce antigen processing and presentation pathway in tumors. In a separate mechanism, the effect of ILC2s on cell-mediated cytotoxicity of CD8+ T cells was studied in a murine prostate model (LMD). It was found that ILC2 cells could up-regulate Granzyme B, a specific effector function of cytotoxic T lymphocytes. This suggests that ILC2s are able to promote CTL effector functions. (FIG. 61).

Modulation of Malignant Gene Expression Programming:

To address the role of IL-33 in tumor immune evasiveness, IL-33 was inhibited using siRNA in primary tumor cells (TC1). After siRNA treatment for 72 to 96 h, MHC-I surface expression level was assessed. The down-regulation of IL-33 was confirmed by ELISA and immunoblot analysis (FIG. 62a). TC1 cells treated with IL-33-directed siRNAs had a much lower abundance of H2-K1 complexes than did controls (FIG. 62b). To investigate the effect of MHC-I down-regulation on IL-33 expression, siRNAs directed against MHC-I (FIG. 56) were used on the primary tumor cells. IL-33 appeared to be important for the expression of immune recognizable phenotype in the TC1 cell line. Moreover, the data suggested that MHC-I and IL-33 may be co-regulated during the metastatic re-programming of primary tumor revealing the involvement of the IL-33 gene in metastasis.

IL-33 Gene-Complementation Reverses Metastasis In Vivo:

The finding that IL-33 deficiency results in fewer surface H2-K1 complexes suggests that these molecules may be co-regulated during metastatic transformation of the primary tumor to its malignant form, linking IL-33 expression to antigen presentation. To test whether IL-33-induced increase in TAP-1 and MHC-I expression in TAP-1/MHC-I-deficient cell line A9 could contribute to the anti-tumoral effect of IL-33-gene in vivo, a gene-complementation mouse study was conducted. A pIRES2-EGFP-expressing vector system (both plus and minus the IL-33 gene) was stably transfected into A9 and TC1 cells. The EGFP was constitutively expressed and allowed green tumor cells to be tracked for spread beyond the initial site of injection.

Expression of IL-33 Significantly Inhibited A9 Tumor Formation.

The mean volume of tumors grown from A9+IL-33 cells was ~30-45% lower than from A9 control, although both were higher as compared to primary TC1 tumors over the duration of study (FIG. 54a). The mice injected with A9 alone also suffered from severe clinical presentation in the form of significant weight loss and tumor ulceration. Thus, rapid weight loss occurred in the control metastatic group during the second part of the study. Animals with primary tumors (TC1) and A9+IL-33 tumors maintained or gained weight throughout the study. Tumor ulcerations (stage 4-5) with bleeding of adjacent tissues were detected for some cases in the group injected with A9 alone, but not for those injected with TC1 or A9+IL-33 cells.

The most important and unfavourable prognostic factor for the clinical course of tumor development is the metastatic spread of the disease. Therefore the appearance of circulating tumor cells (CTCs) in disaggregated tissues of the most common metastatic sites for lung carcinoma was assessed: brain, lungs, liver, adrenal glands, lymph nodes and blood tissue. The highest percentage of GFP-positive tumor cells was detected in liver (~32.0%) and adrenal glands (~16.0%) of animals bearing A9 tumors. IL-33 expression by the A9 tumor cells reduced the average number of GFP-positive cells in liver to ~0.15%, and to ~2.63% in the adrenal glands (FIG. 54b, 54c, 54d). Only single tumor cells were detected from lung and blood, while all the brain samples appeared tumor-free. CTCs were not detected from any of the tested tissues and organs of animals bearing subcutaneous tumors with local growing potential (TC1), which are not programmed to disseminate to distant sites (Table, below).

TABLE 4

IL-33 gene complementation inhibits metastatic spread of tumor cells to distal organs. GFP-positive circulating tumor cells were isolated from sites that were distal from initial subcutaneous inoculation and assessed using Flow Cytometry. Shown here are representative results from eight animals in each group.

| Distal Organ | Control (no tumor cells) | Tumor Cell | | |
|---|---|---|---|---|
| | | A9 | A9 + IL-33 | TC1 |
| Liver | 0.00% | 24.0%-32.3% | 0.00%-0.2% | 0.00% |
| Adrenal glands | 0.00% | 3.7%-14.9% | 0.9%-4.3% | 0.00% |
| Lung | 0.00% | 0.00%-1.3% | 0.00%-0.2% | 0.00% |
| Blood | 0.00% | Single cells 1-33 cells/0.5 ml = 0.00% | 0.00%-0.2% | 0.00% |
| Brain | 0.00% | 0.00% | 0.00% | 0.00% |

Collectively, these observations suggest that IL-33 gene-complementation can modify the malignant gene expression programming. As a result, IL-33 likely affects the metastatic potential of the cancer cell population reducing the tumor growth rate, metastatic spread of the disease and its severity.

Tumor-Infiltrating Immune Cells:

Tumor-infiltrating immune cells are intimately linked to the kinetics of tumor growth (deLeeuw et al., 2015; Fridman et al., 2012). The involvement of innate immunity (e.g. ILC2s, neutrophils, macrophages, eosinophils) and adaptive immunity (e.g. CD4+ and CD8+ T cells and FoxP3+T regulatory cells) was assessed by flow cytometry and immunohistochemistry. Using flow cytometry the percentage of CD4+ and CD8+ T cells in disaggregated A9 tumor tissues was lower than the percentage of CD4+ and CD8+ T cells isolated from either primary TC1 or A9+IL-33 tumors (FIG. 64). Visualization by immunohistochemistry of tumor-infiltrating lymphocytes (TILs) on tumor sections showed increased staining intensity for MHC-I+, CD8+ and CD4+ positive cells within IL-33-expressing tumors when compared to A9 alone. Up-regulated immune recognition shown previously by cytotoxic T lymphocytes (CTLs) in the B3Z assay (FIG. 53) was well in line with the number of CD4+ and CD8+ TILs seen within tumors (FIG. 55). The increased frequency and number of CD4+ and CD8+ T cells in IL-33 expressing tumors suggests that these TILs may mediate protective anti-tumor immunity in murine lung carcinoma. The fact that T cells also require antigen stimulation to up-regulate expression of CD8 implies that IL-33 induced changes may over-come TAP-1/MHC-I deficiency of metastatic tumors in vivo and support the conclusions from the in vitro complementation experiments. Interestingly, the malignant tumor microenvironment was characterized by TILs exhibiting suppressive T-regulatory cell markers (FoxP3+), which are also associated with tumor immune-resistance. The expression of IL-33 by the tumor appeared to prevent the accumulation of these immune suppressive cells. Furthermore, tumor-associated macrophages (TAM) and neutrophils were found to have higher infiltration level in IL-33 expressing TC1 and A9+IL-33 tumors compared to metastatic A9 tumors (FIG. 55, upper panel). Eosinophils could be seen at the tumor periphery in metastatic A9 tumors, adjacent to the normal tissue, whereas, the expression of IL-33 appeared to modify the microenvironment and allow eosinophils to flow into the tumor tissue and exert an anti-tumor effect, perhaps, due to IL-5 production by ILC2s (FIG. 55, bottom panel). These observations suggest that the presence of IL-33 in the system mediates protective anti-tumor immunity in carcinomas.

The Frequency of ILC2s is Elevated in Primary Tumors and Metastatic Tumors Expressing IL-33:

The presence of ILC2s was detected in the disaggregated tumor tissue using flow cytometry. ILC2s were identified as cells that did not express leukocyte lineage cell-surface markers (Lin:CD3, CD8, CD19, CD11c, Gr-1, NK1.1, Ter119), while exhibiting a distinct pattern of cell-surface marker expression of the IL-33 receptor T1/ST2 (ST2) chain, IL-7 receptor subunit IL-7Ra (CD127) and Thy1.2 (CD90.2). The population of Lin-ST2+CD127+CD90.2+ cells was further shown to be morphologically similar to lymphocytes: round in shape with a high nuclear to cytoplasm ratio. Upon isolation in vitro, this cell subset was able to grow and secrete IL-5 and IL-13 after stimulation with a combination of thymic stromal lymphopoietin (TSLP) and IL-33. These data suggested that the population of Lin-ST2+ CD127+CD90.2+ cells detected in tumors was phenotypically and functionally ILC2s.

ILC2s development and function is strongly dependent on the IL-33 presence in the microenvironment. The difference in IL-33 expression between primary and metastatic tumors enabled examination of the involvement of ILC2s and IL-33 in cancer progression. The level of ILC2s in primary (TC1) and metastatic (A9) tumors with or without IL-33 complementation was assessed. A significant decrease of the ILC2s count in disaggregated tissues of metastatic tumors versus primary or IL-33 complemented neoplasms (FIG. 56) was observed. These data suggested that ILC2s are involved in immune-surveillance towards tumors. This was further supported by the data above demonstrating that IL-33 expression suppressed tumor growth and metastatic spread of the disease (FIG. 54, Table above).

Interestingly, it was also observed that IL-33-gene complementation decreased proliferation of tumor cells (FIG. 65), which is supported by a recent report highlighting a dual function of IL-33 on the proliferation of NIH 3T3 cells in vitro in the absence of an immune response (Tominaga et al.). It was further found IL-33 did not affect tumor cell apoptosis, in accordance with Tominaga et al. The data suggest IL-33 affects tumor growth in two separate ways: directly inhibiting tumor cell proliferation, and separately, activating the immune response.

Demonstration that ILC2s Aid in Immune Recognition of Cancers In Vivo:

To directly examine the role of ILC2s and IL-33 in cancer progression, a comparison of the progression of metastatic A9 tumors with and without IL-33 complementation in RORα-deficient (lacking ILC2s) and wild type mice was conducted. RORα −/− mice have normal number of NK cells and ILC3s, and do not develop from RORα-positive progenitors (CHILPs) (Martinez-Gonzalez et al., 2015). Unlike ILC2s, Th17 cells express RORα and RORγ, and RORα-deficiency can be compensated by RORγ suggesting a minimal effect on Th17 cells in the RORα −/− mice (Martinez-Gonzalez et al., 2015). Bone marrow chimeras were generated by reconstitution of lethally irradiated B6.Pep3b (CD45.1) mice with whole bone marrow (BM) cells from either 4-week-old wild type or RORα −/− (both CD45.2) mice. Bone marrow transplant recipients were allowed to recover for 6 weeks, after which it was determined that the transplants were more than 92% efficient. A9 or A9+IL-33 cells were then injected subcutaneously and allowed to grow. It was observed that expression of IL-33 by A9 cells significantly inhibited tumor growth rate in wild type mice compared to mice lacking ILC2s (FIG. 57*a*). The percentage of ILC2s in lymph nodes was increased in A9+IL-33 wild-type animals compared to RORα−/− chimeras (FIG. 57*b*), while adaptive immune response was not affected (FIG. 57*c*). These observations demonstrated that IL-33 could modify tumor progression and supported the conclusion that ILC2s participate in cancer immune-surveillance through RORα-IL-33-ILC2 axis.

Discussion:

In this example, microarray analysis was performed to begin to define the metastatic gene signature of prostate and lung carcinomas. Specifically the multifunctional alarmin IL-33 was identified as being down-regulated in human and murine carcinomas during the transition from primary to metastatic tumors. IL-33 is known to be associated with inflammatory process, and it was further demonstrated that IL-33 expression promotes immune recognition of tumors through both the generation of ILC2s that facilitate innate and adaptive immune responses and by transcriptional induction of APM in normal epithelial cells or primary tumors through paracrine and autocrine induction. Reciprocally, here is described for the first time an immune-escape mechanism that occurs during the metastatic transition of tumors, whereby down-regulation of IL-33 consequently results in two critical events that facilitate immune-evasion: the reduction of APM activity in tumors and the failure to foster ILC2 function.

The difference in IL-33 levels within the tumor microenvironment of the primary and metastatic carcinomas led to the study of ILC2s, whose development and functioning are strongly dependent on the IL-33 expression in the system. A significant decrease in the number of ILC2s was observed in disaggregated tissues of metastatic tumors versus primary or IL-33 complemented neoplasms. These data suggest that ILC2s are involved in immune-surveillance towards tumors, thus linking cancer progression to the absence of ILC2s. The generation of bone marrow chimeric mice made it possible to study the mechanistic details of the involvement of ILC2s in the modification of tumor progression. RORα-deficient mice have significantly smaller number of ILC2s. Notably in this model, RORα deficiency does not affect the level of CD4 and CD8 cells in lymph nodes, suggesting that the pathways for the generation of innate and adaptive lymphocytes are indeed distinct. It was observed that stable transfection of IL-33-gene into A9 cells significantly inhibited tumor growth rate in wild type mice comparing to mice lacking ILC2s, demonstrating, for the first time that ILC2s participate in cancer immune-surveillance through RORα-ILC2 pathway. RORα-IL-33-activated ILC2s may play an important role in tumor elimination by recruiting other cells, such as eosinophils via IL-5 production. In the light of these observations and the recent publication (Carretero et al., 2015) on the role of eosinophils into tumor rejection through CD8+ T cells chemo-attraction, the missing link of the crucial importance of ILC2 cells in cancer immune-surveillance becomes clear. A cellular mechanism model is proposed (FIG. 58) that is consistent with our present knowledge of ILC2s (Carretero et al., 2015; Drake et al., 2014; Martinez-Gonzalez et al., 2015; McKenzie et al., 2014). The other major finding of this study that is worthy of note is that IL-33 is a strong inducer of MHC-I and antigen processing in metastatic cancers. The current paradigm that emergence of tumors is limited by a robust adaptive immune response generated by the interaction of a CD8+ T cell with a TAA-MHC-I complex. This mechanism of immune-surveillance is thought to work efficiently until tumor cells undergo chromosomal alterations that result in a loss of the expression of components of the APM and subsequent conversion to an immune-escape phenotype. IL-33 was identified as being important for the immune recognition of prostate and lung carcinomas. Collectively, the data imply that IL-33 works in a paracrine and/or an autocrine manner to induce APM genes and that IL-33 is secreted from normal epithelium and primary tumors but is down-regulated in metastatic tumors thereby allowing the tumors to escape or subvert CTL recognition by concomitantly reducing APM function. Down-regulation of MHC1-related genes ultimately leads to a reduction of immune-surveillance in metastatic cancers. Consequently, the immunologically altered phenotype has an adaptive growth advantage over the original form, whose growth remains hampered by the immune system. Moreover, the study indicates that complementation of tumor cells with IL-33 can reverse antigen presentation deficiency, subsequently shifting the tumor phenotype from immune-evasive to that of being recognized by the immune system. Not only does IL-33 induce MHC-I and endogenous antigen processing in metastatic carcinomas, MHC-I and IL-33 also appear to be co-regulated during the metastatic re-programming of primary murine lung tumor, revealing the metastatic potential of IL-33 gene. Many studies support the relevance of these observations to cases of human cancer where APM components are down-regulated (Alimonti et al., 2000b; Alpan et al., 1996; Delp et al., 2000; Gabathuler et al., 1994; Harris et al., 1994; Johnsen et al., 1999; Kaklamanis et al., 1995; Lankat-Buttgereit and Tampe, 2002; Liu et al., 1997; Ritz and Seliger, 2001; Seliger et al., 1997, 2000a; Seliger et al., 2000b; Vitale et al., 1998) (Alimonti et al., 2000b; Gabathuler et al., 1994; Giorda et al., 2003; Korkolopoulou et al., 1996; Lou et al., 2008; Lou et al., 2005; Singal et al., 1996). Furthermore, studies on human melanoma show a clear correlation between MHC-I down-regulation and poor prognosis (Tao et al., 2008). In addition, studies of several other types of cancer, including renal carcinoma (Kitamura et al., 2007), colorectal carcinoma (Watson et al., 2006), head and neck squamous cell cancer (Andratschke et al., 2003), cervical cancer (Mehta et al., 2008), and breast cancer (Zia et al., 2001) have found a similar statistically significant relationship. Another study showed that cigarette smoke reduces the expression of antigen presentation components in lung tissues (Fine et al., 2002). This intriguing observation may indicate a direct link between smoking and increasing the evasiveness of lung cancers.

The human study results suggest that the expression level of IL-33 reflects the transition of primary prostate tumor to its metastatic form. It was demonstrated on the basis of mRNA and protein expression levels that low IL-33 content in radical prostatectomy specimens is associated with a significantly decreased time to relapse after surgery compared to specimens with high IL-33 expression and had a shorter median time of survival (52.04 months), compared to patients with higher tumor IL-33 expression (80.62 months). The data shows that down-regulation or in some cases, mutation of IL-33 in human prostate and kidney carcinomas is predictive of early recurrence of cancer. Thus, IL-33 becomes the first identified positive immune biomarker in prostate cancer, where previous study has failed to provide one.

Metastatic cancer is considered the final stage of the disease and only a small fraction of patients will survive this form of the disease. A profound limitation in the application of general cancer treatments is the genetic and phenotypic heterogeneity in tumors between patients. Furthermore, current immunotherapy is hampered by the need to personalize treatments based on individual-specific tumor antigens (Rigamonti and Bellone, 2012; Slovin, 2015), as well as the individual-specific T cell receptor expression in responding TILs. These parameters and others, such as responsiveness to PD-1, PD-1L or CTLA4 treatment, impact therapeutic options. Here it is demonstrated that IL-33 induces MHC-I and antigen processing in metastatic tumors and we identified IL-33-induced ILC2s as a new arm of immune-surveillance involved in recognizing metastatic cancer cells.

Material and Methods: Cell Lines:

Murine Prostate Cancer Model:

The PA and LMD cell lines were used as models of non-metastatic and metastatic prostate cancer, respectively. PA is a primary murine prostate cancer cell line derived from a 129/Sv mouse using a mouse prostate reconstitution model system that displays high expression of MHC-I. LMD is a metastatic TAP- and MHC-I deficient derivative of PA which emerged as a metastatic daughter after escaping and metastasising from the kidney capsule during serial transfer of the PA cells (Lee et al., 2000).

Murine Lung Tumor Model:

The TC1 cell line is a murine lung tumor model derived from primary lung epithelial cells of C57BL/6 mice immortalized using the amphotropic retrovirus vector LXSN16 carrying human papillomavirus genes E6/E7, and subsequently transformed with pVEJB plasmid expressing the activated human c-Ha-ras oncogene. TC1 cells display high expression of TAP-1 and MHC-I. The cell line A9 was derived from the TC1 tumor cell line and display spontaneous down-regulation of MHC-I (or H2-K1) by immunoselection in vivo during immunization/challenge experiment (Smahel et al.). All the above cell lines were grown in Dulbecco's modified Eagle medium, supplemented with 10% heat-inactivated fetal bovine serum, 2 mM l-glutamine, 100 U/ml penicillin, 100 µg/ml streptomycin, and 10 mM HEPES.

Microarray Analysis of Both Cell Systems:

Purified mRNA samples from both cancer cell model systems were sent to the Microarray Centre at the University Health Centre (now called The Princess Margaret Genomics Centre) in Toronto, Canada, where they were hybridized to a 28005 Two-Color Agilent microarray with a total of 55821 probes. Data analysis was performed using GeneSpring GX software (Agilent Technologies).

Gene Expression Constructs and Transfection:

Note: untransfected cells were used for microarray studies and for siRNA studies.

Transient Clones:

A gene expression construct with full-length cDNA for the selected mouse IL-33 gene (NM_001164724.1) was produced using the pIRES2-EGFP vector (Clontech Lab). Vector constructs, i.e. either vector alone or vector+IL-33 gene, were transfected into both the primary TC-1 cell line and the antecedent immune evasive, MHC-I deficient cell line, A9, using a FuGene 6 transfection reagent (Promega).

Stable Clones:

TC-1 and A9 cells were transfected with the pIRES2-EGFP-gene constructs using FuGene 6 transfection reagent (Promega) in vitro. Forty eight hours after transfection GFP-positive cells were sorted by FACS (BD Aria II cell sorter) in order to obtain stable transfectants. Selection and expansion in culture was repeated twice before the cells were finally sorted into single-cell clones. Stably transfected clones were isolated by flow cytometry from a population of GFP-positive cells. These stable GFP-expressing cells were used for all mouse studies.

siRNA Study:

TC1 cells were transfected with siRNAs targeted against IL-33 (GS 77125), against H2-K1 (GS 1027416), untargeted siRNA (1022076) using HiPerFect Transfection reagent (301704) or left untreated. All reagents were purchased from Qiagene. The expression level of IL-33 and H2-K1 was assessed in 72 to 96 hours.

RT-PCR Analysis:

Total cellular RNA was extracted using Illustra RNAspin Mini Kit (GE Healthcare Life Science). Reverse transcription of 1 µg of total cellular RNA was performed using the reverse transcription (RT) kit (SSII RT) from Invitrogen with a total volume of 20 µl. Two-microliter aliquots of cDNA were used as a template for PCR in a total 50-µl reaction mixture containing 1×PCR buffer, 250 µM deoxynucleotide triphosphate, 1.5 mM MgCl2, 200 nM of each primer, and 2.5 U Taq or Platinum Taq DNA polymerase. cDNA amplifications were carried out in a T-gradient thermocycler (Biometra, Goettingen, Germany) with 25 to 35 cycles of denaturation (1 min, 95° C.), annealing (1 min, 54 to 64° C.), and elongation (2 min, 72° C.). The cycling was concluded with a final extension at 72° C. for 10 min. Twenty microliters of amplified products were analyzed on agarose gels, stained with ethidium bromide, and photographed under UV light. Primers used for PCR amplifications (Integrated DNA Technologies, Coralville, Iowa):

```
TAP1
                                        (SEQ ID NO: 1)
    F: 5'-TGGCTCGTTGGCACCCTCAAA-3', (SEQ ID NO: 2)
    R: 5'-TCAGTCTGCAGGAGCCGCAAGA-3';
```

β-actin

F: 5'-ATGGATGACGATATCGCTGC-3', (SEQ ID NO: 3)

R: 5'-TTCTCCAGGGAGGAAGAGGAT-3'; (SEQ ID NO: 4)

IL-33

F: 5'-AGGAAGAGATCCTTGCTTGGCAGT-3'; (SEQ ID NO: 5)

R: 5'-ACCATCACCTTCTTCCCATCCACA-3'; (SEQ ID NO: 6)

H2-K1

F: 5'-CACGCTGCTCCTGCTGTT-3'; (SEQ ID NO: 7)

R: 5'-TTCACGCTAGAGAATGAGGGT-3'. (SEQ ID NO: 8)

Real-Time Quantitative PCR Analysis:

Purified genomic DNA was used as a template for amplifications using 200 to 500 nM of each primer and 1 μl SYBR Green Taq ReadyMix (Roche, Mannheim, Germany) in a total 10 μl reaction mixture. Thirty-five to forty cycles of denaturation (5 s, 95° C.), annealing (5 s, 61 to 63° C.), and elongation (20 s, 72° C.) were carried out using a Roche LightCycler 480 instrument.

Western Blots:

RIPA Lysis Buffer System (sc-24948, Santa Cruz Biotechnology) was used for protein isolation from cells and tissues. To shear genomic DNA, lysed samples were passed ten times through a 21-gauge needle then incubated on ice for 30 minutes. The homogenate was centrifuged at 4° C. at 14000×g for 10 minutes. Protein concentrations from the supernatants were determined by BCA assay (Pierce) and samples were adjusted to final concentration of 50 μg per lane. Proteins were separated with 10% sodium dodecyl sulfate-polyacrylamide gel electrophoresis and transferred to nitrocellulose membranes (Bio-Rad). Blots were blocked with 5% skim milk in phosphate-buffered saline and incubated overnight at 4° C. with the anti-IL-33 [Nessy-1] (ab54385, Abcam) mouse monoclonal antibody, mouse antiserum directed toward the region of H2-K1 encoded by exon 8 (kindly provided by Dr. Williams, University of Toronto), rabbit anti-mouse TAP-1 polyclonal antibodies (made in-house by Jefferies' lab (Zhang et al., 2007)), followed by the secondary antibodies, which were complimentary to the species of the primary conjugated with Alexa Fluor 680 (Invitrogen).

B3Z Assay:

B3Z T cells express a TCR that specifically recognizes OVA (257-264) (SIINFEKL) in the context of H2-K1 in addition to carrying a b-galactosidase (lacZ) construct driven by nuclear factor of activated T cells elements from the interleukin 2 promoter (Shastri and Gonzalez, 1993). Genetically modified tumor cells were incubated for 16 h with OVA (257-264) at a concentration of 10 ug/ml, before being washed and incubated overnight with B3Z T cells, which are a T cell hybridoma that are activated by the recognition of H2-K1 in association with OVA (257-264) at a cell ratio of 1:1. Chlorophenolred-β-galactopyranoside (CPRG), a b-galactosidase substrate, was used to assay LacZ activity in total culture lysates from B3Z T cells. The absorbance (560 nm) of culture wells was read after 4 h of incubation.

CD8+ T Cell Isolation and Co-Culture with ILC2s:

Splenic CD8+ T cells were isolated from OT-1 mouse using the Negative Selection EasySep CD8+ T cell Enrichment Kit (19753, StemCell Thechnologies). CD8+ T cells isolated from OT-1 mouse express a TCR that specifically recognizes OVA (257-264) (SIINFEKL) in the context of H2-K1. CD8+ DCs were isolated from B/6 mouse using the "CD8+ Dendritic Cell Isolation kit, mouse" (130-091-169, Miltenyi Biotec, Inc.). Metastatic prostate tumor cells (LMD+pTAP1/GFP, 2×10$^4$ cells/well) were cultured with and without ILC2s (1×10$^4$) in a 96-well plate. 48 hours later cells were pulsed for ~4 h with OVA (257-264) peptide at a concentration of 10 ug/ml, before being incubated with freshly isolated CD8+ T cells (2×10$^4$ or 4×10$^4$ cells/well) and CD8+DCs together for four days.

Antibodies, Reagents, FACS Sorting, and Analysis

Antibodies Used for Flow Cytometry to Check for Chimerism in Mice after Bone Marrow Transplantation:

FITC-conjugated CD45.1 (11-0453-81, #A-20) and PerCP-Cy5.5-conjugated CD45.2 (45-0454-80, #104) were purchased from eBioscience;

Antibodies Used to Block Fc Receptors:

CD16/32 (564220, BD Pharmingen)

Excluding Nonviable Cells from Flow Cytometry:

Fixable Viability Dye eFluor 780 (65-0865-14, eBioscience)

ILC2 Isolation:

The following antibodies were purchased from eBioscience. FITC-conjugated lineage marker monoclonal antibodies against: CD3, CD8a, TCRb, CD19, B220, NK1.1, Mac-1, GR-1, and Ter119; phycoerythrin (PE)-conjugated antibody against CD127; PerCP-Cy5.5-conjugated antibody against ST2; BV600 AmCyan-conjugated antibody against Thy 1.2.

CD4, CD8 Staining:

APC-conjugated antibody against CD4 (553051, RM4-5, BD Bioscience) and PE-Cy7-conjugated antibody against CD8a (25-0081-82, 53-6.7, eBioscience).

H2-K1 Expression:

PE-conjugated anti-Kb mouse monoclonal antibody (553570, BD Pharmingen).

Granzyme b Expression:

APC-conjugated antibody against CD8a (47-0081-80), Fixation and Permeabilization buffer Kit (88-8823-88), PE-conjugated antibody against Granzyme b (12-8898-80). All reagents were bought from eBioscience.

Flow Cytometry:

BD FACS Aria II was used for cell sorting and phenotypic analysis. The program FlowJo v.8.6 was used for data analysis.

Mice:

C57BL/6 and C57Bl/6.Pep3b mice were purchased from the Jackson Laboratories and maintained in the British Columbia Cancer Research Centre (BCCRC) pathogen-free animal facility. RORα −/− (C57BL/6J-Rorasg-3J/J) mice were made at the BCCRC by Fumio Takei and maintained at the BCCRC. Mice were used at 4-8 weeks of age. These experiments were approved by the Animal Care Committee of the University of British Columbia. Animals were maintained and euthanized under humane conditions in accordance with the guidelines of the Canadian Council on Animal Care.

BMT and Tumor Establishment:

B6.Pep3b (B6.SJL-Ptprca Pepcb/BoyJ) mice were lethally irradiated (1,000 Rads) and received transplantation of 10$^7$ whole bone marrow cells from 4-week-old WT or RORα −/− (C57BL/6J-Rorasg-3J/J) mice. Mice were given ciprofloxacin for 4 weeks. The quality of BM transplantation was analysed by FACS 8-16 weeks later by determining the ratio between CD45.1 and CD45.2 positive cells in peripheral blood. Genetically modified tumor cells (50 µl of 5×105) were injected into chimera animals subcutaneously. Tumor growth was monitored by measuring tumor dimensions with calipers. Tumor length and width measurements were obtained three times weekly. Tumor volumes were calculated according to the equation tumor volume=length× width×height×π/6 with the length (mm) being the longer axis of the tumor. Animals were weighed at the time of tumor measurement.

Primary Leukocyte Preparation:

Cell suspensions were prepared from tumors and lymph nodes (Halim et al., 2012). Tissues were cut into small pieces with a razor and digested for 40 min in MEM, 10% FBS, penicillin and streptomycin (P+S), 50 mM 2-mercaptoethanol (2ME), Collagenase IV (Invitrogen), and DNase (Sigma) at 37° C. Digested tissue was pushed through a 70 µm strainer, and Percoll (GE Healthcare) gradient enrichment of leukocytes followed.

Isolation of ILC2 Cells:

Single cells were incubated with 2.4G2 for blocking Fc receptors. After staining with FITC-conjugated lineage marker mAbs (CD3, CD8a, TCRb, CD19, B220, NK1.1, Mac-1, GR-1, and Ter119), PE-conjugated CD127, PerCP-Cy5.5-conjugated ST2, BV600 AmCyan-conjugated Thy 1.2 cells were purified/sorted by FACS.

Cytokine Production Assay:

Flow cytometry-purified cells were cultured in 200 ml RPMI-1640 media containing 10% FBS, P+S, and 2 ME at 37 C. Cells were stimulated with TSLP (10 ng/ml) and IL-33 (10 ng/ml). The secretion of IL-5, IL-13 was assessed by (eBioscience) enzyme-linked immunosorbent assays (ELISAs) according to the manufacturer's protocol.

ELISA:

Enzyme-linked immunosorbent assays (ELISAs) were performed according to the manufacturer's protocol: IL-33 Ready-Set-go ELISA kit (88-7333-88, eBioscience)); IL-5 Ready-Set-go ELISA kit (88-7054-22, eBioscience); IL-13 Ready-Set-go ELISA kit (88-7137-88; eBioscience).

Immunohistochemistry:

Tumors were embedded in Tissue-Tek O.C.T. media (Sakura) on dry ice and immediately stored at −80° C. until sectioning. 101 µm thick sections were collected on Leica cryostat and stored at −80° C. until staining. Slides were removed from −80° C., fixed in cold acetone or acetone: methanol. Following washing in TBS, slides were incubated with protein block and subsequently incubated with specific antibodies overnight. Antibodies used: anti-CD4 (553043, BD Bioscience), anti-CD8 (553027, BD Bioscience), anti-MHCI (15681, Abcam), anti-FoxP3 (54501, Abcam), anti-Ly-6G (MAB1037, R&D System), anti-CD68 (53444, Abcam). Appropriate horseradish peroxidase (HRP) conjugated secondary antibodies were used for detection of the primaries and developed with DAB chromogen. Slides were counter stained with haematoxylin and eosin (H&E) and dehydrated in ethanol and xylene. Slides were then cover slipped and imaged with an Aperio ScanScope at 20× magnification.

Human Prostate Samples:

mRNA Sequencing Cohort:

RNA-sequencing data from the Vancouver Prostate Centre was obtained and analyzed exactly as previously described (PMID: 25155515). Public data from (PMID: 20579941) was explored using the cBioPortal (PMID: 22588877).

Immunohistochemistry:

Immunohistochemical stains were conducted at the Vancouver Prostate Centre using a Ventana autostainer model Discover XT (Ventana Medical System, Tuscon, Ariz.) with enzyme labeled biotin streptavidin system and solvent resistant DAB Map kit using 1/50 concentration of rabbit polyclonal IL-33 antibody (HPA024426 Sigma; Sigma-Aldrich). Staining was performed on 342 prostate cancer specimens obtained from the Vancouver Prostate Centre. The H&E slides were reviewed and the desired areas were marked on them and their correspondent paraffin blocks. 5 TMAs were manually constructed (Beecher Instruments, MD, USA) by punching duplicate cores of 1 mm for each sample. Stained slides were digitalized with the SL801 autoloader and Leica SCN400 scanning system (Leica Microsystems) at magnification equivalent to ×20. Representative cores (clearly positive, clearly negative and mixed positive/negative) were manually identified by an experienced pathologist (LF) and a four-point scale was assigned as follows: 0 represents no staining in any tumor cells, 1 represents a faint or focal, or questionably present stain, 2 and 3 represents a stain of convincing intensity in a majority of cells. For comparisons, a score of 0 or 1 was considered low IL-33 expression.

Statistics:

Data were analyzed with Excel. A Student's t test was used for determining statistical significance between groups; $p \leq 0.05$ was considered significant. The statistical analysis of microarray results was carried out with FlexArray (Genome Quebec).

Example 4: Adoptive Transfer of Type 2 Innate Lymphocytes as Immunotherapeutic Against Cancer Current immune therapeutic approaches are mainly based on strategies, which inhibit the immune suppression and/or boost the immune activation. Combinations of different approaches may affect different steps of the Cancer Immunity Cycle resulting in durable clinical responses. Aiming to combine the modification of suppressive tumor microenvironment (antigen-independent factors) together with activation of tumor-specific immune responses (antigen-dependent factors), we conducted an adoptive transfer of in vitro activated ILC2 cells.

It has been generally accepted that antigen-independent factors, such as local microenvironment, can influence the regulatory processes in tumor tissue via chemokine- and cytokine-related signaling pathways highlighting context-specific biological functions of tumor tissue framework. One of the prompt responders to the tissue insult is innate lymphoid group of cells (ILCs), which can modify immune responses to the needs of local tissue microenvironment. Two ILC subsets have been implicated in tumor immunity including Group 1 ILCs (ILC1; natural killer (NK) cells) 17 and Group 3 ILCs (ILC3). The role of Group 2 ILCs (ILC2) in tumor immune-surveillance has not yet been established, although indirect links have been alluded to.

Here it is reported that mice genetically lacking ILC2s have significantly increased tumor growth rates. It is also demonstrate that adoptive transfer of ILC2's completely abrogates the growth of tumors with high IL-33 content, which is capable to up-regulate MHC1 expression reinforcing tumor-specific immune responses. Thus, the antigen-independent factors, which influence the effectiveness of endogenous T cell pool, are of a great importance in combination with strategies enhancing the tumor specific recognition at later steps of the Cancer-Immunity Cycle. Our data supports the conclusions that ILC2s mediate tumor immune surveillance, and adoptive transfer of ILC2s is a new immunotherapeutic approach to aid in the eradication of cancers.

The ILC family is a cytokine-producing group of cells phenotypically characterized by the absence of re-arranged antigen-specific receptors. However, all the ILCs express γc-subunit of cytokine receptor, which indicates the importance of γc-dependant cytokines in ILC development and function. ILCs are currently divided into three main groups, which are defined by the cytokines they produce. Variability of surface expressing molecules marks different ILC subsets, activation stages and the tissue of origin. Interest here is in Group 2 ILCs (ILC2). This cell type can be purified by Flow Cytometry as lineage negative cell population expressing some lymphoid and hematopoietic markers: lymphoid progenitor marker IL7Ra (CD127), IL2Ra (CD25), IL17BR (a subunit of IL25R), the IL-33 receptor T1/ST2 chain, Thy1.2 (CD90.2), stem cell antigen 1 (Sca1), CD45, c-kit (CD117). The isolated cell population responded to treatment with IL-33 and TSLP producing type 2 cytokines (IL-5 and IL-13) and are considered to be innate helper cells. IL-13 can act as pro- and anti-inflammatory mediator, depending on the microenvironment and target specific cells. Thus, 11-13 can suppress cytokine production by monocytes, activate TGF-b secretion by MDSC and promote 123 macrophages to acquire alternatively activated phenotype. On the other hand, secretion of IL-13 by ILC2s is important for the migration of activated dendritic cells (DCs) to the draining lymph nodes, where T cell priming and activation takes place. Additionally, IL-13 secretion at early stages of tumor development can drive the production of eosinophil chemo-attractant, eotaxin, by epithelial cells with consequent eosinophil recruitment. Upon arrival at the site of an immunological response, eosinophils require IL-5 for activation and survival and this is also secreted by ILC2s 11. Eosinophils promote tumor rejection through secretion of CD8+ and CD4+ T cells chemo-attractants, such as CXCL9, CXCL10, CCL5 (via STAT1) or CCL17, CCL22 (via STAT6), which allow the trafficking of T cells to the tumor site. Moreover, ILC2s are capable of influencing adaptive immune responses through cell-to-cell contact via MHC-II molecules that they express on their cell surface. Here, it is demonstrated that the Adoptive transfer of activated ILC2s has resulted in a complete growth arrest of primary murine lung carcinoma and propose a possible mechanism of action Material and Methods Cell Lines Murine Prostate Cancer Model:

The PA and LMD cell lines were used as models of nonmetastatic and metastatic prostate cancer, respectively. PA is a primary murine prostate cancer cell line derived from a 129/Sv mouse using a mouse prostate reconstitution model system that displays high expression of MHC-I. LMD is a metastatic TAP- and MHC-I deficient derivative of PA which emerged as a metastatic daughter after escaping and metastasising from the kidney capsule during serial transfer of the PA cells (Lee et al., 2000). The pTAP-1-EGFP-stably transfected LMD cells (Setiadi 2005) were used to study the mechanism underlying the differential activation of TAP-1 promoter in TAP-deficient LMD cells.

Murine Lung Tumor Model:

The TC1 cell line is a murine lung tumor model derived from primary lung epithelial cells of C57BL/6 mice immortalized using the amphotropic retrovirus vector LXSN16 carrying human papillomavirus genes E6/E7, and subsequently transformed with pVEJB plasmid expressing the activated human c-Ha-ras oncogene. TC1 cells display high expression of TAP-1 and MHC-I. The cell line A9 was derived from the TC1 tumor cell line and display spontaneous down-regulation of MHC-I (or H2-K1) by immunoselection in vivo during immunization/challenge experiment (Smahel et al.). All the above cell lines were grown in Dulbecco's modified Eagle medium, supplemented with 10% heat-inactivated fetal bovine serum, 2 mM 1-glutamine, 100 U/ml penicillin, 100 µg/ml streptomycin, and 10 mM HEPES.

RT-PCR Analysis:

Total cellular RNA was extracted using Illustra RNAspin Mini Kit (GE Healthcare Life Science). Reverse transcription of 1 µg of total cellular RNA was performed using the reverse transcription (RT) kit (SSII RT) from Invitrogen with a total volume of 20 µl. Two-microliter aliquots of cDNA were used as a template for PCR in a total 50-µl reaction mixture containing 1×PCR buffer, 250 µM deoxynucleotide triphosphate, 1.5 mM MgCl2, 200 nM of each primer, and 2.5 U Taq or Platinum Taq DNA polymerase. cDNA amplifications were carried out in a T-gradient thermocycler (Biometra, Goettingen, Germany) with 25 to 35 cycles of denaturation (1 min, 95° C.), annealing (1 min, 54 to 64° C.), and elongation (2 min, 72° C.). The cycling was concluded with a final extension at 72° C. for 10 min. Twenty microliters of amplified products were analyzed on agarose gels, stained with ethidium bromide, and photographed under UV light. Primers used for PCR amplifications (Integrated DNA Technologies, Coralville, Iowa):

```
TAP1
F: 5'-TGGCTCGTTGGCACCCTCAAA-3',

R: 5'-TCAGTCTGCAGGAGCCGCAAGA-3';

β-actin
F: 5'-ATGGATGACGATATCGCTGC -3',

R: 5'-TTCTCCAGGGAGGAAGAGGAT-3';

IL-33
F: 5'-AGGAAGAGATCCTTGCTTGGCAGT-3';

R: 5'-ACCATCACCTTCTTCCCATCCACA-3';

H2-K1
F: 5'-CACGCTGCTCCTGCTGTT-3';

R: 5'-TTCACGCTAGAGAATGAGGGT-3'.
```

Western Blots:

RIPA Lysis Buffer System (sc-24948, Santa Cruz Biotechnology) was used for protein isolation from cells and tissues. To shear genomic DNA, lysed samples were passed ten times through a 21-gauge needle then incubated on ice for 30 minutes. The homogenate was centrifuged at 4° C. at 14000×g for 10 minutes. Protein concentrations from the supernatants were determined by BCA assay (Pierce) and samples were adjusted to final concentration of 50 µg per lane. Proteins were separated with 10% sodium dodecyl sulfate-polyacrylamide gel electrophoresis and transferred to nitrocellulose membranes (Bio-Rad). Blots were blocked with 5% skim milk in phosphatebuffered saline and incubated overnight at 4° C. with the anti-IL-33 [Nessy-1] (ab54385, Abcam) mouse monoclonal antibody, mouse antiserum directed toward the region of H2-K1 encoded by exon 8 (kindly provided by Dr. Williams, University of Toronto), rabbit anti-mouse TAP-1 polyclonal antibodies (made in-house by Jefferies' lab (Zhang et al., 2007)), followed by the secondary antibodies, which were complimentary to the species of the primary conjugated with Alexa Fluor 680 (Invitrogen).

CD8+ T Cell Isolation and Co-Culture with ILC2s:

Splenic CD8+ T cells were isolated from OT-1 mouse using the Negative Selection EasySep CD8+ T cell Enrichment Kit (19753, StemCell Thechnologies). CD8+ T cells isolated from OT-1 mouse express a TCR that specifically recognizes OVA (257-264) (SIINFEKL) in the context of H2-K1. CD8+ DCs were isolated from B/6 mouse using the "CD8+ Dendritic Cell Isolation kit, mouse" (130-091-169, Miltenyi Biotec, Inc.). Metastatic prostate tumor cells (LMD+pTAP1/GFP, 2×104 cells/well) were cultured with and without ILC2s ($1\times10^4$) in a 96-well plate. 48 hours later cells were pulsed for ~4 h with OVA (257-264) peptide at a concentration of 10 ug/ml, before being incubated with freshly isolated CD8+ T cells ($2\times10^4$ or $4\times10^4$ cells/well) and CD8+DCs together for four days.

Antibodies, Reagents, FACS Sorting, and Analysis:

Antibodies used for flow cytometry to check for chimerism in mice after bone marrow transplantation: FITC-conjugated CD45.1 (11-0453-81, #A-20) and PerCP-Cy5.5-conjugated CD45.2 (45-0454-80, #104) were purchased from eBioscience; Antibodies used to block Fc receptors: CD16/32 (564220, BD Pharmingen) Excluding nonviable cells from flow cytometry: Fixable Viability Dye eFluor 780 (65-0865-14, eBioscience).

ILC2 Isolation:

The following antibodies were purchased from eBioscience. FITC conjugated lineage marker monoclonal antibodies against: CD3, CD8a, TCRb, CD19, B220, NK1.1, Mac-1, GR-1, and Ter119; phycoerythrin (PE)-conjugated antibody against CD127; PerCP-Cy5.5-conjugated antibody against ST2; BV600 AmCyan-conjugated antibody against Thy 1.2.

CD4, CD8 Staining:

APC-conjugated antibody against CD4 (553051, RM4-5, BD Bioscience) and PE-Cy7-conjugated antibody against CD8a (25-0081-82, 53-6.7, eBioscience).

H2-K1 Expression:

PE-conjugated anti-Kb mouse monoclonal antibody (553570, BD Pharmingen). 5.2.5.6 Granzyme b expression: APC-conjugated antibody against CD8a (47-0081-80), Fixation and Permeabilization buffer Kit (88-8823-88), PE-conjugated antibody against Granzyme b (12-8898-80). All reagents were bought from eBioscience. 5.2.5.7 Flow Cytometry: BD FACS Aria II was used for cell sorting and phenotypic analysis. The program FlowJo v.8.6 was used for data analysis.

Mice:

C57BL/6 mice were purchased from the Jackson Laboratories and maintained in the British Columbia Cancer Research Centre (BCCRC) pathogen-free animal facility. Mice were used at 4-8 weeks of age.

Tumor Establishment:

Tumor cells (50 μl of $5\times10^5$ in HBSS (ThermoFisher Scientific) for donors and 50 μl of $5\times10^4$ for recipients) were injected into animals subcutaneously into the left flank. Tumor growth was monitored by measuring tumor dimensions with calipers. Tumor length and width measurements were obtained three times weekly. Tumor volumes were calculated according to the equation tumor volume=length×width×height×p/6 with the length (mm) being the longer axis of the tumor. Animals were weighed at the time of tumor measurement.

Primary Leukocyte Preparation:

Cell suspensions were prepared from tumors, local lymph nodes (mesenteric, inguinal and lumbar) and lungs. (Tissues were cut into small pieces with a razor and digested for 40 min in MEM, 10% FBS, penicillin and streptomycin (P+S), 50 mM 2-mercaptoethanol (2ME), Collagenase IV (Invitrogen), and DNase (Sigma) at 37° C. Digested tissue was pushed through a 70 μm strainer, and Percoll (GE Healthcare) gradient enrichment of leukocytes followed.

Isolation of ILC2 Cells:

Single cells were incubated with 2.4G2 for blocking Fc receptors. After staining with FITC-conjugated lineage marker mAbs (CD3, CD8a, TCRb, CD19, B220, NK1.1, Mac-1, GR-1, and Ter119), PE-conjugated CD127, PerCP-Cy5.5-conjugated ST2, BV600 AmCyan-conjugated Thy 1.2 cells were purified/sorted by FACS.

Adoptive Cell Transfer:

To isolate ILC2 cells for future experiment, primary murine lung carcinoma tumors (TC1) were established on donor C57BL/6 animals. Approximately three weeks later ILC2 cells were purified from donor-lungs and donor-tumors by flow cytometry. Purified cells were cultured in RPMI-1640 media containing 10% FBS, P/S, 2ME and stimulated by IL-33 (10 ng/ml) and TSLP (10 ng/ml) for 5 days. Expanded ILC2 cells ($1.5\times103$ cells to max of 200 μl/20 g of PBS) or PBS controls were injected by tail vein into recipient-mice on the next day after tumor establishment.

Cytokine Production Assay:

Flow cytometry-purified cells were cultured in 200 μl RPMI-1640 media containing 10% FBS, P+S, and 2 ME at 37 C. Cells were stimulated with TSLP (10 ng/ml) and IL-33 (10 ng/ml). The secretion of IL-5, IL-13 was assessed by (eBioscience) enzyme-linked immunosorbent assays (ELISAs) according to the manufacturer's protocol.

ELISA:

Enzyme-linked immunosorbent assays (ELISAs) were performed according to the manufacturer's protocol: IL33 Ready-Set-go ELISA kit (88-7333-88, eBioscience)); IL-5 Ready-Set-go ELISA kit (88-7054-22, eBioscience); IL-13 Ready-Set-go ELISA kit (88-7137-88; eBioscience).

Immunohistochemistry:

Tumors were embedded in Tissue-Tek O.C.T. media (Sakura) on dry ice and immediately stored at −80° C. until sectioning. 101 μm thick sections were collected on Leica cryostat and stored at −80° C. until staining. Slides were removed from −800 C, fixed in cold acetone or acetone:methanol. Following washing in TBS, slides were incubated with protein block and subsequently incubated with specific antibodies overnight. Appropriate horseradish peroxidase (HRP) conjugated secondary antibodies were used for detection of the primaries and developed with DAB chromogen. Slides were counter stained with haematoxylin and eosin (H&E) and dehydrated in ethanol and xylene. Giemsa staining was used to detect eosinophils. Slides were then cover slipped and imaged with an Aperio ScanScope at 20× magnification.

Results:

The frequency of ILC2s is elevated in primary tumors and metastatic tumors expressing IL-33 The development and function of ILC2s are strongly dependent on the IL-33 presence in the microenvironment. The difference in IL-33 expression between primary and metastatic tumors enabled examination of the involvement of ILC2s and IL-33 in cancer progression. First, the presence of ILC2s was detected in the disaggregated tumor tissue using flow cytometry. ILC2s were identified as cells that did not express leukocyte lineage cell-surface markers (Lin: CD3, CD8, TCRb, CD19, CD11c, Gr-1, NK1.1, Ter119), while exhibiting a distinct pattern of cell-surface marker expression of the IL-33 receptor T1/ST2 (ST2) chain, IL-7 receptor subunit IL-7Ra (CD127) and Thy1.2 (CD90.2) (FIG. 75a). The population of LinST2+CD127+CD90.2+ cells was further shown to be morphologically similar to lymphocytes: round in shape with a high nuclear to cytoplasm ratio. Upon isolation in vitro, this cell subset was able to grow and secrete IL-5 and IL-13 after stimulation with a combination of thymic stromal lymphopoietin (TSLP) and IL-33 (FIG. 75b). These data suggest that the population of LinST2+CD127+CD90.2+ cells detected in tumors was phenotypically and functionally ILC2s. Next, the level of ILC2 infiltration into primary (TC1) or metastatic (A9) tumors, with or without IL-33 complementation was assessed. A significant decrease in the numbers of ILC2s found within the disaggregated tissues of metastatic tumors (A9) versus primary (TC1) or IL-33 complemented A9 cells was observed (FIG. 75c). These data suggest that ILC2s are involved in immune surveillance towards tumors.

Demonstration that ILC2s Aid in Immune Recognition of Cancers In Vivo:

To directly examine the role of ILC2s and IL-33 in cancer progression, a comparison of the progression of metastatic A9 tumors with and without IL-33 complementation in RORα-deficient mice and wild type mice was conducted. RORα-/- mice specifically lack ILC2s, but maintain normal numbers of NK cells and ILC3s 16. Bone marrow chimeras were generated by reconstitution of lethally irradiated B6.Pep3b (CD45.1) mice with whole bone marrow (BM) cells from either 4-week-old wild type or RORα-/- (both CD45.2) mice. Bone marrow transplant recipients were allowed to recover for 6 weeks, and the quality of the bone marrow transplantation was analysed by FACS, determining the ratio between CD45.1 and CD45.2 positive cells in peripheral blood. All the transplants were between 92-96% efficient. A9, A9+IL-33, TC1 cells were then injected subcutaneously and allowed to grow. It was observed that IL-33-expressing cells significantly inhibited tumor growth rate in wild type mice compared to mice lacking ILC2s (FIG. 76a). Interestingly, the numbers of ILC2s found in lymph nodes was also increased in animals bearing IL-33-expressing tumors (FIGS. 76b and 77b). The numbers of CD4+ and CD8+ T cells were unaffected, when comparing RORα-/- to wild-type animals (FIG. 76c). Metastasized tumor cells were detected in disaggregated Adrenal glands (FIG. 77a) isolated from RORα-/- chimeras bearing primary tumors (TC1) with local growing potential. This observation suggests that RORα transcription factor is important for limiting metastasis of primary tumors, which otherwise leads to metastatic spread of the disease. Collectively, these data demonstrate that IL-33 gene-complementation can modify the tumor progression and support the clear conclusion that ILC2s function to limit metastasis and participate in cancer immune-surveillance through RORα-IL-33-ILC2 axis.

The Effect of ILC2s on Cytolytic T Cell Effector Mechanisms:

To assess the effect of ILC2 on cytolytic T cell effector mechanisms, ILC2 from tumors of donor-mice were isolated. First, primary murine lung carcinoma tumors (TC1) were established in donor C57BL/6 animals. Next, ILC2 cells were purified from resected tumors by flow cytometry, approximately three weeks after tumor inoculation. After that metastatic prostate tumor cells (LMD) were cultured with and without activated ILC2s. 48 hours later cells were pulsed for ~4 h with OVA (257-264) peptide and incubated with freshly isolated CD8a+ T cells and CD8+ DCs together for four days. These particular LMD cells express EGFP under the transcriptional control of the TAP1 promoter 19, where an increase in EGFP expression correlates with an increase in both TAP1 and MHC-1 expression. The presence of ILC2s in the system elevated the EGFP expression of the LMD cells, which are normally TAP-deficient metastatic cells. This observation suggests that the direct interaction with the ILC2s or with cytokines secreted by them enables the LMD cells to overcome the deficiencies responsible for the decreased activity of the TAP-1 promoter/expression (FIG. 78a). The elevated level of granzyme b in the context of CD8a+ mirrors the effect of ILC2s on cytolytic T cell effector mechanisms in vitro (FIGS. 78b and 78c).

Adoptive Transfer of ILC2's Mediates Cancer-Free Survival:

To investigate whether ILC2s can act as an cell-based immunotherapy, the effect of ILC2 cells was examined in vivo by conducting an adoptive transfer of activated donor-derived ILC2s into recipient animals bearing primary tumors. To establish tumors in recipient mice, murine lung carcinoma cells (50 µl of $5 \times 10^4$) were injected subcutaneously into the right flank of C57BL/6 mouse (Day 0). Donor-derived activated lung and tumor ILC2 cells (~$1.2 \times 10^3$-$1.5 \times 10^3$ cells in 200 ul of PBS) or PBS controls were injected by tail vein into recipient mice one day (Day 1) after tumor establishment.

A complete growth arrest of primary tumors was detected in mice after adoptive transfer on ILC2s isolated from donor lungs (100% reduction) (FIGS. 79a and 79b). Interestingly, ILC2s isolated from donor tumors decreased the primary tumor volume by only 60%, suggesting that phenotypical differences of ILC2s isolated from different tissues may affect their functionalities. In general, ILC2s isolated from lungs phenotypically have higher number of ST2-receptors. Therefore, in the microenvironment with high IL-33 content, the downstream signaling through ST2 receptors can be up-regulated with consequent enhancement of cytokine-effector functions attracting more immune cells to the tumor site.

The increased number of innate immunity cells in tumor sections of ILC2 recipients suggests that these tumor-infiltrating immune cells may mediate protective anti-tumor immunity in murine lung carcinoma. For example, eosinophils could be seen at the tumor periphery adjacent to the normal tissue before ILC2 transfer, whereas after the treatment, ILC2-generated products appeared to modify the microenvironment and allow eosinophils to flow into the tumor tissue and exert an anti-tumor effect (FIG. 78c).

Discussion:

In this example, it was demonstrate for the first time, the direct involvement of ILC2s in immune recognition of tumors. Overall the down-regulation of IL-33 and subversion of ILC2's takes place concomitantly with the transition from primary to metastatic tumors and represents an entirely new form of tumor immune-escape.

The difference in IL-33 levels within the tumor microenvironment of the primary and metastatic carcinomas led us to study ILC2s, whose development and functioning are strongly dependent on IL-33 expression. A significant decrease of the ILC2 count in disaggregated tissues of metastatic tumors versus primary or IL-33-complemented neoplasms was observed. These data suggests that ILC2s are involved in immune-surveillance towards tumors, thus linking cancer progression to the absence of ILC2s. The generation of bone marrow chimeras made it possible to study the mechanistic details of the involvement of ILC2s in the modification of tumor progression. The resulting RORα-deficient mice have significantly smaller number of ILC2s.

These data suggest that RORα transcription factor is essential for the generation of ILC2s, as well as for reprogramming the tumor cell potential to metastasise and colonize distal organs. It was observed that stable transfection of IL-33-gene into metastatic cells significantly inhibited tumor growth rate in wild type mice comparing to mice lacking ILC2s, demonstrating, for the first time that ILC2s participate in cancer immune-surveillance through RORα-ILC2 pathway. Possibly, RORα-IL-33-activated ILC2s play an important role in tumor elimination by recruiting other cells, such as Th2 cells via expression of MHC-II molecules dendritic cells via IL-13 production 8 and/or eosinophils via IL-5 production.

In the light of these observations, the role of eosinophils into tumor rejection through CD8+ T cells chemo-attraction, the missing link of the crucial importance of ILC2 cells in cancer immune-surveillance becomes clear: IL-33 reconstitutes immunological recognition of tumors and activates ILC2s, which further shape the innate and adaptive anti-cancer immunity. A cellular mechanism model is proposed (FIG. 80).

It is demonstrate for the first time that adoptive transfer of activated ILC2 cells drastically reduces tumor growth rate, influencing the immune response to tumors, and therefore, may provide a generalizable approach to cancer immunotherapies. Adoptive transfer of ILC2s appears to be a promising and hitherto unreported new arrow in the quiver of cancer therapies. This approach affects antigen-dependent and -independent factors at different steps in cancer immune-surveillance. The ratio of adoptively transferred ILC2s to tumor cells is on the order of 1 ILC2 to ~30-40 tumor cells, whereas in models of human tumor grown in NSG mouse, the ratio of CAR+ T cells to tumor cells is on the order of ~5-10 T cells to 1 tumor cell. Furthermore, in the case of CAR-based approaches, T cell-preparation in vivo takes much longer than 5 days and lympho-depletion via radiation is required prior to cell transfer. Thus, when compared to similar studies involving adoptively transferred CAR+ cells, the ILC2 approach appears superior due to the relatively small number of cells required to promote tumor free survival and the possibility of this approach being general applicability to patients without regards to antigen specificity.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

REFERENCES

Alimonti, J., et al. (2000a). Nature biotechnology 18, 515-520.
Alimonti, J., et al. (2000b). Nat Biotechnol 18, 515-520.
Alpan, R. S., et al. (1996). Cancer Res 56, 4358-4361.
Andratschke, M., et al. (2003). Anticancer Res 23, 1467-1471.
Blades, R. A., et al. (1995). et al. Urology 46, 681-686
Canadian Cancer Society (2012). General cancer statistics at a glance.
Carretero, R., et al. (2015). Nat Immunol 16, 609-617.
Carriere, V., et al. (2007). et al. Proc Natl Acad Sci USA 104, 282-287.
Cayrol, C., and Girard, J. P. (2014). et al. Curr Opin Immunol 31, 31-37.
deLeeuw, R. J., et al. (2015). Cancer Immunology Research 3, 245-253.
Delp, K., et al. (2000). Bone Marrow Transplant 25 Suppl 2, S88-95.
Drake, L. Y., et al. (2014). Allergy 69, 1300-1307.
Fine, C. I et al. (2002). J Immunol 169, 6012-6019.
Fridman, W. H., et al. (2012). Nat Rev Cancer 12, 298-306.
Gabathuler, et al. (1994). The Journal of Exp Med 180, 1415-1425.
Gao, X., et al. (2015). J Immunol 194, 438-445.
Giorda, E., et al. (2003). Cancer Res 63, 4119-4127.
Guabiraba, R., et al. (2014). Mucosal immunology 7, 1079-1093.
Halim, T. Y., et al. (2012). Immunity 37, 463-474.
Hallen L. C., et al. (2007). J. Interferon Cytokine Res. 27(8), 675-680.
Hanahan, D., and Weinberg, R. A. (2011). Cell 144, 646-674.
Harris, A. L., et al. (1994). Cancer 74, 1021-1025.
Janeway, C., Travers, P., et al. (2008). Immunobiology: the Immune System in Health and Disease., 7th ed. edn (New York: NY Garland Publishing).
Johnsen, A. K., et al. (1999). J Immunol 163, 4224-4231.
Kaklamanis, L., et al. (1995). Cancer Res 55, 5191-5194.
Karttunen, J., et al. (1992). Proc Natl Acad Sci USA 89, 6020-6024.
Kearley, J., et al. (2015). Immunity 42, 566-579.
Kitamura, H., et al. (2007). J Urol 177, 1269-1272.
Korkolopoulou, P., et al. (1996). Br J Cancer 73, 148-153.
Lanier, L. L. (2013). Nat Rev Immunol 13, 73-74.
Lankat-Buttgereit, B., and Tampe, R. (2002). Physiol Rev 82, 187-204.
Lee, H. M., et al. (2000). Cancer Res 60, 1927-1933.
Liu, T., et al. (1997). J Immunol 159, 5364-5371.
Lou, Y., et al. (2008). Clinical Cancer Research 14, 1494-1501.
Lou, Y., et al. (2005). Cancer Res 65, 7926-7933.
Martin, M. U. (2013). Semin Immunol 25, 449-457.
Martinez-Gonzalez, I., et al. (2014). Immunity 41, 366-374.
Mehta, A. M., et al. (2008). Cancer Immunol Immunother 57, 197-206.
Musolino, C., et al. (2014). Acta haematologica 131, 165-166.
Nabe, T. (2014). Interleukin (IL)-33: J Pharmacol Sci.
Naoe, M., et al. (2002). BJU Int 90, 748-753.
Neill, D. R., et al. (2010). Nature 464, 1367-1370.
Pascual-Figal, D. A., and Januzzi, J. L. (2015). The American Journal of Cardiology 115, 3B-7B.
Rigamonti, N., and Bellone, M. (2012). Cancer Immunol Immunother 61, 453-468.
Ritz, U., and Seliger, B. (2001). Molecular Medicine 7, 149-158.
Roediger, B., and Weninger, W. (2015). Adv Immunol 125, 111-154.
Seliger, B., et al. (1997). Immunol Today 18, 292-299.
Seliger, B., et al. (2000a). Immunol Today 21, 455-464.
Seliger, B., et al. (2000b). Tissue Antigens 56, 327-336.
Setiadi, A. F., et al. (2008). Cancer Research 68, 9601-9607.
Shastri, N., and Gonzalez, F. (1993). J Immunol 150, 2724-2736.
Singal, D. P., et al. (1996). Int J Cancer 68, 629-636.
Slovin, S. (2015). Urologic oncology.
Smahel, M., et al. (2003). Vaccine 21, 1125-1136.
Spits, H., et al. (2013). Nat Rev Immunol 13, 145-149.
Tao, K., et al. (2008). BMC Cancer 8, 228.
Tominaga, S., et al. (2015). Cytokine 72, 105-108.
Vitale, M., et al. (1998). Cancer Res 58, 737-742.
Walker, J. A., et al. (2013). Nat Rev Immunol 13, 75-87.
Watson, N. F., et al. (2006). Cancer Immunol Immunother 55, 973-980.
Zhang, H., et al. (2003). Cancer Immun 3, 2.
Zhang, Q.-J., et al. (2008). PLoS ONE 3, e3097.
Zhang, Q. J., et al. (2007). Int J Cancer.
Zia, A., et al. (2001). Int J Cancer 93, 566-570.

We claim:

1. A method of enhancing immune recognition of lung carcinoma cells and thereby treating and/or inhibiting lung cancer progression by stimulating an immune response in a subject in need thereof, the method comprising administering to the subject interleukin-33 (IL-33) in combination with type 2 innate lymphoid cells (ILC2 cells).

2. The method of claim 1, wherein the lung cancer is metastatic.

3. A method of treating and/or inhibiting lung cancer progression in a subject in need thereof, the method comprising administering interleukin-33 (IL-33) in combination with type 2 innate lymphoid cells (ILC2 cells).

4. A method of treating and/or inhibiting lung cancer progression in a subject in need thereof, the method comprising stimulating type 2 innate lymphoid cells (ILC2 cells) ex vivo with interleukin-33 (IL-33) in combination with thymic stromal lymphopoietin (TSLP) and administering said stimulated ILC2 cells to said subject.

5. A method of enhancing immune recognition of lung carcinoma cells and thereby treating and/or inhibiting lung cancer progression in a subject in need thereof, the method comprising stimulating type 2 innate lymphoid cells (ILC2 cells) ex vivo with interleukin-33 (IL-33) in combination with thymic stromal lymphopoietin (TSLP) and administering said stimulated ILC2 cells to said subject.

6. A method of stimulating an anti-cancer immune response in a subject in need thereof, the method comprising stimulating type 2 innate lymphoid cells (ILC2 cells) ex vivo with interleukin-33 (IL-33) in combination with thymic stromal lymphopoietin (TSLP) and administering said stimulated ILC2 cells to said subject, wherein said cancer is lung cancer.

7. The method of claim 1, 3, 4, 5 or 6, wherein said ILC2 cells are autologous cells.

8. The method of claim 1, 3, 4, 5 or 6, wherein said ILC2 cells are heterologous cells.

9. The method of claim 1, 3, 4, 5 or 6, wherein the lung cancer is metastatic.

10. The method of claim 1, 3, 4, 5 or 6, further comprising administration of a therapy selected from the group consisting of cytokines, vaccine therapies and chemotherapeutics.

11. The method of claim 1, 3, 4, 5 or 6, further comprising administration of a therapy selected from the group consisting of TNF alpha; interleukin-21; interleukin-13; a combination of interleukin (IL)-4, IL-5, IL-9 and IL-13; interferon; GM-CSF; G-CSF; HDACi; methylation inhibitors; T cells, autologous B Cells, dendritic cells subsets, tumor antigens; antibodies; hematopoietic stem-cell transplantation; natural killer cells; Toll receptor agonists; chemokines; anti-angiogenic molecules; IL-2; chemotherapies; oncolytic viruses; adjuvants; cytotoxic agents; and therapies which deplete regulatory T cells.

12. The method of claim 11, wherein the interferon is selected from the group consisting of interferon alpha, interferon beta and interferon gamma.

* * * * *

SEQUENCE LISTING

<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: TAP1 Forward Primer

<400> SEQUENCE: 1
tggctcgttg gcaccctcaa a                                              21

<210> SEQ ID NO 2
<211> LENGTH: 22
<212> TYPE: DNA
<213> ORGANISM: Artificial Sequence
<220> FEATURE:
<223> OTHER INFORMATION: TAP1 Reverse Primer

<400> SEQUENCE: 2
tcagtctgca ggagccgcaa ga                                             22

<210> SEQ ID NO 3
<211> LENGTH: 20
<212> TYPE: DNA
<213> ORGANISM: Artificial Sequence
<220> FEATURE:
<223> OTHER INFORMATION: Beta-actin Forward Primer

<400> SEQUENCE: 3
atggatgacg atatcgctgc                                                20

<210> SEQ ID NO 4
<211> LENGTH: 21
<212> TYPE: DNA
<213> ORGANISM: Artificial Sequence
<220> FEATURE:
<223> OTHER INFORMATION: Beta-actin Reverse Primer

<400> SEQUENCE: 4
ttctccaggg aggaagagga t                                              21

<210> SEQ ID NO 5
<211> LENGTH: 24
<212> TYPE: DNA
<213> ORGANISM: Artificial Sequence
<220> FEATURE:
<223> OTHER INFORMATION: IL-33 Forward Primer

<400> SEQUENCE: 5
aggaagagat ccttgcttgg cagt                                           24

<210> SEQ ID NO 6
<211> LENGTH: 24
<212> TYPE: DNA
<213> ORGANISM: Artificial Sequence
<220> FEATURE:
<223> OTHER INFORMATION: IL-33 Reverse Primer

<400> SEQUENCE: 6
accatcacct tcttcccatc caca                                           24

<210> SEQ ID NO 7
<211> LENGTH: 18
<212> TYPE: DNA
<213> ORGANISM: Artificial Sequence

```
<220> FEATURE:
<223> OTHER INFORMATION: H2-K1 Forward Primer

<400> SEQUENCE: 7
cacgctgctc ctgctgtt                                                   18

<210> SEQ ID NO 8
<211> LENGTH: 21
<212> TYPE: DNA
<213> ORGANISM: Artificial Sequence
<220> FEATURE:
<223> OTHER INFORMATION: H2-K1 Reverse Primer

<400> SEQUENCE: 8
ttcacgctag agaatgaggg t                                               21

<210> SEQ ID NO 9
<211> LENGTH: 8
<212> TYPE: PRT
<213> ORGANISM: Artificial Sequence
<220> FEATURE:
<223> OTHER INFORMATION: Ovalbumin epitope (257-264)

<400> SEQUENCE: 9

Ser Ile Ile Asn Phe Glu Lys Leu
1               5

<210> SEQ ID NO 10
<211> LENGTH: 100
<212> TYPE: DNA
<213> ORGANISM: Artificial Sequence
<220> FEATURE:
<223> OTHER INFORMATION: IL33 promoter

<400> SEQUENCE: 10 tgagggcag aggagctggg acatgaccat gggggagggc tgtatgtgag ctaattctgc      60
tatgagtctg ggaggaaagg ggccacaaaa tccatcattt                          100

<210> SEQ ID NO 11
<211> LENGTH: 100
<212> TYPE: DNA
<213> ORGANISM: Artificial Sequence
<220> FEATURE:
<223> OTHER INFORMATION: IL33 promoter

<400> SEQUENCE: 11 tgagggcag aggagctggg acatgacggt gggggagggc tgtatgtgag ctaattctgc      60
tatgagtctg ggaggaaagg ggccacaaaa tccatcattt                          100
```